US012788331B2

(12) United States Patent
Zerhusen et al.

(10) Patent No.: US 12,788,331 B2

(45) **Date of Patent: *Nov. 10, 2026**

(54) PATIENT SUPPORT APPARATUS HAVING VITAL SIGNS MONITORING AND ALERTING

(71) Applicant: Hill-Rom Services, Inc., Batesville, IN (US)

(72) Inventors: Robert M. Zerhusen, Cincinnati, OH (US); Dan R. Tallent, Hope, IN (US); Brandon P. Fisk, Brookville, IN (US); Aziz A. Bhai, Fishers, IN (US); Eric D. Benz, Sunman, IN (US); Robert D Weitz, Westborough, MA (US); John Goewert, Batesville, IN (US); Frank Sauser, Cincinnati, OH (US); Nicholas C. Batta, Batesville, IN (US); Edward J. Koors, Indianapolis, IN (US); Jonathan D. Turner, Dillsboro, IN (US); Richard H. Heimbrock, Cincinnati, OH (US); John G. Byers, Batesville, IN (US); Nicholas A. Mann, Cincinnati, OH (US); Daniel McCoy, Wilmette, IL (US)

(73) Assignee: Hill-Rom Services, Inc., Batesville, IN (US)

( * ) Notice: Subject to any disclaimer, the term of this patent is extended or adjusted under 35 U.S.C. 154(b) by 7 days.

This patent is subject to a terminal disclaimer.

(21) Appl. No.: 19/024,475

(22) Filed: Jan. 16, 2025

(65) Prior Publication Data

US 2025/0152110 A1 May 15, 2025

Related U.S. Application Data

(63) Continuation of application No. 18/438,969, filed on Feb. 12, 2024, now Pat. No. 12,465,295, which is a (Continued)

(30) Foreign Application Priority Data

Mar. 22, 2017 (EM) ................................ 003817477

(51) Int. Cl.

*A61B 5/00* (2006.01)

*A61B 5/0205* (2006.01)

(Continued)

(52) U.S. Cl.

CPC ............ *A61B 5/746* (2013.01); *A61B 5/0205* (2013.01); *A61B 5/024* (2013.01); *A61B 5/1115* (2013.01);

(Continued)

(58) Field of Classification Search

CPC ....... A61B 5/746; A61B 5/0205; A61B 5/024; A61B 5/1115; A61B 5/6891;

(Continued)

(56) References Cited

U.S. PATENT DOCUMENTS

| | | | |
|---|---|---|---|
| 113,212 | A | 3/1871 | Sheble |
| 3,613,438 | A | 10/1971 | Esau |

(Continued)

FOREIGN PATENT DOCUMENTS

| | | | |
|---|---|---|---|
| CN | 102573615 | A | 7/2012 |
| CN | 103070685 | A | 5/2013 |

(Continued)

OTHER PUBLICATIONS

P J Murphy at al: "Nighttime drop in body temperature: a physiological trigger for sleep onset?", Sleep, Jul. 1, 1997 (Jul. 1, 1997), United States, pp. 505-511, XP055475260, Retrieved from the Internet [retrieved on May 15, 2018], DOI: 10.1093/sleep/20.7.505 (7 pages).

(Continued)

*Primary Examiner* — Amine Benlagsir

(74) *Attorney, Agent, or Firm* — Barnes & Thornburg LLP

(57) ABSTRACT

A patient support apparatus includes a sensor capable of detecting vital signs, setting acceptable limits for the vital signs, and includes structures for monitoring the vital signs and providing local and/or remote indications to caregivers if the vital signs fall outside of acceptable limits.

20 Claims, 41 Drawing Sheets

Related U.S. Application Data continuation of application No. 17/526,223, filed on Nov. 15, 2021, now Pat. No. 11,896,406, which is a continuation of application No. 15/660,360, filed on Jul. 26, 2017, now Pat. No. 11,172,892.

(60) Provisional application No. 62/442,223, filed on Jan. 4, 2017.

(51) Int. Cl.

| | |
|---|---|
| ***A61B 5/024*** | (2006.01) |
| ***A61B 5/11*** | (2006.01) |
| ***A61G 7/018*** | (2006.01) |
| ***A61G 7/05*** | (2006.01) |
| *A61B 5/08* | (2006.01) |
| *G03B 21/14* | (2006.01) |
| *G03B 21/20* | (2006.01) |
| *G16H 40/63* | (2018.01) |

(52) U.S. Cl.

CPC .......... *A61B 5/6891* (2013.01); *A61B 5/6892* (2013.01); *A61B 5/7282* (2013.01); *A61B 5/742* (2013.01); *A61B 5/7445* (2013.01); *A61G 7/018* (2013.01); *A61G 7/05* (2013.01); *A61G 7/0524* (2016.11); *A61B 5/08* (2013.01); *A61B 5/0816* (2013.01); *A61B 5/1113* (2013.01); *A61G 2203/30* (2013.01); *A61G 2203/70* (2013.01); *G03B 21/147* (2013.01); *G03B 21/2053* (2013.01); *G16H 40/63* (2018.01)

(58) Field of Classification Search

CPC ..... A61B 5/6892; A61B 5/7282; A61B 5/742; A61B 5/7445; A61B 5/08; A61B 5/0816; A61B 5/1113; A61B 5/7435; A61G 7/018; A61G 7/05; A61G 7/0524; A61G 2203/30; A61G 2203/70; G03B 21/147; G03B 21/2053; G16H 40/63

See application file for complete search history.

(56) References Cited

U.S. PATENT DOCUMENTS

| | | | | |
|---|---|---|---|---|
| 4,582,642 | A | 4/1986 | Crescentini et al. | |
| 4,595,023 | A | 6/1986 | Bonnet | |
| 4,602,643 | A | 7/1986 | Dietz | |
| 4,657,026 | A | 4/1987 | Tagg | |
| 4,681,098 | A | 7/1987 | Lee | |
| 4,757,825 | A | 7/1988 | Diamond | |
| 4,889,131 | A | 12/1989 | Salem et al. | |
| 4,967,195 | A | 10/1990 | Shipley | |
| 5,101,828 | A | 4/1992 | Welkowitz et al. | |
| 5,184,112 | A | 2/1993 | Gusakov | |
| 5,276,432 | A | 1/1994 | Travis | |
| 5,448,996 | A | 9/1995 | Bellin et al. | |
| 5,561,412 | A | 10/1996 | Novak et al. | |
| 5,738,102 | A | 4/1998 | Lemelson | |
| 5,964,720 | A | 10/1999 | Pelz | |
| 6,011,477 | A | 1/2000 | Teodorescu et al. | |
| 6,025,782 | A | 2/2000 | Newham | |
| 6,067,019 | A | 5/2000 | Scott | |
| 6,067,466 | A | 5/2000 | Selker et al. | |
| 6,208,250 | B1 | 3/2001 | Dixon et al. | |
| 6,656,125 | B2 | 12/2003 | Miscynski et al. | |
| 6,884,207 | B2 | 4/2005 | Pokusa | |
| 6,897,780 | B2 | 5/2005 | Ulrich et al. | |
| 6,984,207 | B1 | 1/2006 | Sullivan et al. | |
| 7,077,810 | B2 | 7/2006 | Lange et al. | |
| 7,245,956 | B2 | 7/2007 | Matthews et al. | |
| 7,253,366 | B2 | 8/2007 | Bhai | |
| 7,296,312 | B2 | 11/2007 | Vanderpohl, III et al. | |
| 7,306,564 | B2 | 12/2007 | Nakatani et al. | |
| 7,314,451 | B2 | 1/2008 | Halperin et al. | |
| 7,315,535 | B2 | 1/2008 | Schuman | |
| 7,316,171 | B2 | 1/2008 | Nemoto | |
| 7,319,386 | B2 | 1/2008 | Collins, Jr. et al. | |
| 7,396,331 | B2 | 7/2008 | Mack et al. | |
| 7,443,303 | B2 | 10/2008 | Spear et al. | |
| 7,557,718 | B2 | 7/2009 | Petrosenko et al. | |
| 7,629,890 | B2 | 12/2009 | Sullivan et al. | |
| 7,690,059 | B2 | 4/2010 | Lemire et al. | |
| 7,852,208 | B2 | 12/2010 | Collins, Jr. et al. | |
| 7,926,131 | B2 | 4/2011 | Vanderpohl, III et al. | |
| 8,157,730 | B2 | 4/2012 | Leboeuf et al. | |
| 8,161,826 | B1 | 4/2012 | Taylor | |
| 8,281,433 | B2 | 10/2012 | Riley et al. | |
| 8,444,558 | B2 | 5/2013 | Young et al. | |
| 8,510,126 | B2 | 8/2013 | Martin et al. | |
| 8,525,680 | B2 | 9/2013 | Riley et al. | |
| 8,752,220 | B2 | 6/2014 | Soderberg et al. | |
| 8,826,473 | B2 | 9/2014 | Flanagan et al. | |
| 8,844,073 | B2 | 9/2014 | Riley et al. | |
| 9,177,465 | B2 | 11/2015 | Vanderpohl, III | |
| 9,220,650 | B2 | 12/2015 | Yermaneni et al. | |
| 9,320,434 | B2 | 4/2016 | Proud | |
| 9,320,444 | B2 | 4/2016 | Hayes et al. | |
| 9,333,136 | B2 | 5/2016 | Gibson et al. | |
| 9,445,751 | B2 | 9/2016 | Young et al. | |
| 9,492,341 | B2 | 11/2016 | Huster et al. | |
| 9,655,795 | B2 | 5/2017 | O'Keefe et al. | |
| 9,655,798 | B2 | 5/2017 | Zerhusen et al. | |
| 9,717,896 | B2 | 8/2017 | Ferren et al. | |
| 10,004,451 | B1 | 6/2018 | Proud | |
| 10,058,290 | B1 | 8/2018 | Proud | |
| 10,238,342 | B2 | 3/2019 | Fleischer et al. | |
| 11,071,666 | B2 * | 7/2021 | Emmons | G16H 20/00 |
| 11,172,892 | B2 | 11/2021 | Zerhusen et al. | |
| 11,896,406 | B2 | 2/2024 | Zerhusen et al. | |
| 2005/0027416 | A1 | 2/2005 | Basir et al. | |
| 2005/0190062 | A1 | 9/2005 | Sullivan et al. | |
| 2005/0190068 | A1 | 9/2005 | Gentry et al. | |
| 2006/0042634 | A1 | 3/2006 | Derouen et al. | |
| 2006/0101581 | A1 | 5/2006 | Blanchard et al. | |
| 2007/0118054 | A1 | 5/2007 | Pinhas et al. | |
| 2007/0276202 | A1 | 11/2007 | Raisanen et al. | |
| 2007/0296600 | A1 | 12/2007 | Dixon et al. | |
| 2008/0005838 | A1 | 1/2008 | Wan Fong et al. | |
| 2008/0077026 | A1 | 3/2008 | Banet et al. | |
| 2008/0169931 | A1 | 7/2008 | Gentry et al. | |
| 2008/0269625 | A1 | 10/2008 | Halperin et al. | |
| 2008/0275349 | A1 | 11/2008 | Halperin et al. | |
| 2009/0054735 | A1 | 2/2009 | Higgins et al. | |
| 2009/0062623 | A1 | 3/2009 | Cohen et al. | |
| 2009/0069642 | A1 | 3/2009 | Gao et al. | |
| 2009/0088606 | A1 | 4/2009 | Cuddihy et al. | |
| 2009/0093686 | A1 | 4/2009 | Hu et al. | |
| 2009/0163774 | A1 | 6/2009 | Thatha et al. | |
| 2009/0287120 | A1 | 11/2009 | Ferren et al. | |
| 2009/0326339 | A1 | 12/2009 | Horvitz | |
| 2010/0016685 | A1 | 1/2010 | Muehlsteff et al. | |
| 2010/0099954 | A1 | 4/2010 | Dickinson et al. | |
| 2010/0170043 | A1 | 7/2010 | Young et al. | |
| 2011/0068935 | A1 * | 3/2011 | Riley | A61B 5/02055 340/575 |
| 2011/0234408 | A1 | 9/2011 | Dixon et al. | |
| 2011/0301432 | A1 | 12/2011 | Riley et al. | |
| 2012/0259245 | A1 | 10/2012 | Receveur | |

(56) References Cited

U.S. PATENT DOCUMENTS

| | | | | |
|---|---|---|---|---|
| 2013/0135137 | A1 | 5/2013 | Mulder et al. | |
| 2014/0115784 | A1 | 5/2014 | Jahannigman et al. | |
| 2014/0259410 | A1* | 9/2014 | Zerhusen | A61G 7/012 5/600 |
| 2015/0033295 | A1 | 1/2015 | Huster | |
| 2016/0022218 | A1 | 1/2016 | Hayes et al. | |
| 2016/0117496 | A1* | 4/2016 | Bielstein | A61N 1/3925 607/5 |
| 2016/0212783 | A1* | 7/2016 | Hampapuram | G06F 3/1423 |
| 2018/0184984 | A1 | 7/2018 | Zerhusen et al. | |
| 2020/0297955 | A1* | 9/2020 | Shouldice | A61M 16/06 |
| 2022/0071571 | A1 | 3/2022 | Zerhusen et al. | |

FOREIGN PATENT DOCUMENTS

| | | | |
|---|---|---|---|
| CN | 105142501 | A | 12/2015 |
| JP | 2002056477 | A | 2/2002 |
| JP | 2010284498 | A | 12/2010 |
| JP | 2011030919 | A | 2/2011 |
| JP | 2011136145 | A | 7/2011 |
| JP | 2012163587 | A | 8/2012 |
| JP | 2014094085 | A | 5/2014 |
| JP | 2017018380 | A | 1/2017 |
| WO | 2008024561 | A2 | 2/2008 |
| WO | 2014151577 | A1 | 9/2014 |
| WO | 2016073186 | A1 | 5/2016 |
| WO | 2016196403 | A1 | 12/2016 |

OTHER PUBLICATIONS

Decision of Rejection in related JP2020-081441, dated May 31, 2022 (2 pages).

Tal Klap et al: "Using piezoelectric sensor for continuous-contact-free monitoring of heart and respiration rates in real-life hospital settings," Computing in Cardiology 2013, Jan. 1, 2013 (Jan. 1, 2013), pp. 671-674, XP055475251, ISSN: 2325-8861, ISBN: 978-1-4799-0884-4.

Communication Pursuant to EPO Article 94(3) in related EP Application No. 18150240.2-1113, dated Mar. 12, 2021 (7 pages).

EP Extended Search Report in related case EP18150240.2, dated May 25, 2018 (11 pages).

English translation of JP Official Action in related case JP2017248916, dated Apr. 23, 2019 (12 pages).

JP Official Action in related case JP2017248916, dated Apr. 23, 2019 (10 pages).

* cited by examiner

PATIENT SUPPORT APPARATUS HAVING VITAL SIGNS MONITORING AND ALERTING

RELATED APPLICATIONS

This application is a continuation of U.S. patent application Ser. No. 18/438,969, filed on Feb. 12, 2024, which is a continuation of U.S. patent application Ser. No. 17/526,223, filed on Nov. 15, 2021, now U.S. Pat. No. 11,896,406, on Feb. 13, 2024, which is a continuation of U.S. patent application Ser. No. 15/660,360, filed Jul. 26, 2017, now U.S. Pat. No. 11,172,892, issued Nov. 16, 2021, which claims priority to U.S. Provisional Patent Application No. 62/442,223, filed Jan. 4, 2017, both of which are herein incorporated by reference in their entirety.

The present application also claims priority 35 U.S.C. § 119 (a) of European Community Design Application No. EM003817477 filed on Mar. 22, 2017.

BACKGROUND

The present disclosure is related to patient support apparatuses having alerting capabilities. More specifically, the present disclosure is related to patient support apparatuses that include sensors for monitoring vital signs and structures for alerting caregivers when the vital signs are unacceptable.

Monitoring physiological parameters of a person supported by a person support apparatus is an ongoing challenge. Space constraints in the patient's vicinity provide opportunities for effective use of technology to monitor the patient without adding to the number of devices in the vicinity of the patient. While several systems and methods exist for sensing physiological signals of a person supported by a person support apparatus, opportunity exists for continued development in this area.

Still further, a need exists for a system capable of providing a caregiver, such as a nurse, information regarding vital signs of a patient without requiring the caregiver to disturb the patient.

SUMMARY

The present application discloses one or more of the features recited in the appended claims and/or the following features which, alone or in any combination, may comprise patentable subject matter:

In a first aspect of the present disclosure, a detection and notification system for a patient support apparatus comprises a sensor detecting a vital sign of a patient; a controller operable to receive a signal from the sensor indicative of the vital sign of the patient, the controller operable to compare the vital sign to pre-established limits to determine whether the vital sign is within an acceptable range; and a notification system operable to respond to commands from the controller to provide an indication as to whether the vital sign is within the acceptable range or that alarm condition exists, the indication discernible by a user spaced apart from the patient support apparatus that the detection notification system is associated.

In some embodiments, the sensor simultaneously detects a first vital sign and a second vital sign.

In some embodiments, the detection notification system includes a plurality of sensors simultaneously detecting a vital sign of the patient.

In some embodiments, the plurality of sensors each detects both a first vital sign and a second vital sign.

In some embodiments, the controller is operable to receive a signal from the patient support apparatus indicative of the position of a patient supported on the patient support apparatus, the controller operable to utilize the position of the patient to determine whether to disregard the vital sign information from one of the plurality of sensors.

In some embodiments, the controller is operable to prompt a user to suspend the operation of the notification system based on the position of the patient.

In some embodiments, the controller is operable to receive a signal from the patient support apparatus indicative of the position of a patient supported on the patient support apparatus, and further operable to prompt the user to suspend operation of the notification system based on the position of the patient.

In some embodiments, the controller is operable to receive signals indicative of the position of components of the patient support apparatus and to determine the acceptable range of the vital sign based, at least in part, on the position of at least one of the components of the patient support apparatus.

In some embodiments, the controller is operable to communicate with an electronic medical record system to receive information from the electronic medical record system indicative of a medical history of a patient supported on the patient support apparatus and to determine the acceptable range of the vital sign based, at least in part, on the patient's medical history.

In some embodiments, the controller is operable to utilize the medical history of the patient to perform an algorithm that analyzes the vital sign to determine that the patient is likely to experience an adverse event and to provide a notification discernible by a user that the likelihood of the adverse event has reached a threshold.

In a second aspect of the present disclosure, a patient support apparatus comprises at least one sensor, the at least one sensor operable to provide a signal indicative of a vital sign of a patient supported on the patient support apparatus, and a notification system coupled to the sensor, the notification system operable to process signals from the sensor which provide an indication of a vital sign to determine a vital sign, compare the vital sign to a predefined acceptable limit, and, if the vital sign deviates from the established acceptable limit, provide a visual indication of the deviation by illuminating a first iconic representation of vital signs in a first manner, if the status of the particular component does not deviate from the established acceptable operating condition for that component, illuminating the first iconic representation in a second manner.

In some embodiments, the notification system is operable to project the first iconic representation to a surface spaced apart from the patient support apparatus.

In some embodiments, the first iconic representation is simultaneously illuminated on a surface of the patient support apparatus and projected onto the surface spaced apart from the patient support apparatus.

In some embodiments, the first iconic representation is projected to the surface spaced apart from the patient support apparatus by a projector located on the patient support apparatus.

In some embodiments, illuminating the first iconic representation in a first manner comprises illuminating the first iconic representation in a first color and illuminating the first iconic representation in a second manner comprises illuminating the first iconic representation in a second color.

In some embodiments, providing the visual indication of the deviation includes simultaneously illuminating a first iconic representation of the component on a surface of the patient support apparatus in a first color and projecting the first iconic representation of the component on the surface spaced apart from the patient support apparatus in the first color.

In some embodiments, providing the visual indication of the lack of a deviation includes simultaneously illuminating a first iconic representation of the component on a surface of the patient support apparatus in a second color and projecting the first iconic representation of the component on the surface spaced apart from the patient support apparatus in the second color. In some embodiments, providing the visual indication of the deviation includes simultaneously illuminating a first iconic representation of the component on a surface of the patient support apparatus in a first color and projecting the first iconic representation of the component on the surface spaced apart from the patient support apparatus in the first color.

In some embodiments, providing the visual indication of the lack of a deviation includes simultaneously illuminating a first iconic representation of the component on a surface of the patient support apparatus in a second color and projecting the first iconic representation of the component on the surface spaced apart from the patient support apparatus in the second color.

In some embodiments, the surface spaced apart from the patient support apparatus is the surface of a floor, the first iconic representation being projected to a position that is not directly below any portion of the patient support apparatus.

In some embodiments, the patient support apparatus further comprises a frame, a barrier supported by the frame and movable vertically relative to the frame, a control system, and a user interface.

In some embodiments, a visual indication of the status of a patient position is provided at a foot end of the patient support apparatus.

In some embodiments, a visual indication of the status of the patient position is illuminated on a floor under the foot end of the patient support apparatus.

In some embodiments, a visual indication of the status of the patient position is provided by an illuminated grip on the barrier.

In some embodiments, a visual indication of the status of a condition of at least one feature of the patient support apparatus is provided at a foot end of the patient support apparatus.

In some embodiments, a visual indication of the status of a condition of at least one feature of the patient support apparatus is provided by illuminating an indication on the floor under the foot end of the patient support apparatus.

In some embodiments, the patient support apparatus includes structures which permit illumination of iconic representations on the floor beneath the patient support apparatus.

In some embodiments, the sensor is removably supported on the frame of the patient support apparatus.

In some embodiments, the frame is configured to support the sensor in multiple mounting locations.

In some embodiments, the patient support apparatus comprises multiple sensors, each sensor mounted at a different location on the frame.

In some embodiments, the control system is operable to detect a location of a patient and modify the operation of the notification system to disregard at least one of the sensors based on the patient location.

In some embodiments, the patient support apparatus includes two sensors mounted on a first frame member and one sensor mounted on a second frame member that is movable relative to the first frame member.

In some embodiments, the patient support apparatus further comprises a mattress supported on the frame and the sensor is located internally in the mattress.

According to a third aspect of the present disclosure, a patient support apparatus comprises a notification system operable of projecting indicia indicative of a condition associated with the patient support apparatus, the notification system including a light source and a projector assembly, the projector assembly operable to receive light from the light source and direct the light through a lens having a pre-distorted negative of the indicia such that when the light passes through the lens, an undistorted image is projected onto a surface spaced apart from the patient support apparatus.

In some embodiments, the projector assembly directs the light at a projection angle that is not orthogonal to the surface spaced apart from the patient support apparatus.

In some embodiments, the pre-distortion of the negative of the indicia is adjusted to correspond to the projection angle.

In some embodiments, the notification system includes a plurality of light sources and a plurality of projector assemblies, each projector assembly associated with a respective light source, each projector assembly operable to receive light from the respective light source and direct the light through a lens having a pre-distorted negative of the indicia such that when the light passes through the lens, an undistorted image is projected onto a surface spaced apart from the patient support apparatus, each projector assembly projecting a respective indicia, each indicia being indicative of a different condition.

In some embodiments, a first indicia is indicative of the condition of a patient vital sign and a second indicia is indicative of a status of a component of the patient support apparatus.

In some embodiments, each respective projection assembly projects at a projection angle that is not orthogonal to the surface spaced apart from the patient support apparatus, the pre-distortion of the negative associated we each respective projection assembly being adjusted to correspond to the projection angle of the particular projection assembly.

According to a fourth aspect of the present disclosure, patient support apparatus comprises a controller, the controller coupled to memory which stores a serial number for the particular patient support apparatus, a replaceable component, the replaceable component including memory which stores a serial number for the replaceable component, and a user interface, wherein the controller is operable to execute a process which verify that the patient support apparatus is properly authorized to execute the functionality of the replaceable component by detecting the presence of the replaceable component, evaluating the serial number of one of the patient support apparatus and the replaceable component and provides an indication of the status of the authorization at the user interface.

In some embodiments, if the controller determines that the functionality of the replaceable component is not properly authorized, the controller is operable to prompt a user to enter an authorization code before executing the functionality of the replaceable component at the user interface.

In some embodiments, the authorization code is based, at least in part, on the serial number of the replaceable component.

In some embodiments, the authorization code is based, at least in part, on the serial number of the patient support apparatus.

In some embodiments, the authorization code is based, at least in part, on the serial number of the patient support apparatus.

In some embodiments, the controller monitors for the presence of a replaceable component and regularly compares the serial number of the replaceable component with the serial number of the authorized replaceable component to determine if a different replaceable component has been substituted.

In some embodiments, if the controller determines that a replaceable component has been substituted, the controller disables the functionality of the replaceable component and prompts the user to enter an authorization code for the substituted replaceable component at the user interface.

In some embodiments, the patient support apparatus comprises a detection and notification system for monitoring at least one vital sign of a patient supported on the patient support apparatus and the replaceable component is a vital sign sensor.

In some embodiments, the detection and notification system comprises multiple sensors, each sensor being monitored by the controller to determine that the patient support apparatus has been authorized for the particular sensor.

In some embodiments, the controller provides an indication of the status of the authorization at the user interface.

According to a fifth aspect of the present disclosure, a patient support apparatus comprises a detection and notification system for detecting at least one vital sign of a patient supported on the patient support apparatus, the detection and notification system including a sensor detecting a vital sign of the patient, the sensor not in contact with the patient; a controller operable to receive a signal from the sensor indicative of the vital sign of the patient, the controller operable to compare the vital sign to pre-established limits to determine whether the vital sign is within an acceptable range; and a notification system operable to respond to commands from the controller to provide an indication as to whether the vital sign is within the acceptable range or that alarm condition exists, the indication discernible by a user spaced apart from the patient support apparatus.

In some embodiments, the sensor detects multiple vital signs.

In some embodiments, the sensor simultaneously detects multiple vital signs.

In some embodiments, the sensor comprises a plurality of sensors.

In some embodiments, the patient support apparatus is configured to permit a particular sensor to be positioned in any one of a number of positions on the patient support apparatus.

In some embodiments, the controller is operable to disregard the signal of a sensor.

In some embodiments, the controller is operable to disregard the signal of a sensor if the controller determines that a patient is not properly positioned to be monitored by the sensor.

In some embodiments, the patient support apparatus includes a user interface in communication with the controller, the user interface operable to provide an indication of the status of at least one vital sign of the patient.

In some embodiments, the sensor simultaneously detects multiple vital signs and the patient support apparatus includes a user interface in communication with the controller, the user interface operable to provide an indication of the status of each detected vital sign of the patient.

In some embodiments, the controller is configured to allow a user to set alarm limits for a detected vital sign.

In some embodiments, the notification system operable to respond to commands from the controller to provide an indication as to whether a signal has been lost from a sensor.

In some embodiments, the controller is operable to monitor the signal from the sensor and determine if an adverse event is likely to occur based on the signal, independently of whether the signal exceeds a pre-set limit.

In some embodiments, the notification system is operable to provide an indication of the likelihood of the adverse event.

In some embodiments, the notification system is adjustable to provide local indications of a condition, remote indications of a condition, or both local and remote indications of a condition.

In some embodiments, the notification system is operable to prompt a user to either accept or rejection questionable data.

In some embodiments, the patient support apparatus includes a mattress and a sensor is positioned in the mattress.

In some embodiments, the controller determines whether a particular sensor has been authorized for use on the patient support apparatus.

In some embodiments, the controller prompts a user to enter an authorization code if a particular sensor has not previously been authorized for use on the patient support apparatus.

In some embodiments, the controller continuously monitors to confirm that a particular sensor has been authorized for use on the patient support apparatus and if a new sensor is substituted, controller prompts a user to enter an authorization code if a particular sensor has not previously been authorized for use on the patient support apparatus.

In some embodiments, an alert limit for a vital sign is determined automatically by the controller.

In some embodiments, the controller determines an alert limit for a vital sign based on patient medical history information from an electronic medical record system in communication with the controller.

In some embodiments, the controller determines an alert limit for a vital sign based on based on a bed condition.

In some embodiments, the patient support apparatus comprises a siderail with a grip and the notification system provides an indication as to whether the vital sign is within the acceptable range or that alarm condition exists at the grip by illuminating the grip in a color associated with a status of the vital sign.

In some embodiments, the patient support apparatus includes a touchscreen and the notification system provides an indication as to whether the vital sign is within the acceptable range or that alarm condition exists at a touchscreen.

In some embodiments, the patient support apparatus includes indicator panel and the notification system provides an indication as to whether the vital sign is within the acceptable range or that alarm condition exists at the indicator panel.

In some embodiments, the patient support apparatus includes a link to an external nurse call system and the notification system provides an indication as to whether the vital sign is within the acceptable range or that alarm condition exists through the link.

In some embodiments, the patient support apparatus includes a projection system for projecting indicia to a surface spaced apart from the patient support apparatus and the notification system provides an indication as to whether the vital sign is within the acceptable range or that alarm condition exists by projecting indicia associated with the status of the vital sign on the surface.

In some embodiments, the projection system includes a light source and a projector assembly, the projector assembly operable to receive light from the light source and direct the light through a lens having a pre-distorted negative of the indicia such that when the light passes through the lens, an undistorted image is projected onto a surface spaced apart from the patient support apparatus.

In some embodiments, the projector assembly directs the light at a projection angle that is not orthogonal to the surface spaced apart from the patient support apparatus.

In some embodiments, the pre-distortion of the negative of the indicia is adjusted to correspond to the projection angle.

In some embodiments, the notification system includes a plurality of light sources and a plurality of projector assemblies, each projector assembly associated with a respective light source, each projector assembly operable to receive light from the respective light source and direct the light through a lens having a pre-distorted negative of the indicia such that when the light passes through the lens, an undistorted image is projected onto a surface spaced apart from the patient support apparatus, each projector assembly projecting a respective indicia, each indicia being indicative of a different condition.

In some embodiments, a first indicia is indicative of the condition of a patient vital sign and a second indicia is indicative of a status of a component of the patient support apparatus.

In some embodiments, each respective projection assembly projects at a projection angle that is not orthogonal to the surface spaced apart from the patient support apparatus, the pre-distortion of the negative associated we each respective projection assembly being adjusted to correspond to the projection angle of the particular projection assembly.

Additional features, which alone or in combination with any other feature(s), including those listed above and those listed in the claims, may comprise patentable subject matter and will become apparent to those skilled in the art upon consideration of the following detailed description of illustrative embodiments exemplifying the best mode of carrying out the invention as presently perceived.

BRIEF DESCRIPTION OF THE DRAWINGS

The detailed description particularly refers to the accompanying figures in which.

DETAILED DESCRIPTION

Figure 1:
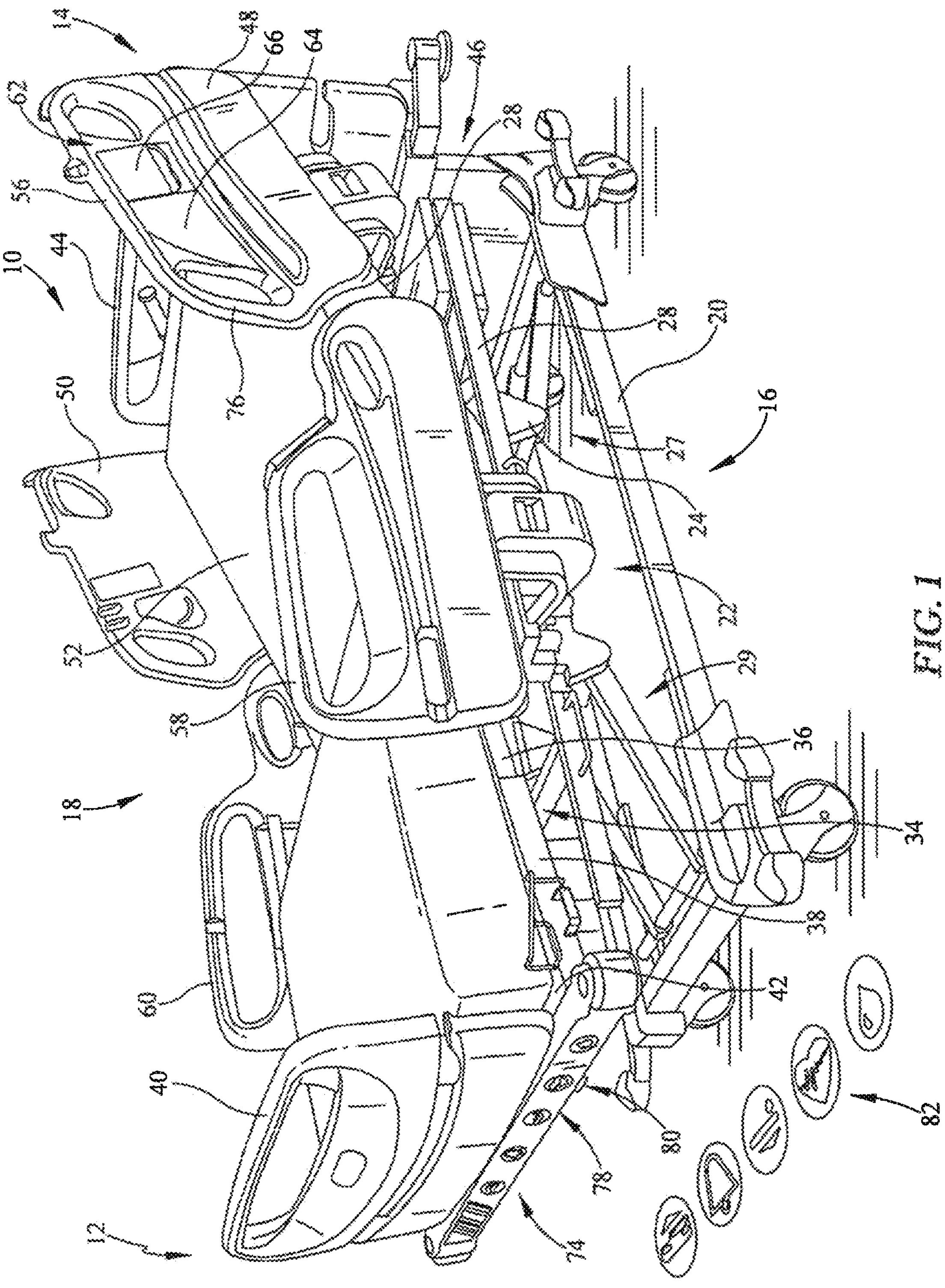
FIG. 1 is a perspective view of a patient support apparatus according to the present disclosure.
Figure 2:
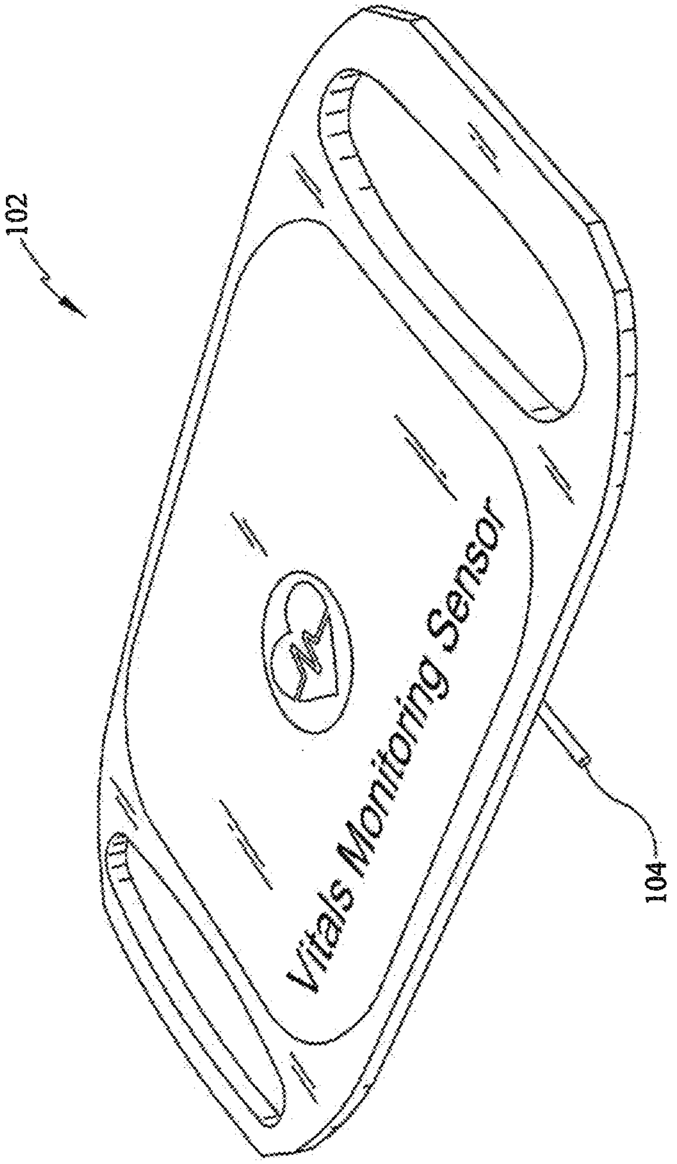
FIG. 2 is a perspective view of a sensor capable of detecting a patient's vital signs without contacting the patient.
Figure 3:
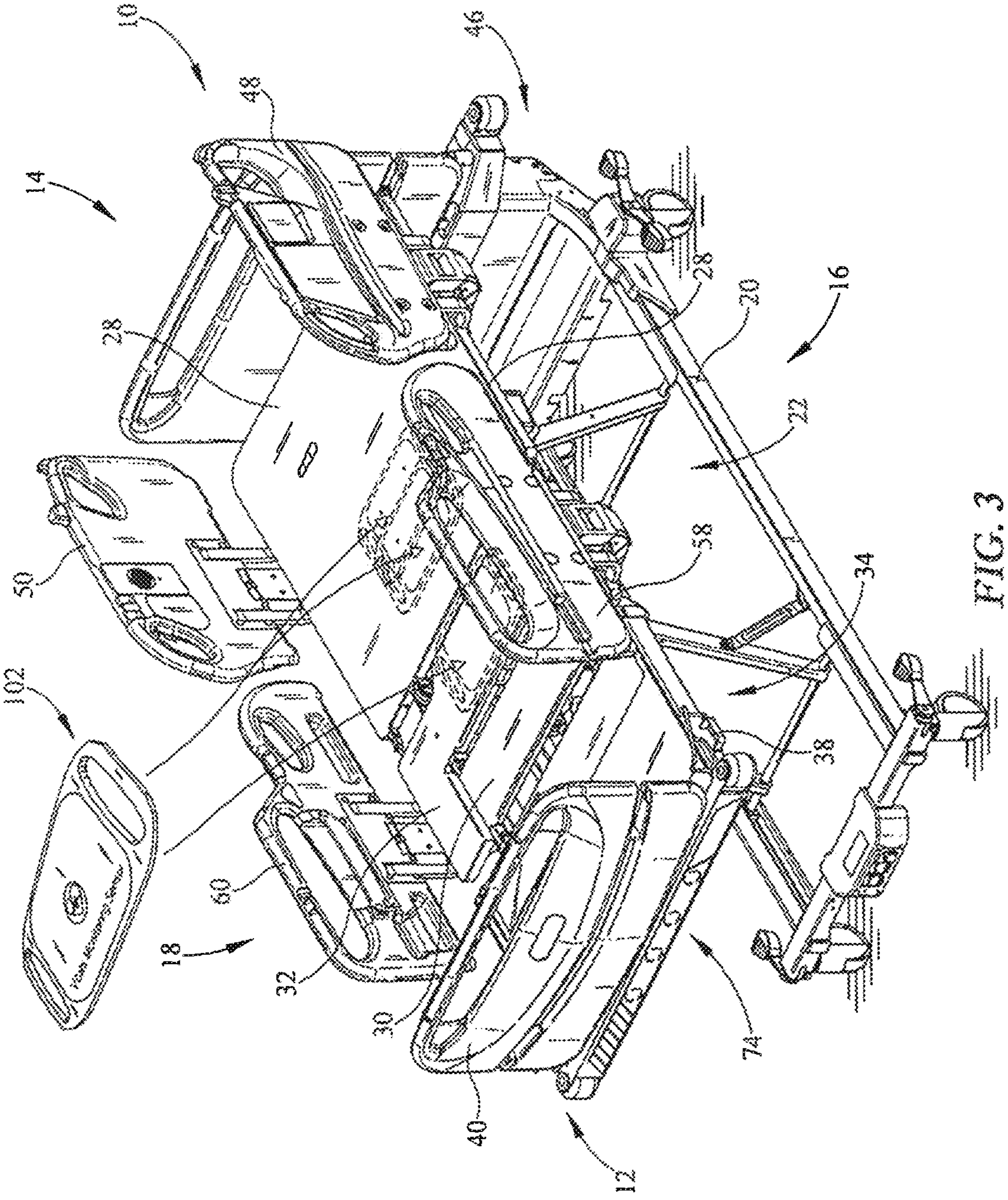
FIG. 3 is a perspective view the patient support apparatus of FIG. 1 with portions removed, FIG. 3 showing the potential of positioning the sensor of FIG. 2 in various locations on the patient support apparatus.

Referring to FIG. 1, a patient support apparatus 10 is illustratively embodied as a hospital bed 10. The hospital bed 10 includes an integrated vital signs monitoring system 100 including a sensor 102 mounted to a deck section of the hospital bed 10 as shown in FIG. 3. The view shown in FIG. 1 is generally taken from a position that is oriented at the left side, foot end of the hospital bed 10. For purposes of orientation, the discussion of the hospital bed 10 will be based on the orientation of a patient supported on the hospital bed 10 in a supine position. Thus, the foot end 12 of the hospital bed 10 refers to the end nearest the patient's feet when the patient is supported on the hospital bed 10 in the supine position. The hospital bed 10 has a head end 14 opposite the foot end 12. A left side 16 refers to the patient's left when the patient is lying in the hospital bed 10 in a supine position. The right side 18 refers to the patient's right. When reference is made to the longitudinal length of the hospital bed 10, it refers a direction that is represented by the lines that generally extend between the head end 14 and foot end 12 of the hospital bed 10. Similarly, lateral width of the hospital bed 10 refers to a direction that is represented by the lines that generally extend between the left side 16 and right side 18.

The hospital bed 10 includes a base frame 20 which supports a lift system 22. The lift system 22 engages the base and an upper frame 24 such that the lift system 22 moves the upper frame 24 vertically relative to the base frame 20. The lift system 22 includes a head end linkage 27 and a foot end linkage 29. Each of the linkages 27 and 29 are independently operable and may be operated to cause the hospital bed 10 to move into a tilt position which is when the head end 14 of the upper frame 24 is positioned lower than the foot end 12 of the upper frame 24. The hospital bed 10 may also be moved to a reverse tilt position with the foot end 12 of the upper frame 24 is positioned lower than the head end 14 of the upper frame 24.

The upper frame 24 supports a load frame 26. The load frame 26 supports a head deck 28 which is movable relative to the load frame 26. The load frame 26 also supports an articulated seat deck 30 (seen in FIG. 3), also movable relative to the load frame 26 and a fixed seat deck 32 (also seen in FIG. 3). Also supported from the load frame 26 is a foot deck 34 that is articulated and moveable relative to the load frame 26. The foot deck 34 in the illustrative embodiment of FIG. 1 provides for powered pivoting of the foot deck 34 and manual extension and retraction of the foot deck 34 to vary the length of the foot deck 34. In other embodiments, powered pivoting of the foot deck 34 may be omitted and the related movement may be caused manually, or follow movement of the articulated seat deck 30. In addition, in some embodiments, extension and retraction of the foot deck 34 may be powered by an actuator.

The foot deck 34 includes a first portion 36 and a second portion 38, which moves relative to the first portion 36 to vary the size of the foot deck 34. The second portion 38 moves generally longitudinally relative to the first portion 36 to vary the longitudinal length of the foot deck 34 and, thereby, the longitudinal length of the hospital bed 10.

A foot panel 40 is supported from the second portion 38 and extends vertically from an upper surface 42 of the second portion 38 to form a barrier at the foot end 12 of the hospital bed 10. A head panel 44 is positioned on an upright structure 46 of the base frame 20 and extends vertically to form a barrier at the head end 14 of the hospital bed 10. A left head siderail 48 is supported from the head deck 28 and is moveable between a raised position shown in FIG. 1 and a lowered position as is known in the art. A right head siderail 50 is also moveable between the raised position of FIG. 1 and lowered position. As shown in FIG. 1, in the raised position, the siderails 48 and 50 extend above an upper surface 52 of a mattress 54 of the hospital bed 10 when the siderails 48 and 50 are in a raised position. In a lowered position an upper edge 56 of the left head siderail 48 is below the upper surface 52.

The hospital bed 10 also includes a left foot siderail 58 and a right foot siderail 60, each of which is supported directly from the load frame 26. Each of the siderails 48, 50, 58, and 60 are operable to be lowered to a position below the upper surface 52. It should be noted that when the head deck 28 is moved, the head siderails 48 and 50 move with the head deck 28 so that they maintain their relative position to the patient. This is because both of the head siderails 48 and 50 are supported by the head deck 28.

Figure 12:
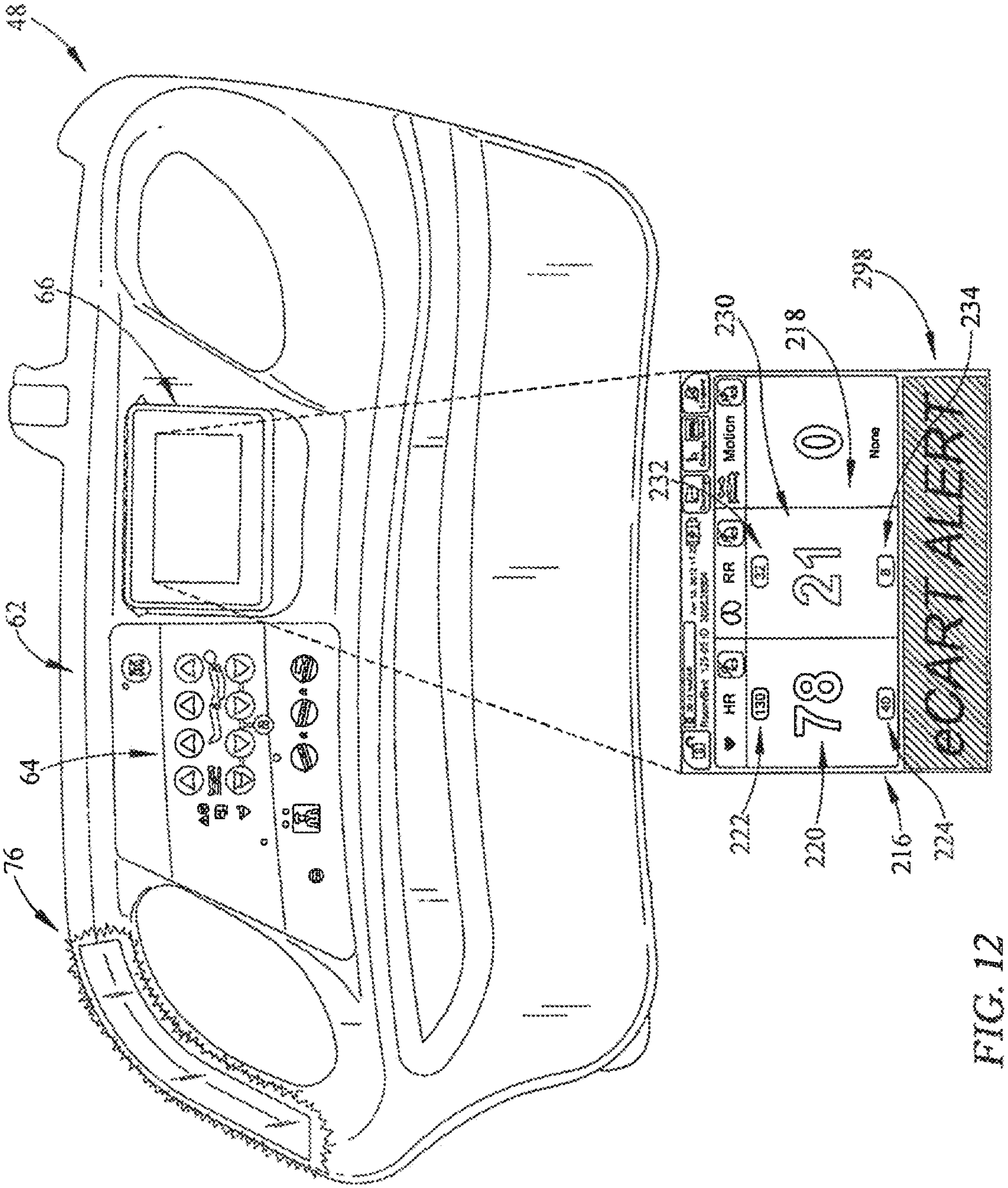
FIG. 12 is a plan view of a siderail of the patient support apparatus of FIG. 1 including an enlarged view of a diagrammatic representation of a screen displayed on a graphical user interface of the patient support apparatus.

Referring to the left head siderail 48 shown in FIG. 12, a user interface 62 includes a hard panel 64 and a graphical user interface 66. The user interface 62 will be discussed in further detail below, but it should be understood that the hard panel 64 provides indications to a user regarding the status of certain functions of the hospital bed 10 as well as providing a standard set of fixed input devices. The graphical user interface 66 includes a touchscreen display that provides information to a user as well as allowing for flexible, menu driven, operation of certain functions of the hospital bed 10. The graphical user interface 66, also known as a flip-up display (FUD), is mounted to the siderail 48 with a pivotable connection so that the graphical user interface 66 may be pivoted to allow a user the more easily view and interact with the graphical user interface 66, as is known in the art. In some embodiments, the right head siderail 50 may include a second graphical user interface duplicative of the graphical user interface 66.

Additional information is provided to a caregiver through an optional indicator panel 74 which displays the status of various conditions of the hospital bed 10 graphically to a caregiver at the foot end 12 of the hospital bed 10. The location of the indicator panel 74 makes the statuses of the conditions easily discernable from a distance, such that a caregiver may quickly ascertain the statuses from the hallway or the door of a patient's room. As will be discussed below, additional indication of the statuses may be projected on the floor under the foot end 12 of the hospital bed 10, providing larger images on the floor, making the images more easily discerned by a caregiver. Similarly, an illuminated grip 76 is positioned on the left head siderail 48, the illuminated grip 76 being selectively illuminated in different colors to provide an indication of the status of one or more functions of the hospital bed 10 to a caregiver. In some embodiments, the right head siderail 50 also includes an illuminated grip similar to the illuminated grip 76 and which includes the functionality of the illuminated grip 76.

The head end siderails 48 and 50 are configurable to provide additional indications of the status of components of the hospital bed 10 under the control of a notification system 180 by illuminating the grip 76 of the head siderails 48, 50. The structure used to illuminate the grip 76 is similar to that disclosed in a PCT application WO2016/196403, filed May 29, 2016, titled "PATIENT SUPPORT APPARATUS," and incorporated by reference herein for the disclosure of a structure for illuminating a grip of a siderail.

In operation, the grip 76 has four states, not illuminated, illuminated in a blue color, illuminated in an amber color, or illuminated in a red color. In the current embodiment, the grip 76 is not illuminated in one of two conditions: if a patient position monitoring system is disarmed and a patient is in hospital bed 10, or if the patient position monitoring system is armed and the patient is in the proper position in the bed 10. The grip 76 is illuminated blue if the patient position monitoring system is disarmed the patient is out of the hospital bed 10. The blue illumination tends to provide additional lighting for the patient if the ambient light is relatively low. The grip 76 is illuminated in an amber color if the patient position monitoring system is armed and the patient is not in the proper position. This amber illumination provides an additional indication to a caregiver of the alarm condition of the patient position monitoring system. The grip 76 is illuminated in a red color if the patient vital signs monitoring system 100 is in an alarm state, thus, providing an additional indication to a caregiver of the alarm condition of the vital signs monitoring system.

In the illustrative embodiment, the sensor 102 is a non-contact vital signs monitoring sensor available from Early-Sense Inc., 135 Beaver Street Suite 307, Waltham, MA 02452. It provides a signal indicative of a detected heart rate and a signal indicative of a detected respiration rate that is processed by a controller supported on the hospital bed 10. The sensor 102 may be mounted in multiple locations on either the fixed seat deck 32 or head deck 28 as suggested in FIG. 3. In some embodiments, multiple sensors 102 may be positioned on the fixed seat deck 32 and/or head deck 28 to provide multiple detection points with the signals from each of the multiple sensors 102 being monitored to determine an accurate vital sign signal. The use of redundant signals reduces the risk of signal loss due to movement or improper positioning of the patient on the hospital bed 10. The sensor 102 has a relatively thin thickness 104 shown in FIG. 3. This thin profile permits the sensor 102 to be placed under the mattress 54 and does not interfere with the functionality or therapeutic benefit of the mattress 54. In other embodiments, a different piezoelectric sensor may be utilized in place of the sensor 102.

Figure 16:
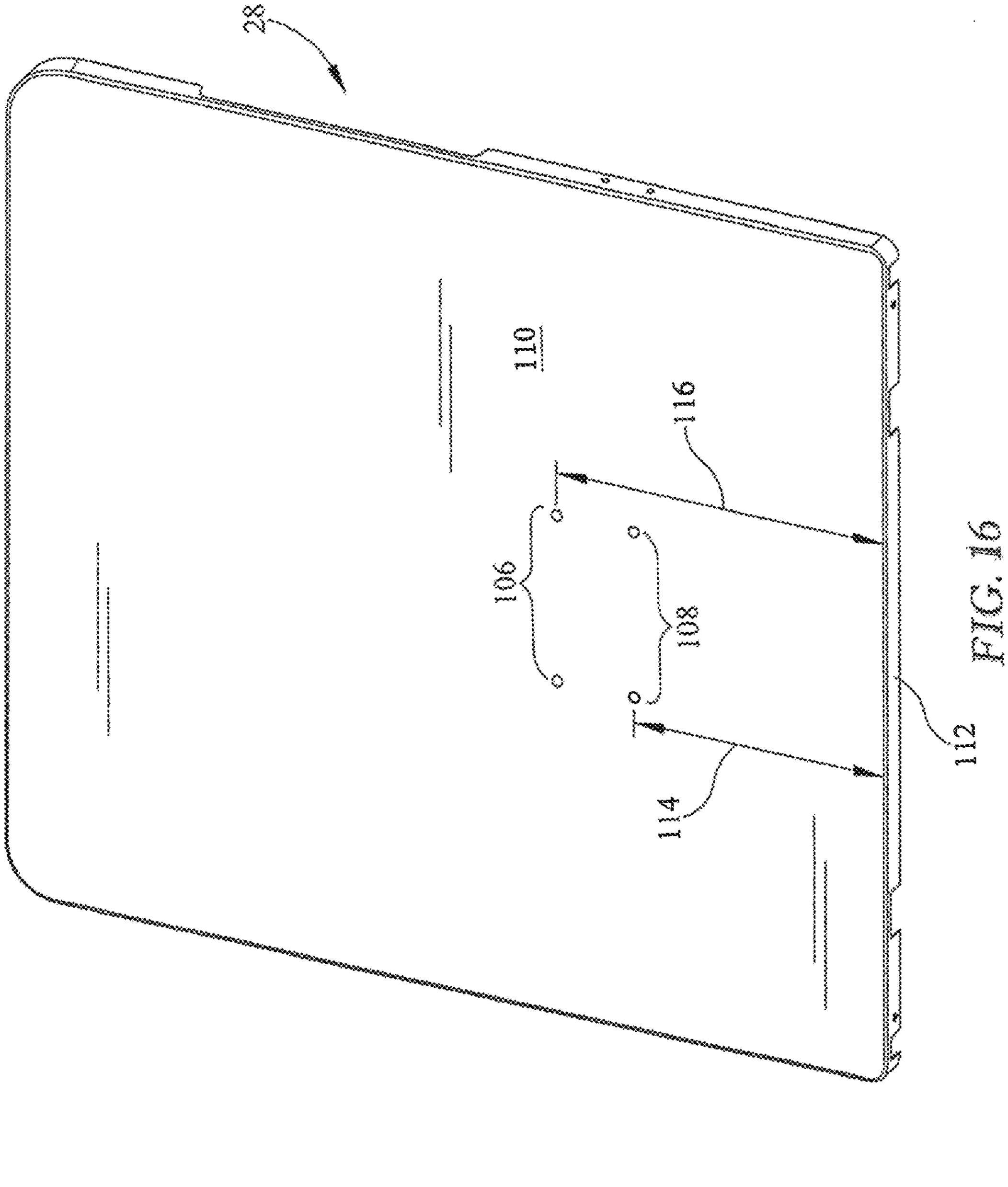
FIG. 16 is a perspective view of the front side of a head deck section of the patient support apparatus.

Referring to FIG. 16, the head deck 28 is formed to include two separate pairs of holes 106 and 108 formed in a surface 110 of the head deck 28. The first pair of holes 106 is spaced a first distance 116 from a lower edge 112 of the head deck 28. The second pair of holes 108 is positioned a second distance 114 from the lower edge 112. The variation in spacing permits the location of the sensor 102 as suggested in FIG. 3. The difference in spacing allows the location of the sensor 102 to be optimized based on the size of the patient being positioned on the hospital bed 10. Better vitals detection for a smaller stature patient is achieved by positioning the sensor 102 to engage holes 108, whereas better vitals detection is achieved for a larger stature patient by utilizing holes 106.

Figure 17:
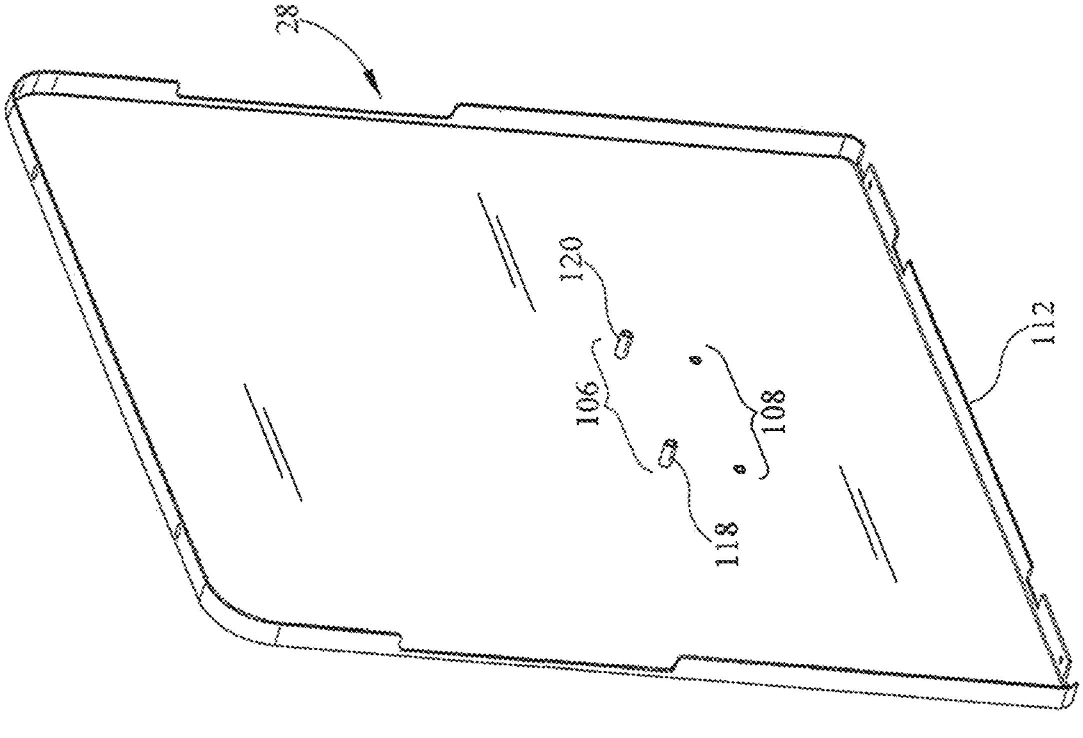
FIG. 17 is a perspective view of the back side of a head deck section of the patient support apparatus with the sensor of FIG. 2 mounted.

Referring to FIG. 17, the sensor 102 is mounted to the head deck 28 by inserting two pegs 118 and 120 through the holes 106 in the head deck 28. The pegs 118 and 120 extend through the deck 28 such that the sensor is secured by the pegs 118 and 120 throughout movement of the head deck 28 between a raised and lowered position. However, the sensor 102 may be easily removed by disengaging the pegs 118 and 120 from the holes 106. If a different location is needed, the sensor 102 can be easily repositioned in the holes 108 or similar holes formed in the fixed seat deck 32.

Figure 18:
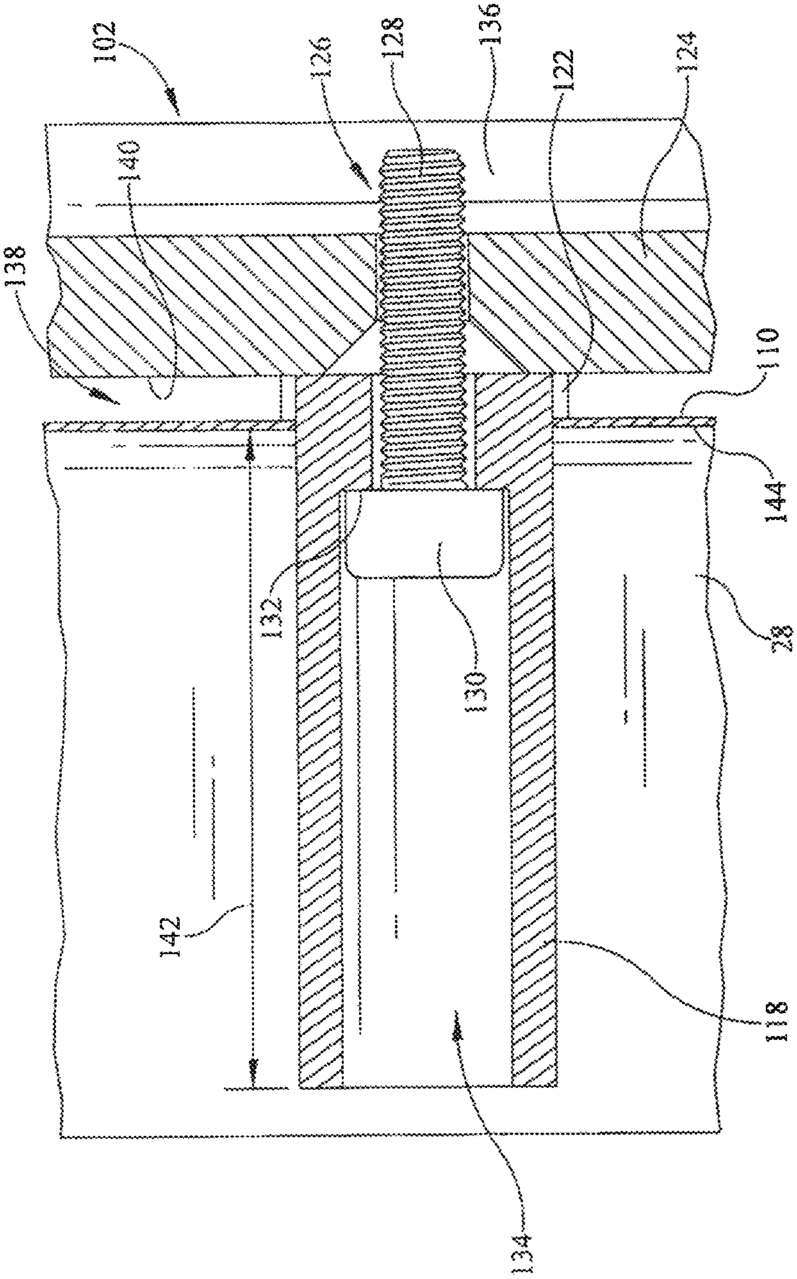
FIG. 18 is a cross-sectional view of the mounting of the sensor of FIG. 2 to the head deck section of the patient support apparatus.

Referring to FIG. 18, the mounting of peg 118 to the sensor 102 is accomplished by a fastener 126 that is secured to a substrate 124 of the sensor 102. The sensor 102 includes a boss 122 that is positioned to receive the peg 118, but be larger than the diameter of the hole the peg 118 is received into such that the boss 122 engages the surface 110 of the head deck 28 and maintains a gap 138 between the surface 110 and a surface 140 of the substrate 124. The fastener 126 includes a threaded shaft 128 that engages a plate 136 of the sensor 102 to secure the peg 118 to the sensor 102. The threads of the threaded shaft 128 do not engage with either the peg 118 or the substrate 124. The peg 118, boss 122, and substrate 124 serve as a mechanical isolation structure to prevent mechanical vibrations from the hospital bed 10 to be transferred through the head deck 28 to the sensor 102. The fastener 126 includes a head 130 that engages an annular surface 132 formed in the peg 118 so that the peg 118 is clamped to the sensor 102. The fastener 126 is received through a cylindrical channel 134 formed in the peg 118. The peg 118 extends a distance 142 past the inner surface 144 of the head deck 28. The length of peg 118 is chosen to permit a user the ability to see the pegs 118 and 120 as they are engaged in either hole 106 or hole 108.

Figure 19:
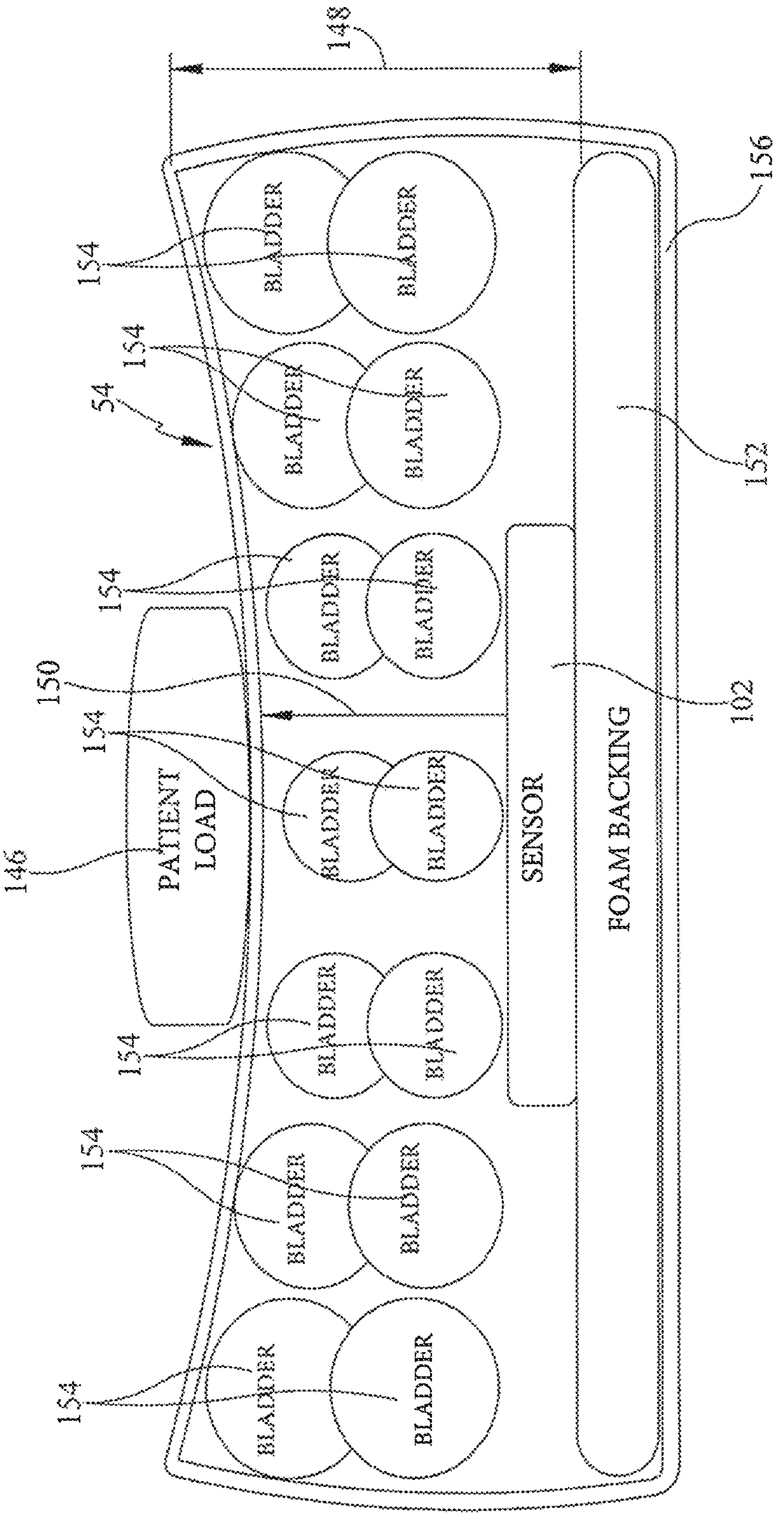
FIG. 19 is a diagrammatic cross-sectional view of a mattress including a sensor for monitoring a patient's vital signs mounted to the interior of the mattress.

In another embodiment shown in FIG. 19, the sensor 102 may be positioned inside of the mattress 54. As a patient load 146 is applied to the mattress 54, the mattress 54 deflects from an original thickness of 148 to a smaller thickness of 150. The sensor 102 is positioned on a foam backing 152 which, along with a group of support bladders 154 of the mattress 54, is encased in a ticking 156. The patient load 146 causes the bladders 154 in the central portion of the mattress 54 to deflect, closing the distance between the patient and the sensor 102. The shorter distance 150 provides for an improved detection of the vital signs being monitored by the sensor 102, improving the accuracy of the data provided by the sensor 102 as compared to embodiments where the sensor 102 must detect the vital signs through the ticking 156 and foam backing 152.

Figure 13:
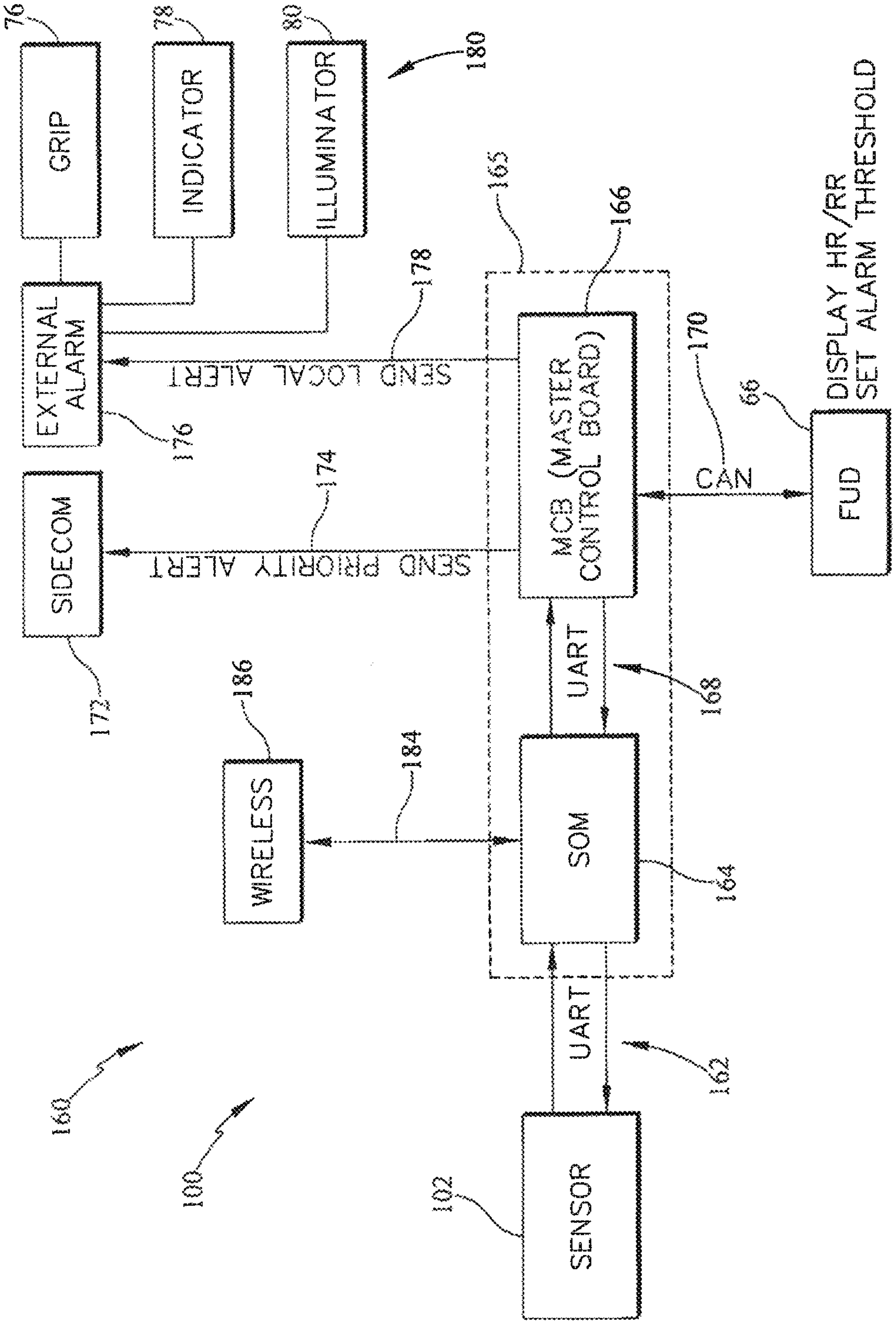
FIG. 13 is a block diagram of a portion of the control system of the patient support apparatus of FIG. 1.
Figure 14:
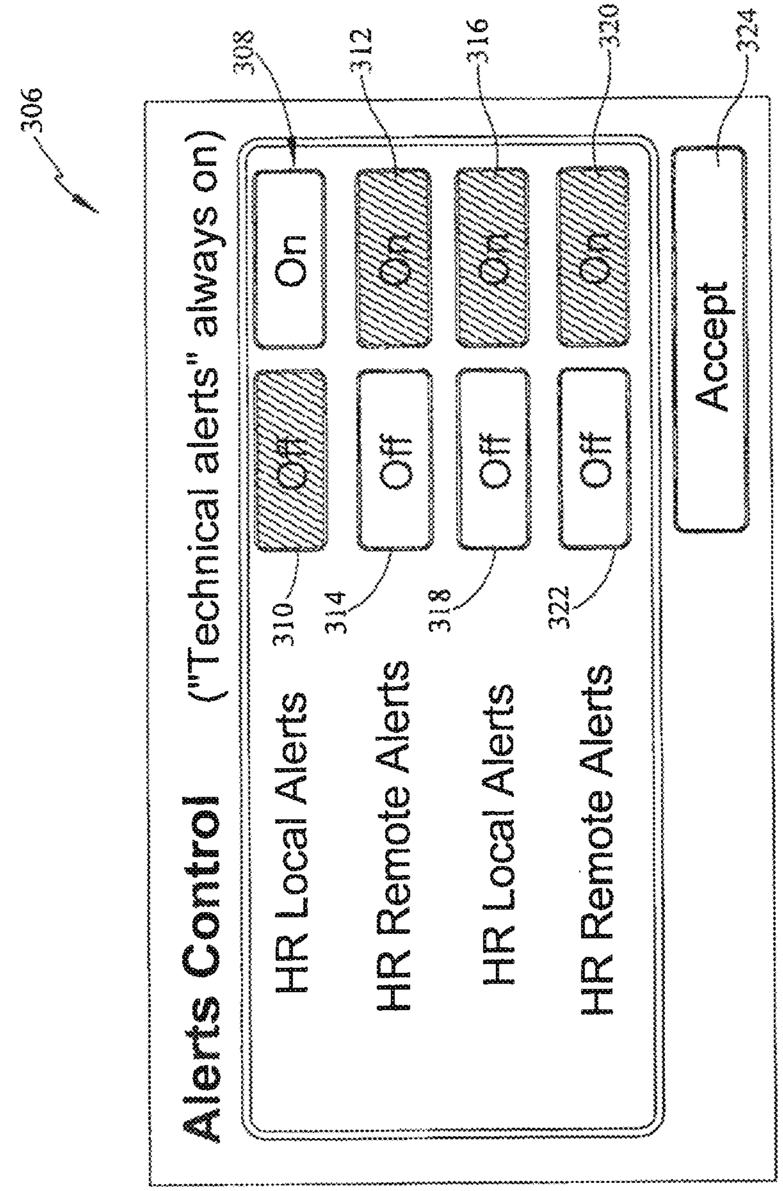
FIG. 14 is a diagrammatic representation of a screen displayed on a graphical user interface of the patient support apparatus.

The sensor 102 is part of a detection and notification system 160 shown diagrammatically in FIG. 13. The detection and notification system 160 may also be operable to monitor other conditions in the hospital bed 10 as disclosed in PCT application WO2016/196403, filed May 29, 2016, titled "PATIENT SUPPORT APPARATUS," and incorporated by reference herein for the disclosure of a structure for monitoring conditions of hospital bed sensors and providing external notifications locally or remotely. The sensor 102 communicates through a UART connection 162 with a system on a module device (SOM) 164. The SOM 164 is connected to and communicates with a master controller (MCB) 166 through a UART connection 168. The SOM 164 and MCB 166 are both part of the bed controller 165 which includes all of the functionality necessary to operate all of the functions of the hospital bed 10. The MCB 166 communicates with the graphical user interface 66 through controller area network (CAN) connection 170. The MCB 166 is also operable to communicate with a communication module (SIDECOM) 172 through a connection 174. The SIDECOM 172 is operable to connect to external systems, such as nurse call systems or other hospital wide communications systems such as the NaviCare® system from Hill-Rom Company, Inc., Batesville, Indiana. This allows information regarding the vital signs detected, including alarm conditions, to be transferred to other locations in the hospital or other facility in which the hospital bed 10 is located.

The MCB 166 also communicates with local external alarms 176 through a connection 178. The connection 178 may be a simple UART interface, a CAN interface, a discrete wiring connection, or any other suitable connection. The external alarm 176 includes the grip 76, an indicator 78, or an illuminator 80. The illuminator 80 is operable to project an image 82 (seen in FIG. 1) onto the floor beneath the foot deck 34. Together, the MCB 166, graphical user interface 66, SIDECOM 172, and external alarm 176 (including the grip 76, indicator 78, and illuminator 80) cooperate to form a notification system 180. Each of the connections 162, 168, 170, 174, 178, and 184 may be a simple UART interface, a CAN interface, a discrete wiring connection, or any other suitable connection as required for the particular application. Relative to the detection and notification system 160, the MCB 166 includes the processor and non-transitory memory required to store instructions and, when appropriate, execute the stored instructions to operate the detection and notification system 160. Some of the processing and instructions may be resident on the SOM 164 as it relates to specific tasks to be executed under the direction of the MCB 166.

The SOM 164 is also operable to perform wireless communications over a link 184 to an external wireless module 186. Any information available from the detection and notification system 160 may be transferred by the SOM 164 over the link 184. In addition, the link 184 may provide for wireless connectivity with the detection and notification system 160 by a user interface device, such as a laptop or tablet computer, for example.

In operation, the notification system 180 is configurable to allow or prevent the illumination capabilities of the grip 76, indicator 78, and/or the illuminator 80. A caregiver may choose to disable the illuminated grips in the notification system 180 when the caregiver determines that the operation of the illuminated grip 76 is unnecessary or would be problematic with a particular patient. Thus, the caregiver can configure the notification system 180 to monitor one or more conditions and provide an indication to a caregiver by illuminating the indicator 78 on the foot deck 34, projecting the 82 image on the floor, and/or illuminating the grip 76. In some embodiments, the illumination of the grip 76 in the amber color may be configured to be based on a different condition, such as the expiration of a time between vital signs checks, or any other condition of which the caregiver might need to be reminded. In addition, the illuminated grip may be illuminated in the amber color if any of the alarm conditions of the hospital bed 10 are active, the amber color providing an indication to the caregiver then alarm condition, or a condition that does not meet a patient's care protocol exists. When either the heart rate or respiration rate is within their respective limits, the notification system 180 displays the image 82 and indicator 78 in a green color. If either the heart rate or respiration rate is outside of an acceptable limit, the notification system 180 displays the image 82 and indicator 78 in a red color. In some embodiments, the notification system 180 displays the image 82 and indicator 78 in an amber color if one of the heart rate or respiration rate are approaching an out of limit condition. In some embodiments, the image 82 and indicator 78 may be flashed in the appropriate respective color. In some embodiments, the illuminator 80 may project an image that coincides with the image on the graphical user interface 66 onto the floor so that a caregiver may be able to see the data in real time at a distance.

Figure 4:
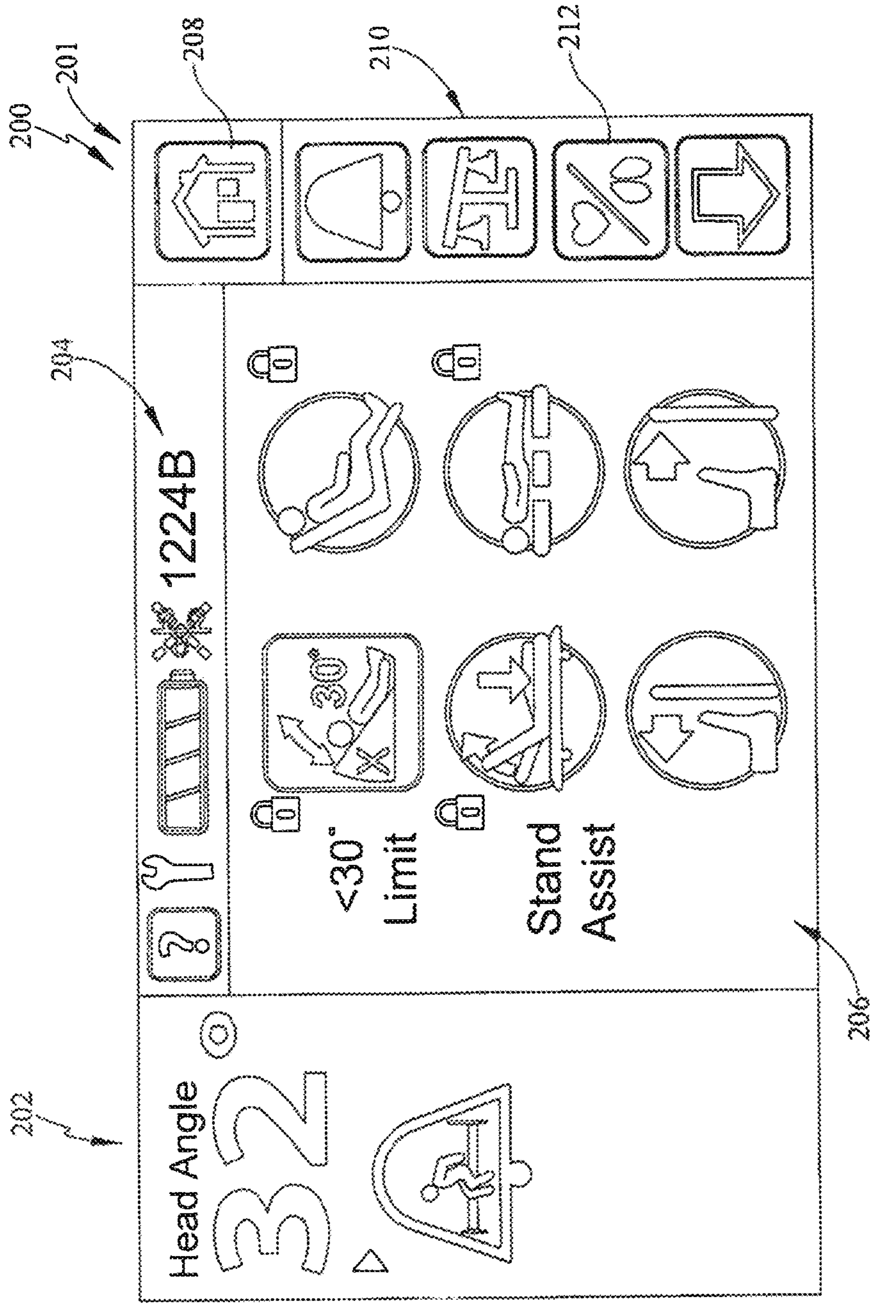
FIGS. 4-11 are diagrammatic representations of screens displayed on a graphical user interface of a patient support apparatus.

Referring to FIG. 4, the graphical user interface 66 displays a touch screen 200 that includes a number of icons which may be selected by a user to control various functions of the hospital bed 10. The functionality of the touch screen 200 is disclosed in the PCT application WO2016/196403, filed May 29, 2016, titled "PATIENT SUPPORT APPARATUS," and incorporated by reference herein for the disclosure of a touch screen menu structure of the hospital bed 10. In addition, prior to activation of the detection and notification system 160, the touch screen 200 displays a home screen 201 of the present embodiment that includes an alarm status section 202, an information bar 204, a function panel 206, a home key 208, and a scrolling menu 210. The scrolling menu 210 includes a vital signs monitoring button icon 212 which, when touched by a user, activates a screen 214 shown in FIG. 20.

Figure 20:
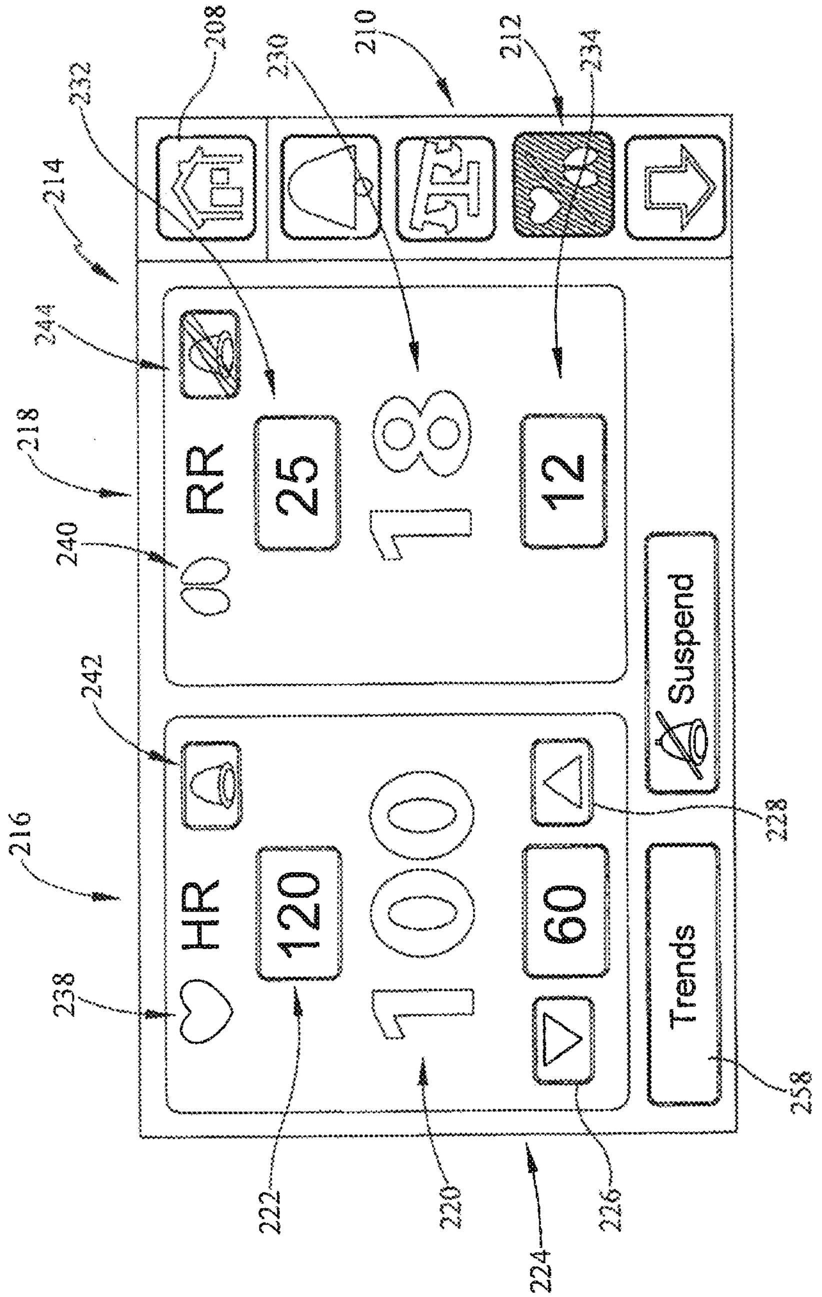
FIGS. 20-27 are diagrammatic representations of screens displayed on a graphical user interface of a patient support apparatus.

As shown in FIG. 20, the activation of button icon 212 causes the button icon 212 to be highlighted to indicate the activation of the functionality of button icon 212. In some embodiments, an additional step may be required with a user being prompted to enter an activation code associated with the detection and notification system 160. In some embodiments, the detection and notification system 160 may be subject to third party approval and activation similar to the approach disclosed in US20140115784A1, filed Mar. 14, 2013, titled "CONTROL SYSTEM FOR PATIENT SUPPORT APPARATUS," which is incorporated in its entirety herein for the disclosure of third party function approval and billing for features of a patient support apparatus. The screen 214 includes a heart rate status portion 216 and a respiration rate status portion 218. As shown in FIG. 20, the heart rate status portion 216 displays the current heart rate 220, an upper heart rate limit 222 and a lower heart rate limit 224. When a user selects one of the upper heart rate limit 222 or lower heart rate limit 224 by touching the respective limit indicator 222 or 224, a pair of arrows 226 and 228 appears as shown next to the lower heart rate limit 224 in FIG. 20. A user selects one of the arrows 226 or 228 to adjust the respective limit 222 or 224 to the appropriate level. After a period with no action, the arrows 226 and 228 disappear. However, if a user selects another limit to be adjusted, the arrows 226 and 228 will disappear from the previous limit being adjusted, and appear next to the current limit being adjusted. For example, a user may adjust the lower heart rate limit 224 and then adjust the upper heart rate limit 222.

The respiration rate status portion 218 includes a current respiration rate detected 230, an upper respiration rate limit 232, and a lower respiration rate limit 234. The upper respiration rate limit 232 and the lower respiration rate limit 234 may be adjusted with arrows 226 and 228 as discussed above with regard to upper heart rate limit 222 and lower heart rate limit 224. The various limits 222, 224, 232, and 234 each represent bound for an alarm condition for the vital signs monitoring system 100. If the current heart rate 220 or current respiration rate 230 are outside of respective limit 222, 224, 232, or 234, the notification system 180 will generate alerts based on the configuration of the alerts within the notification system 180. For example, the alert could include illumination of the grip 76 in a red color and highlighting of the limit that is not being met, along with highlighting the particular parameter.

Figure 21:
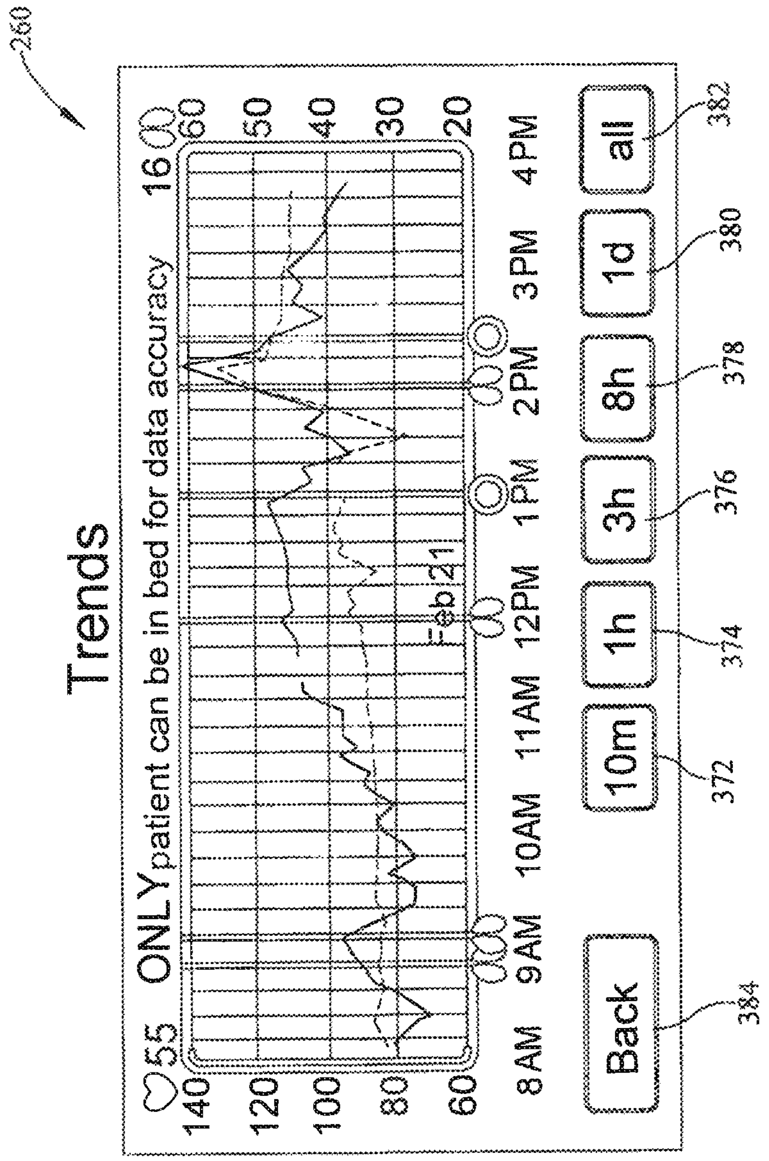

The screen 214 also permits a user to activate a button icon 258 to activate a trends function, showing the history of the patient's heart rate 220 and respiration rate 230. The trends screen 260 shown in FIG. 21 provides a graphical representation of the patient's heart rate 220 and respiration rate 230 along with icons that indicate when the patient's heart rate 220 and respiration rate 230 exceeded an acceptable threshold. The user may change the time scale on the screen 260 by pressing one of the time interval button icons 372, 374, 376, 378, 380, or 382 to show the respective time scale on the screen 260. Once a user is finished reviewing the trend data, activating the back button icon 384 returns the user the previous screen. Referring again to FIG. 20, the user may also temporarily suspend the alarms by activating a button icon 262. The user may then be prompted to confirm the suspension. In some embodiments, the suspension of monitoring lasts for a specific period, such as three minutes, for example. It is contemplated that the data stored and displayed by the trends screen 260 may be transferred off from the bed 10 either wirelessly through the link 184 or by wired connection to the controller 165.

Figure 11:
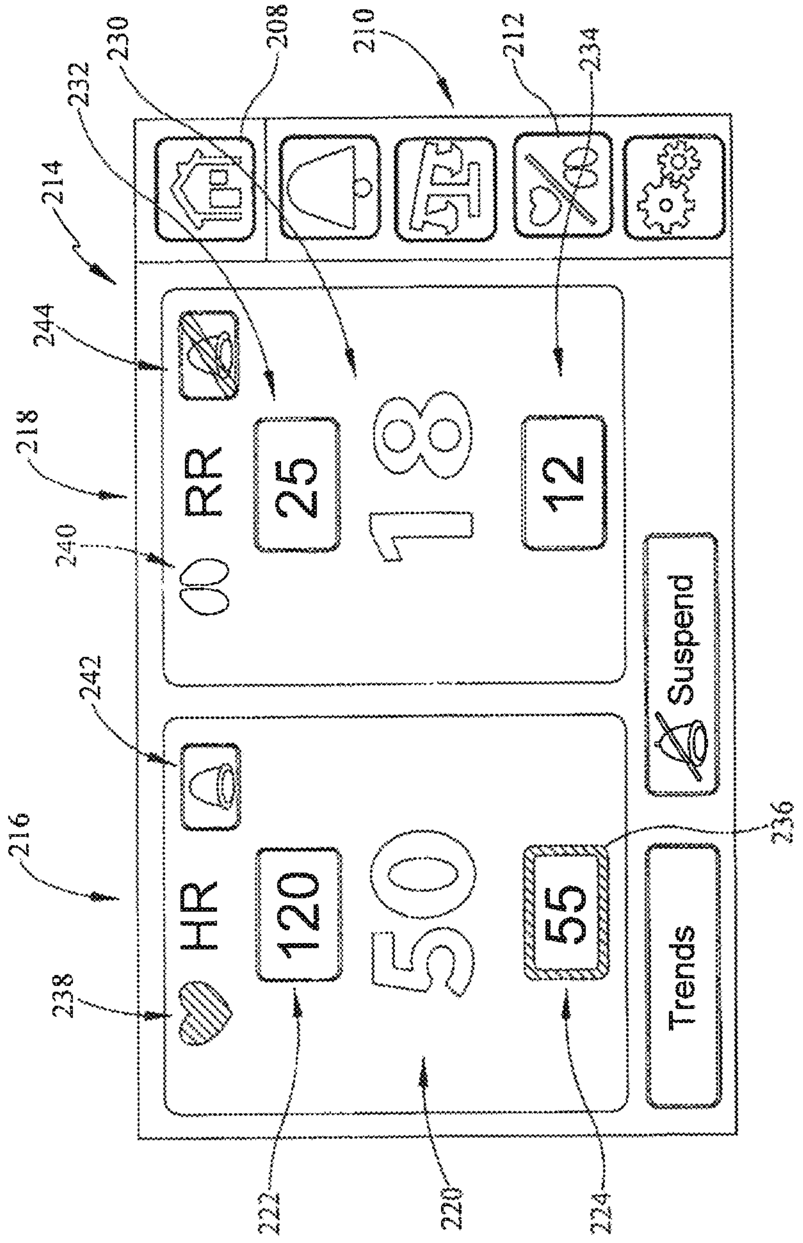

In one example, referring to FIG. 11, when the current heart rate 220 drops below the lower heart rate limit of 55, lower heart rate limit indicator 224 is highlighted as indicated by reference numeral 236 and a heart indicator 238 is highlighted in red. The respiration rate alarm condition is indicated if the lungs icon 240 is highlighted in red. In some embodiments, the user may be permitted to disable an activation of the alarm by activating an alarm icon 242 or 244 on the respective function to be controlled. When the alarm is disabled, it is indicated by a strike through as shown relative to the respiration rate alarm icon 244 in FIGS. 11 and 20.

Figure 5:
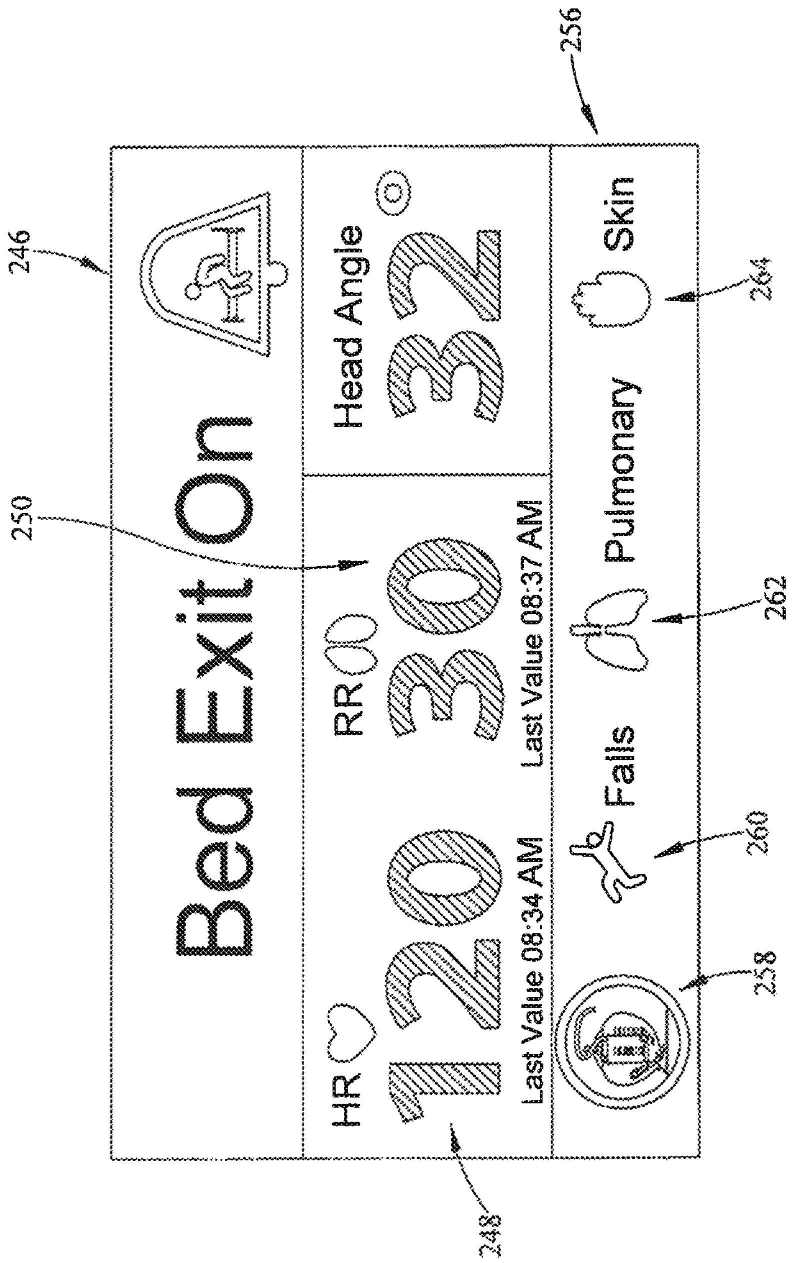

In some embodiments, when the detection and notification system 160 is active and no data is being entered, a status screen 246 is displayed on the graphical user interface 66 as shown in FIG. 5. The status screen 246 combines the status of the detection and notification system 160 and other systems being monitored by the detection and notification system 160. The status screen 246 may be presented as a default screen saver when the graphical user interface 66 is not being used. A risk portion 256 displays various risks that the patient may be susceptible to including a risk related to a Foley bag being present at 258, that the patient is at risk of falling if the patient attempts to leave the bed at 260, that the patient is at risk of developing pulmonary complications at 262, and that the patient is at risk of developing skin injury at 264. It should be noted that the active readings of heart rate 248 and respiration rate 250 are shown darkened in FIG. 5.

Figure 6:
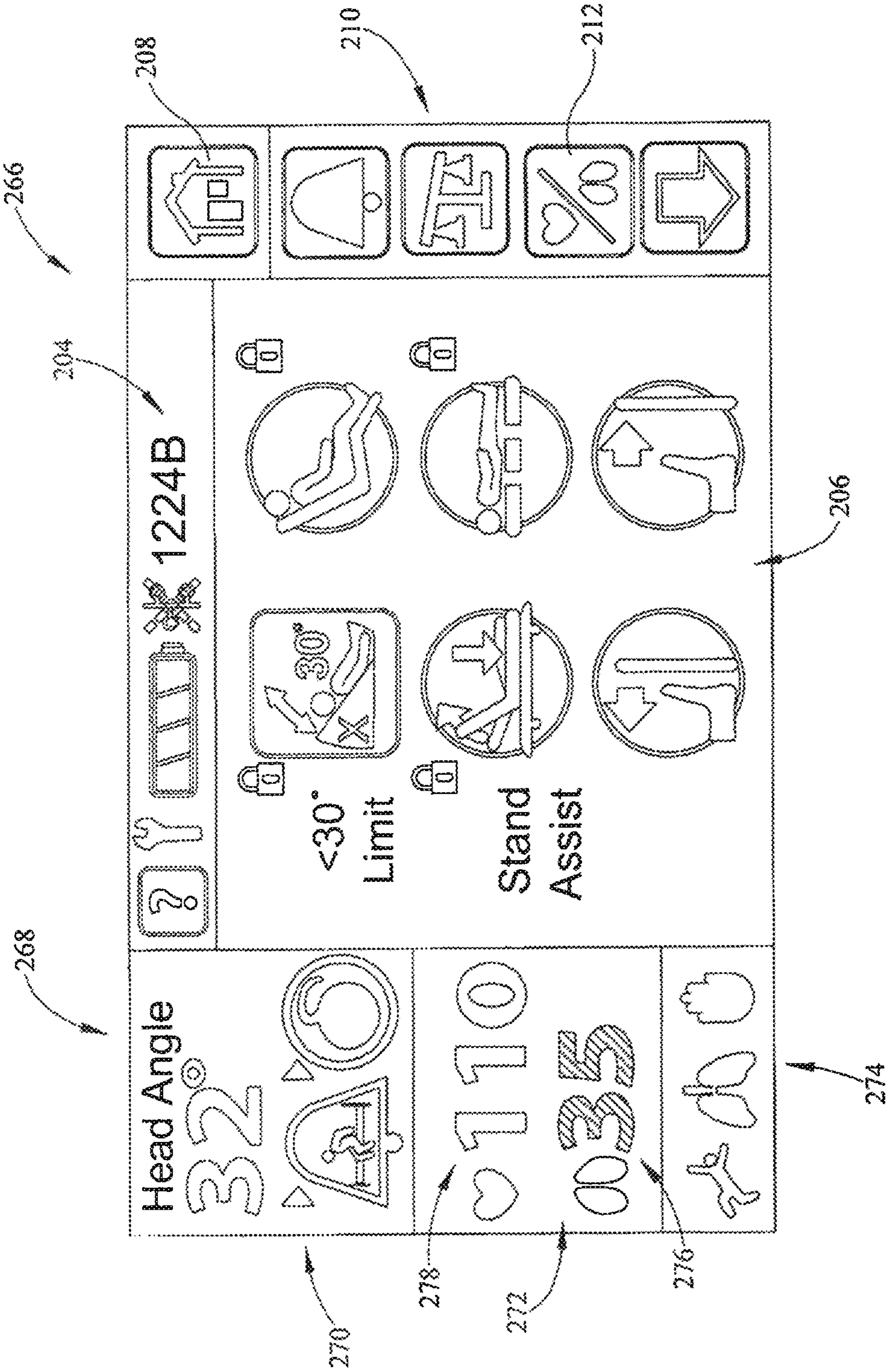
Figure 7:
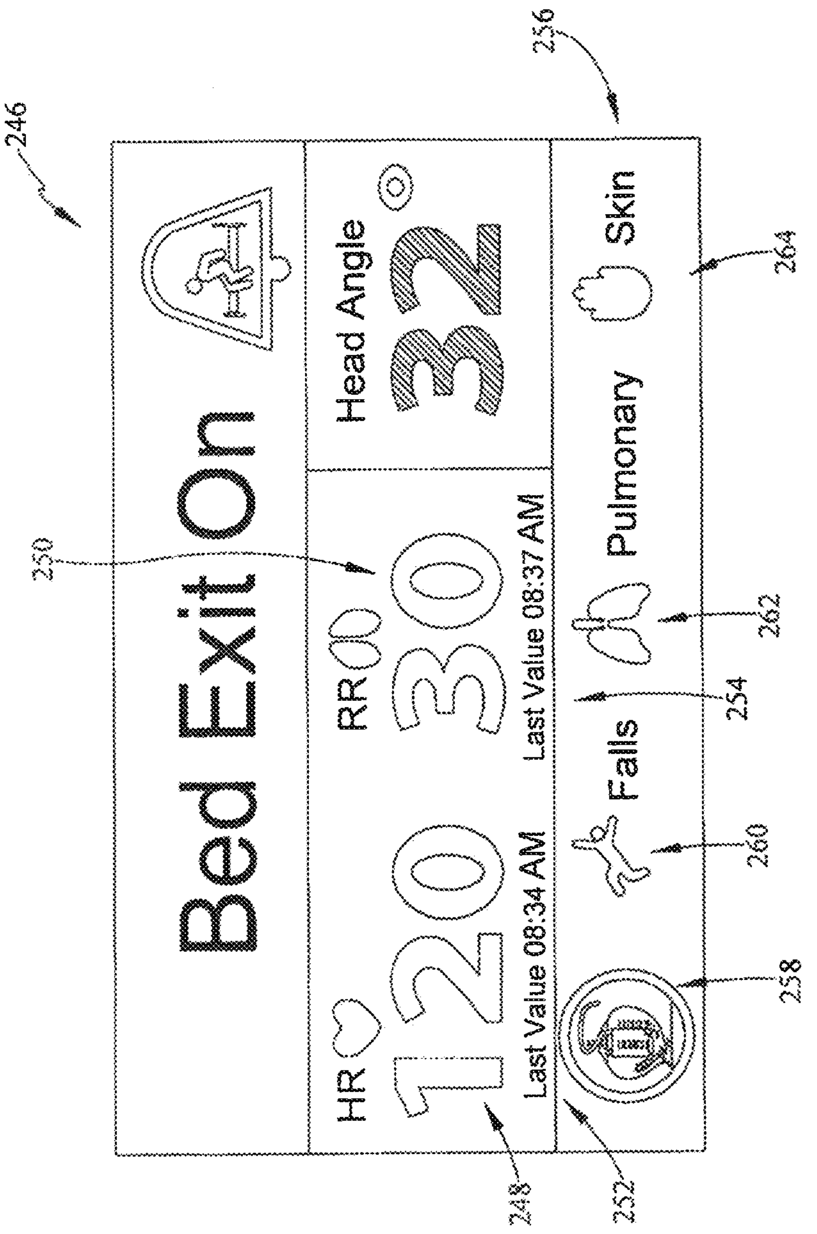
Figure 8:
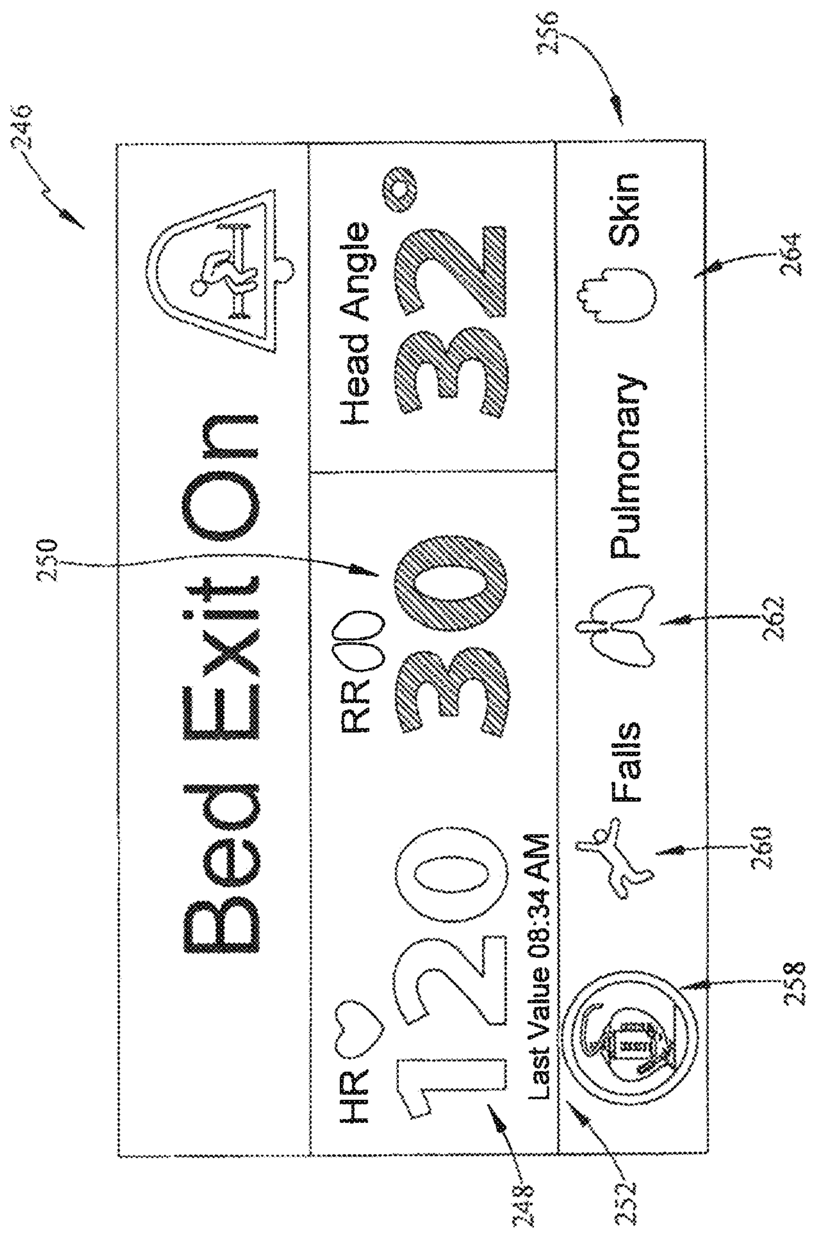

In another embodiment shown in FIG. 6, a screen 266 is displayed on the graphical user interface 66 to provide a user a quick summary of the status of various systems being monitored relative to the hospital bed 10, while also allowing a user to adjust features of the bed 10. In the embodiment of FIG. 6, the portion is 202 shown in FIG. 4 is omitted and replaced with a portion 268. The portion 268 includes a bed status portion 270, a vital signs status portion 272, and a risk status portion 274. In the embodiment of FIG. 6, the heart rate 278 is highlighted or displayed in text that is different from normal, such as the manner in which respiration rate 276 is displayed, when the signal from the sensor 102 is absent or erratic so that a user may quickly identify an issue with the sensor 102 a correct the problem. The use of modifying the color of the text of a displayed value is used in various embodiments for identifying problems with the signal from the sensor 102. For example, the screen 246 is shown in FIG. 7 with the heart rate 248 and respiration rate 250 highlighted to indicate a problem with the sensor 102 reading the respiration rate 250. In the embodiment shown in FIG. 8, the sensor 102 is capable of reading the heart rate 248 as indicated by the normal presentation of the text. However, if the sensor 102 has problems reading both the heart rate and respiration rate, both readings will be highlighted as indicated in display of status screen 246 shown in FIG. 7. When the sensor 102 signal is unavailable, the status screen 246 also provides an indication of the last time that an accurate reading for each of the heart rate 248 and respiration rate 250, at reference numerals 252 and 254 respectively as shown in FIGS. 7 and 8.

Figure 9:
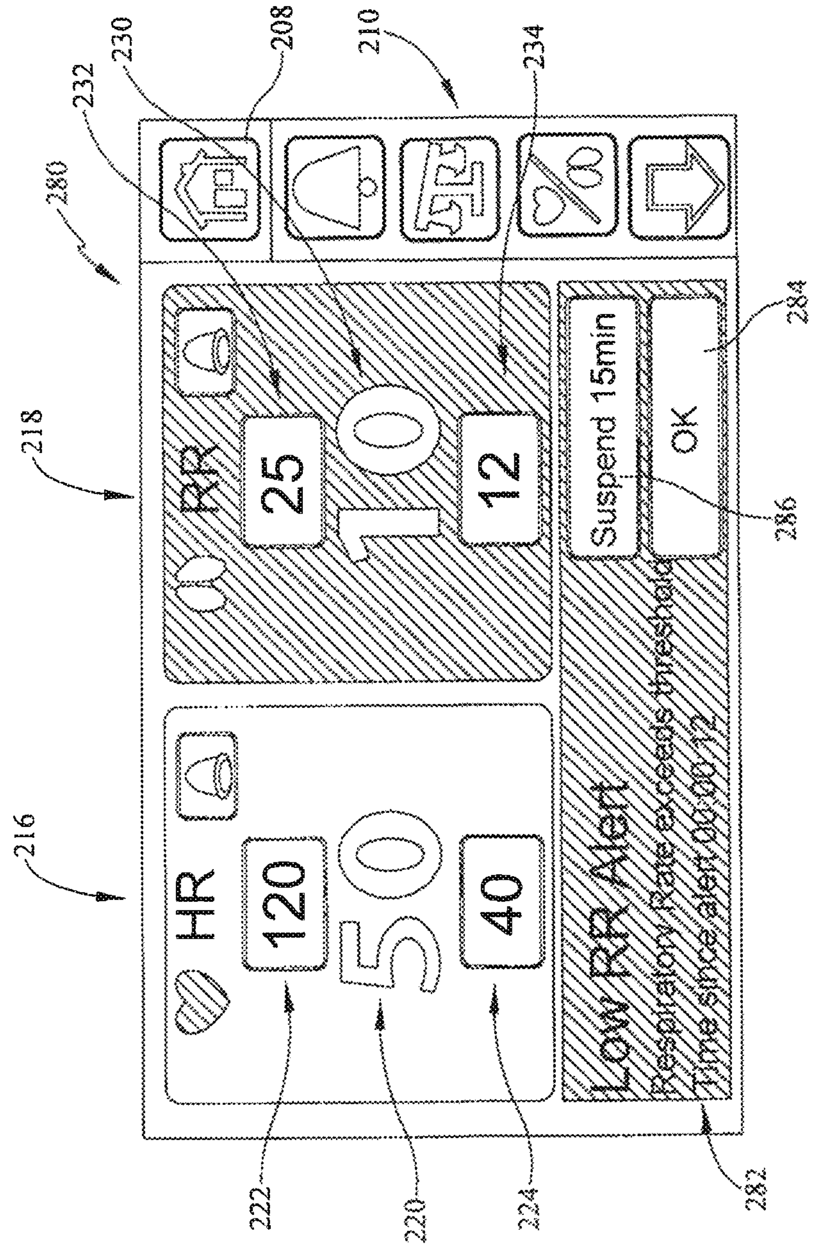
Figure 10:
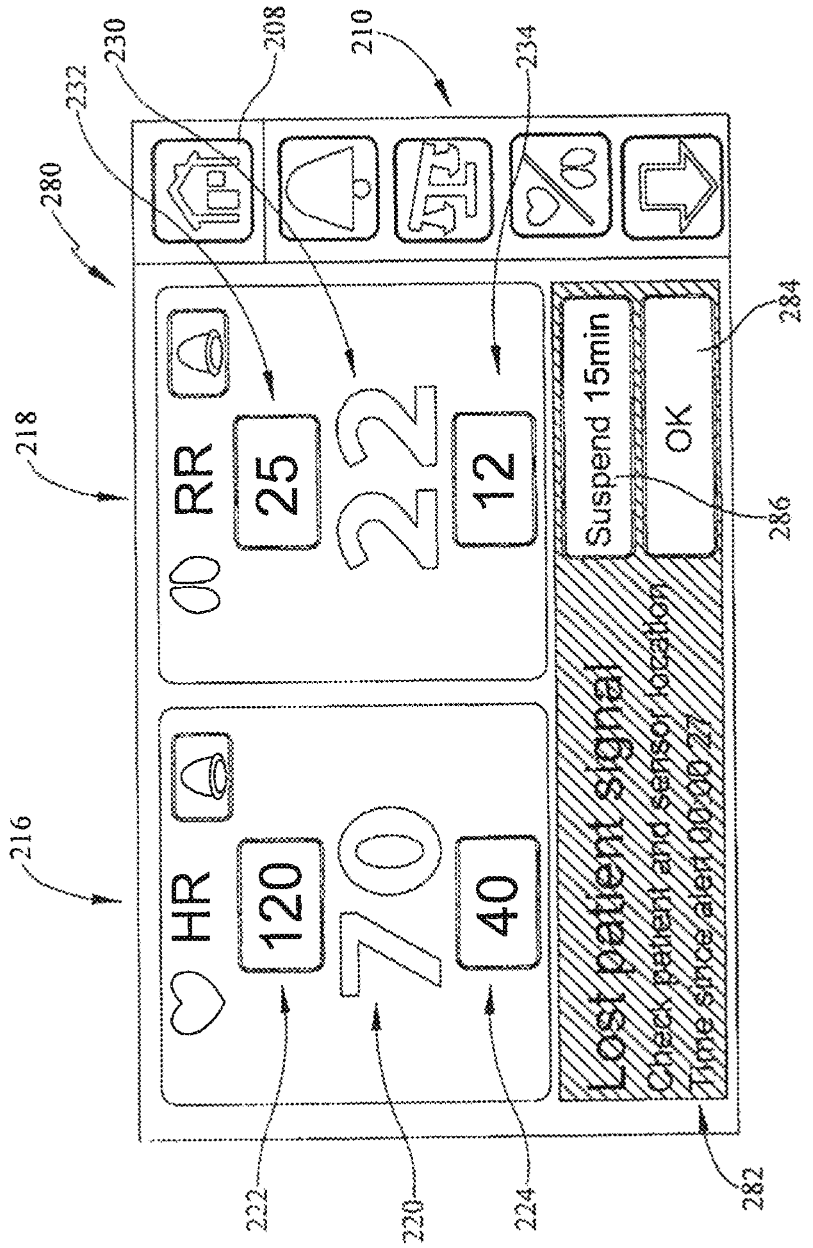

In other embodiments, the status of a patient's heart rate and respiration rate may be the only information displayed, other than the home key 208 and scrolling menu 210. For example, FIG. 9 shows an embodiment of a status screen 280 includes the heart rate status portion 216 and respiration rate status portion 218. As shown in FIG. 9, the respiration rate 230 is below the lower respiration rate limit 234 and an alarm condition exists. The entire portion 218 is highlighted along with a message bar 282 below the heart rate status portion 216 and respiration rate status portion 218. In the embodiment of FIG. 9, the highlighted areas shown in cross-hatch are displayed in red. In other embodiments, other colors may be chosen. The alert message indicating the nature of the alert and the time since the alert was generated is displayed in the message bar 282. The user may suspend the alert for a period of time, 15 minutes, for example, by activating a button icon 286 on the status screen 280. Otherwise, the user may accept the alert by pressing the button icon 284 and addressing the alert. The embodiment of FIG. 10 is similar to the embodiment of FIG. 9, but indicates that a system problem has occurred with the loss of a signal from the patient through a message in the message bar 282.

In some embodiments, the data available from the sensor 102 may be provided externally through the SIDECOM 172 or the wireless link 184 to be added to a patient's medical record in a medical records system. The data may be processed with other patient data to predict the potential for a negative outcome for the patient. The data may be provided through the Hill-Rom Company, Inc. NaviCare® system, for example and used for monitoring and predicting patient outcomes. In one embodiment, the data from sensor 102 may be used as part of the eCART algorithm developed by Quant HC and discussed in Crit Care Med. 2014 April; 42(4):841-8. If a negative outcome is predicted for a patient, the notification system 180 is activated to provide a notification that specifies the particular risk. For example, as shown in FIG. 12, a message 298 may appear at the bottom of a status screen 300 that indicates that the eCART algorithm has predicted a potential negative outcome for the patient, thereby providing a caregiver with an actionable indication of a risk. When such an instance occurs, the message 298 may be accompanied by the activation of grip 76 in a red color along with illumination of the indicator 78 and illuminator 80 to generate a red image 82 on the floor near the bed 10. These elements would apply the currently active alert settings to generate the alert.

In other embodiments, other algorithms may be applied either by the control system of the hospital bed 10, or remotely by a health information system, with the outcome of any alerts generated by an algorithm being generated following the current settings of alerts in the hospital bed 10. For example, a screen 306 is accessible on the graphical user interface 66 to allow a user to choose whether to: turn respiration rate local alerts on 308 or off 310; turn respiration rate remote alerts on 312 or off 314; turn heart rate local alerts on 316 or off 318; and turn heart rate remote alerts on 320 or off 322. The settings set by the user are accepted by activating the button icon 324 to make the settings active.

Figure 30:
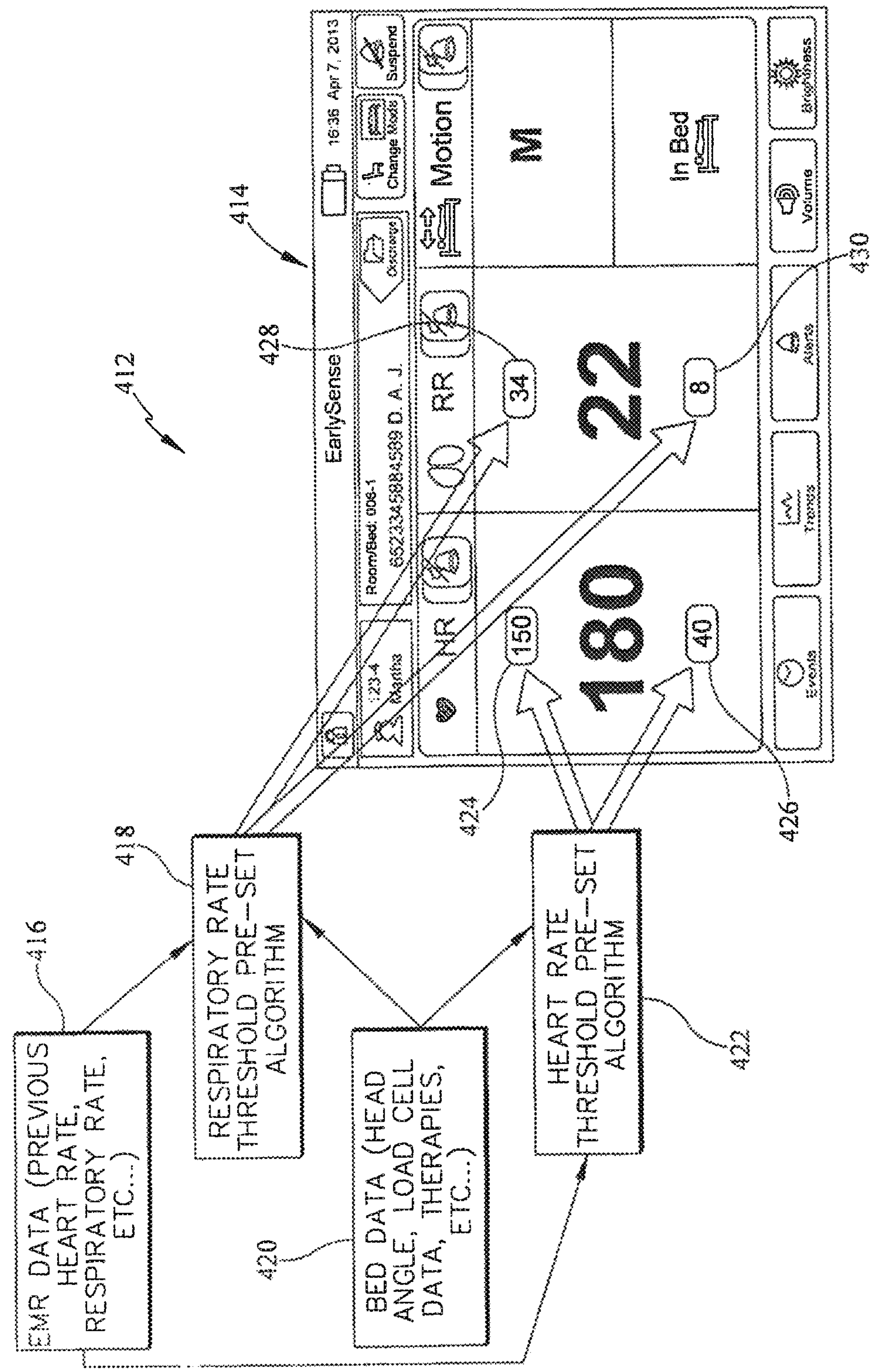
FIG. 30 is a diagrammatic representation of a process by which a heartrate and respiration rate limits for a vital signs monitoring system are automatically set by using information from an electronic medical records system and/or data from the patient support apparatus.

Referring to FIG. 30, in one example a particular patient may be supported on the bed 10 and particular rate limits are determined automatically. For example an upper heart rate limit 424, a lower heart rate limit 426, upper respiration rate limit 428 and lower respiration rate limit 430 may be calculated algorithmically. A process 412 for automatically determining the limits 424, 426, 428, and 430 is shown diagrammatically in FIG. 30. The process 412 includes a separate algorithm 418 for determining the pre-set respiratory rate limits 428 and 430. Similarly, a separate algorithm 422 determines the pre-set heart rate limits 424 and 426. Each of the algorithms 418 and 422 are provided with information external to the bed 10 as represented by process step 416. This information may include historical information relative to the patient such as previous heart rate information or previous respiration rate information. Other information may include particular diagnoses that affect the acceptable rate limits for the particular patient. Still further, the external data may include the time of day or other environmental influences that may cause the acceptable rate limits to be adjusted. In addition, each of the algorithms 418 and 422 are provided with information internal to the bed 10 as represented by process step 420. The information from the bed 10 may include information related to the positions of the various sections of the bed 10, the therapies on the bed 10 that are active, information from the load frame 26 regarding patient location and movement. The load frame 26 of the hospital bed 10 is supported on a set of load cells 330, 332, 334, and 336 (seen in FIG. 15) that provide a signal indicative of the patient load on the bed 10. The signals from the load cells 330, 332, 334, and 336 may be used to determine a patient's total weight and may also be used to discern a location or orientation of a patient on the bed 10. Other sensors may also be present to provide feedback relative to the position of various components of the bed 10. For example, a patient positioned on the bed 10 with a raised head 28 may have a higher heart rate than a patient in fully supine position. The controller 165 utilizes all of this information to determine the appropriate rate limits 424, 426, 428, and 430.

Figure 15:
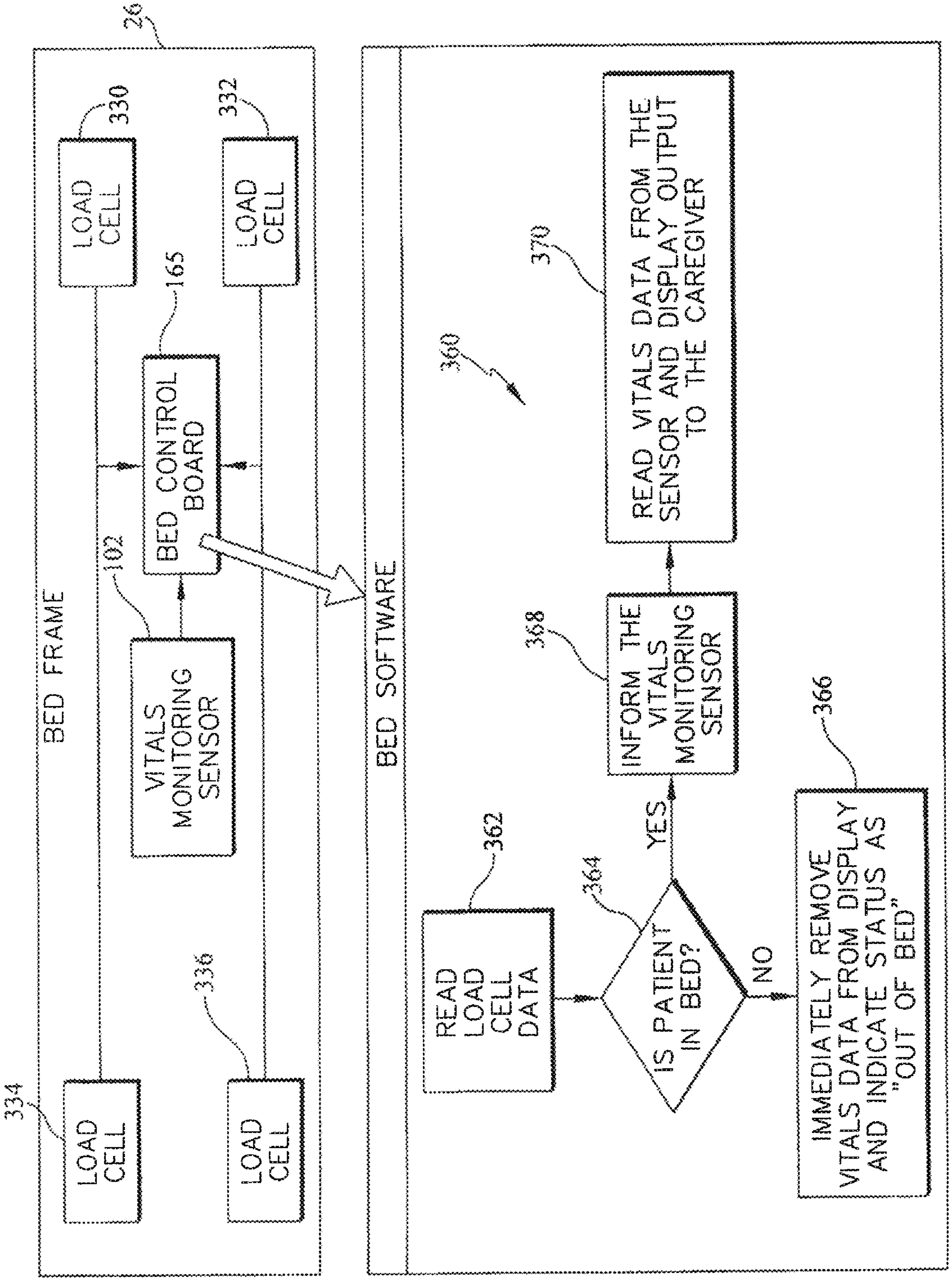
FIG. 15 is a diagrammatic representation of a portion of the patient support apparatus along with a related flowchart.

In an effort to avoid unnecessary alert conditions, detection and notification system 160 utilizes a process 360 shown in FIG. 15 to determine whether an alert condition is warranted. The signals from the load cells 330, 332, 334, and 336 are provided to the bed controller 165 which makes a determination from the signals, using process 360. At process step 362, the controller 165 reads the load cell data. The load cell data is then analyzed at a decision step 364 to determine if a patient is supported on the bed. If the patient is determined not to be in the bed at decision step 364, then the controller 165 proceeds to step 366, overrides the heart rate and respiration rate alert conditions, and provides a message on the graphical user interface 66 that the patient is out of the bed 10. In some cases, the detection and notification system 160 may go into an alert state relative to the patient exiting the bed as disclosed in the earlier mentioned PCT application WO2016/196403. However, alerts related to vital signs would be invalid and, in embodiments where the process 360 is applied, will cause the alerts to be ignored. However, if the patient is determined to be in bed at step 364, the controller 165 proceeds to step 368 and informs the detection and notification system 160 that vital signals are expected from the sensor 102. The process 360 then proceeds to step 370 and the detection and notification system 160 operates normally.

In some embodiments, the controller 165 may determine from the load cells 330, 332, 334, and 336 that a patient is in a particular location on the bed 10. If more than one sensor 102 is present on the bed 10, then the controller 165 may use the information regarding the patient location to discount one or more of the sensor 102 signals to ensure that the best signal is being considered in the determination of the heart rate or respiration rate. In addition, the controller 165 may consider the angle of the head deck 28 in making the determination as to which of multiple sensors 102 should be used in the analysis. For example, if the head deck 28 is raised to an extreme angle, then a sensor 102 positioned in a back section may be discounted or disregarded.

Figure 22:
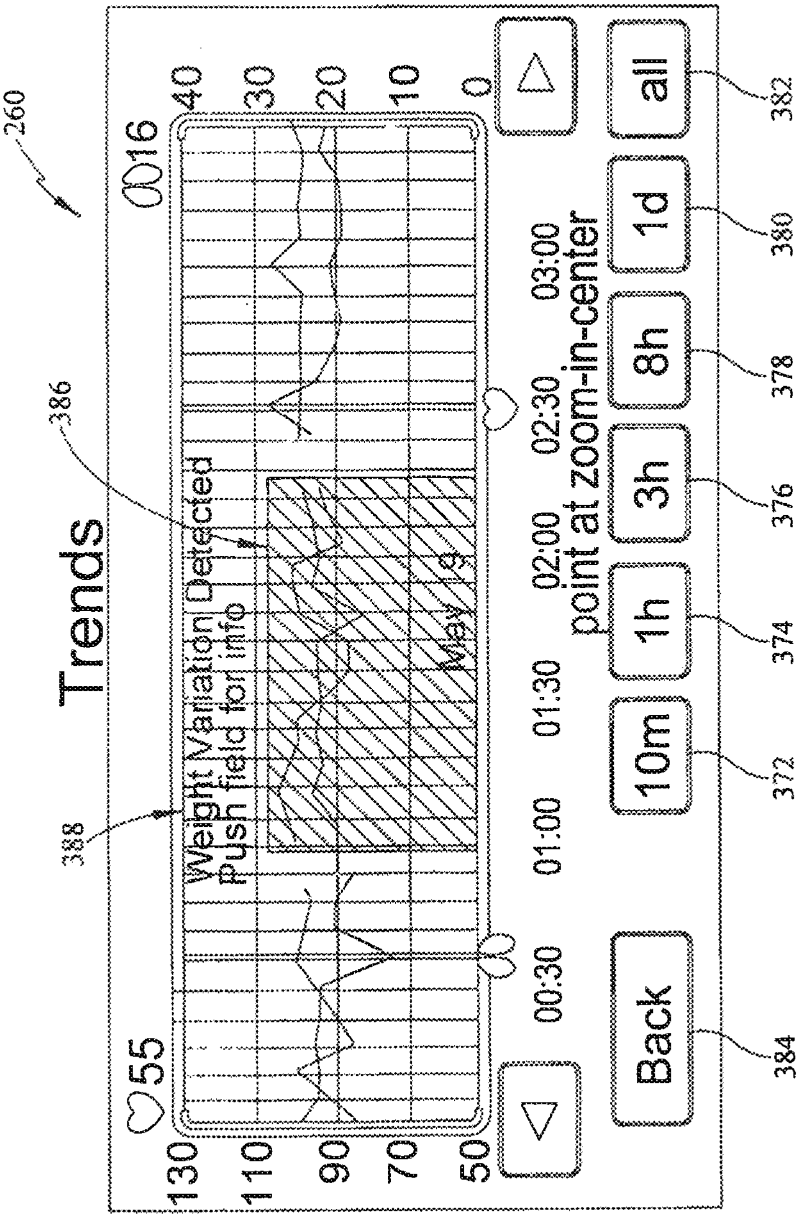
Figure 23:
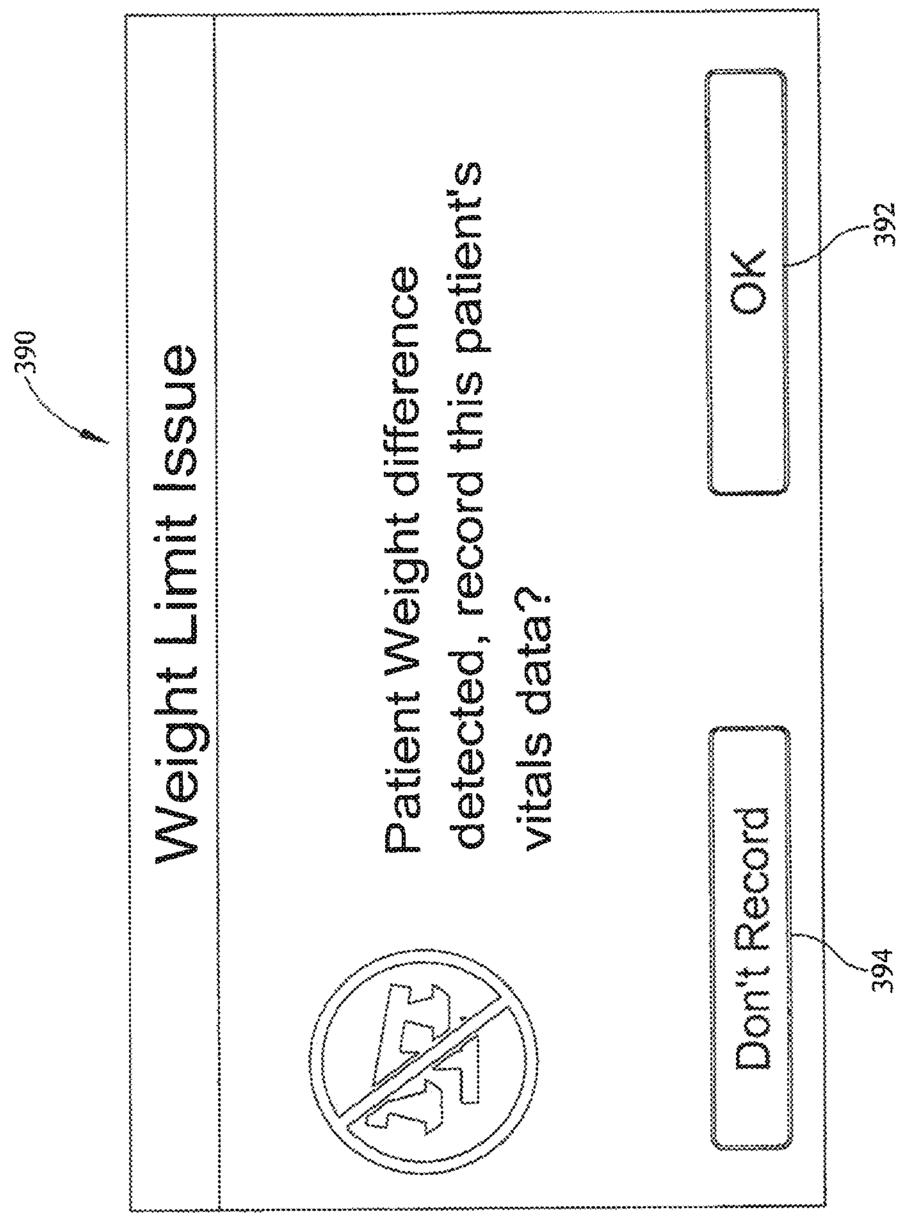
Figure 24:
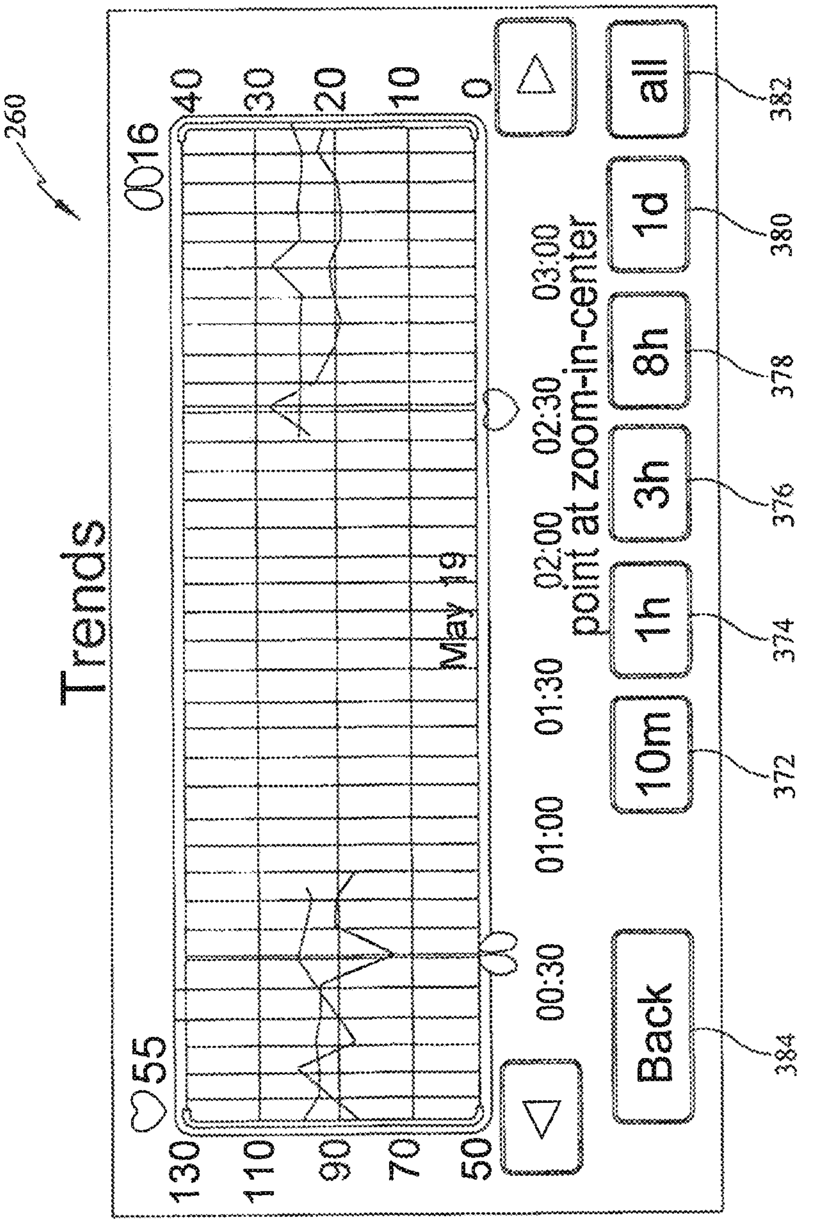
Figure 25:
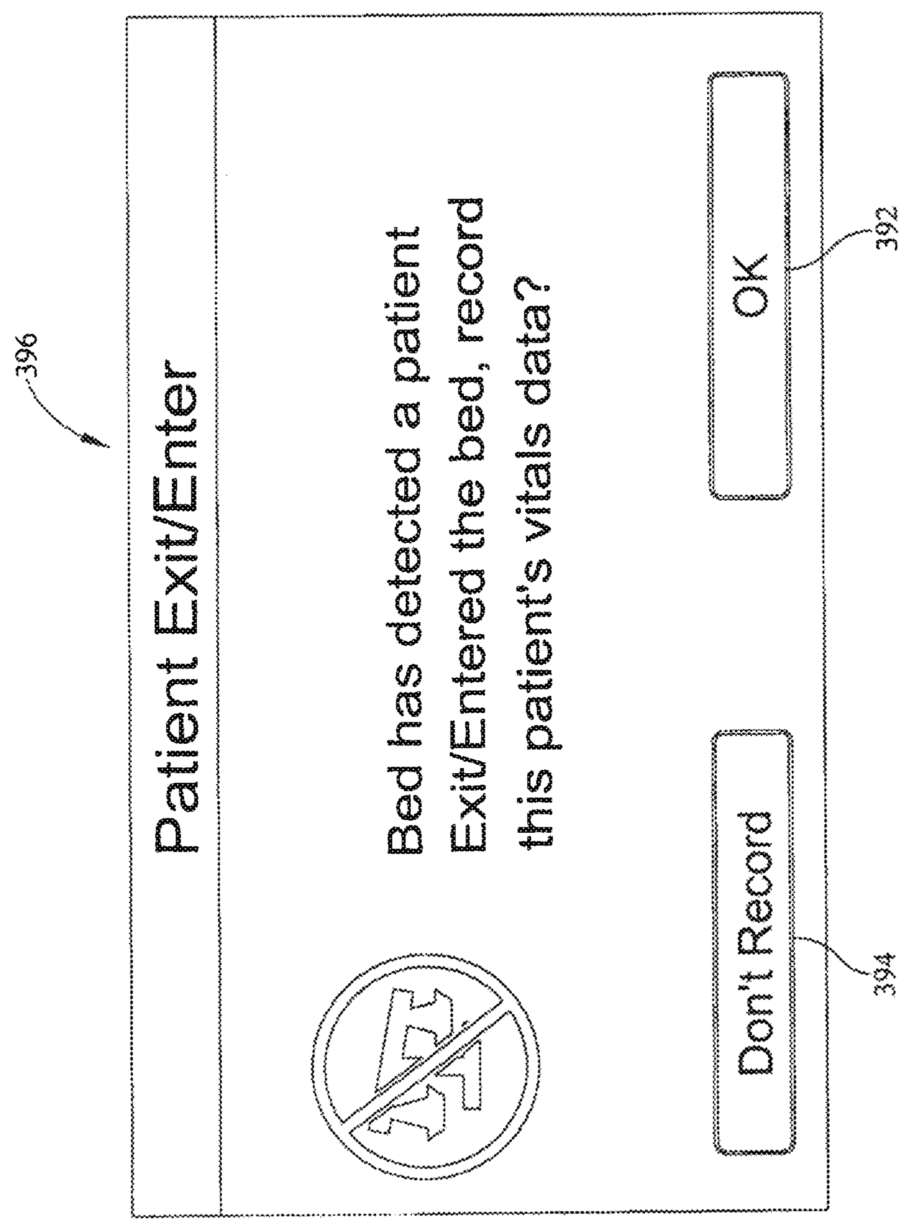

When a condition exists that result in the signal from sensor 102 being of questionable accuracy, the controller 165 signals the detection and notification system 160 of the questionable condition. The range of data that is determined to be suspect is highlighted as suggested by the highlighted range 386 shown in FIG. 22. The range 386 was generated in the embodiment of FIG. 22 by an abnormal weight variation, as suggested by the text prompt 388 in FIG. 22. A user may touch the area of the graphical user interface 66 on which the range 386 appears to address the identified issue. In such a case, the graphical user interface 66 to a prompt screen, such as the screen 390 shown in FIG. 23, that explains the data integrity concern. The user is prompted to either accept the data by touching an "OK" button icon 392 or rejecting the data by touching a "Don't Record" button icon 394. If the "Don't Record" button icon 394 is activated, then the data is deleted from the patient's record as indicated by the trends screen 260 embodiment shown in FIG. 24. In other embodiments, a prompt screen 396, shown in FIG. 24, may be generated if the detection and notification system 160 determines that a patient has exited or entered the bed 10. The user may respond to the prompt of screen 396 by either accepting the data by activating the button icon 392 or rejecting the data by activating the button icon 394. It should be understood that other conditions that cause the data to be of questionable validity may result in other specific prompt screens, similar to prompt screens 390 and 396, may be generated to prompt the user to record or disregard the questionable data.

Figure 31A:
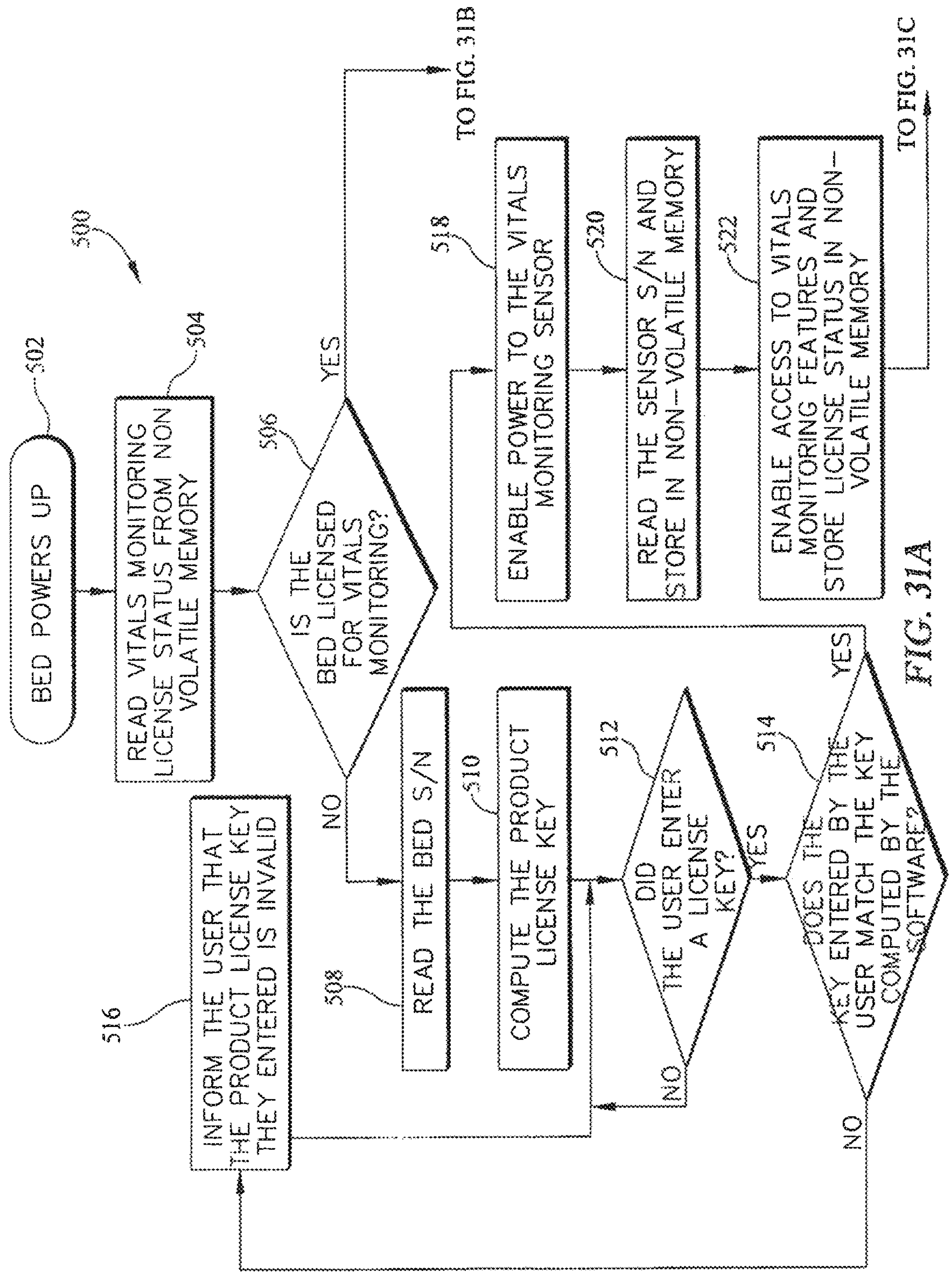
FIG. 31A-31C is a flowchart depicting the process by which the operation of the vital signs monitoring system may be enabled upon start-up or changing of a sensor of the vital signs monitoring system.
Figure 31B:
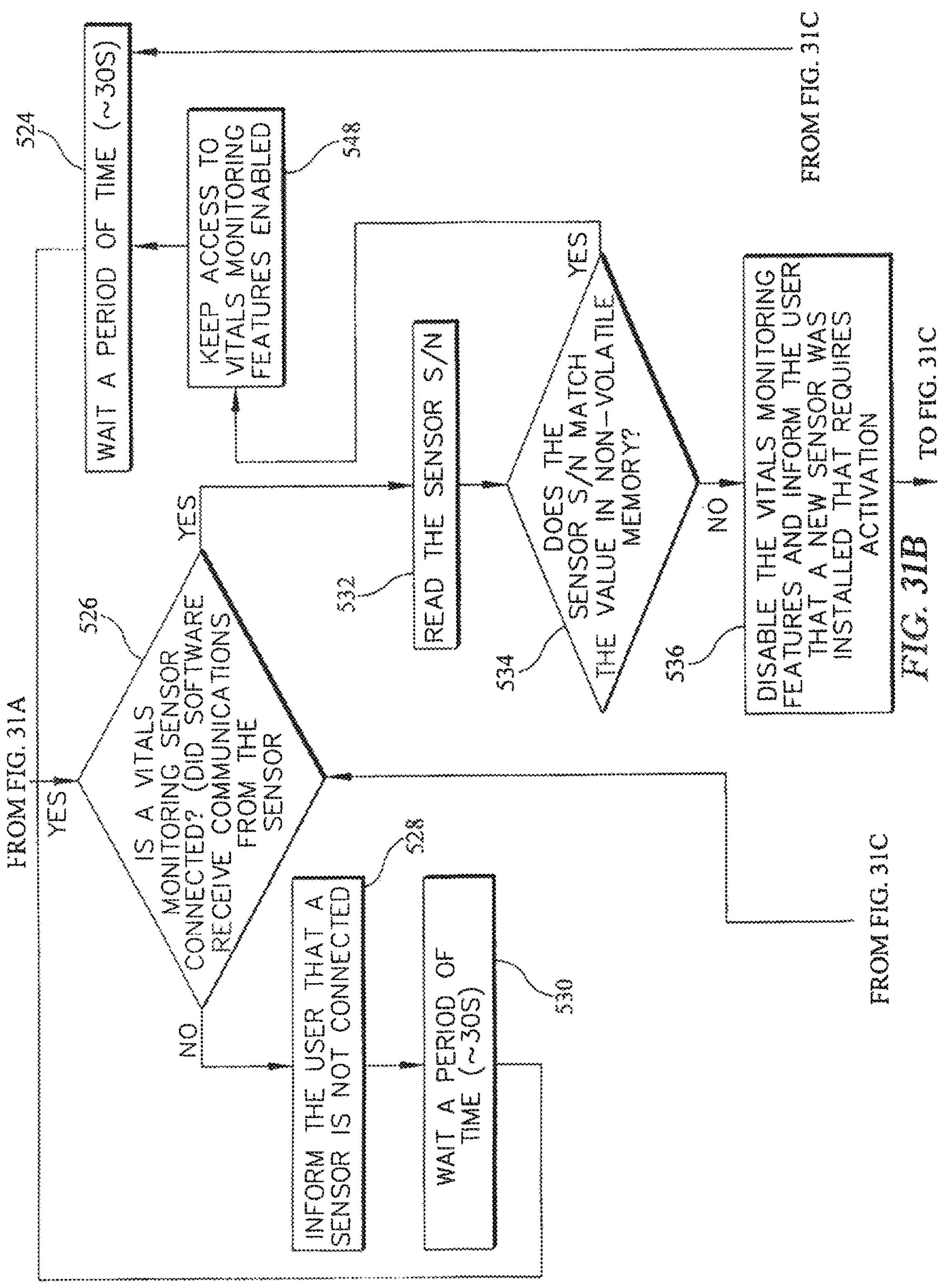
Figure 31C:
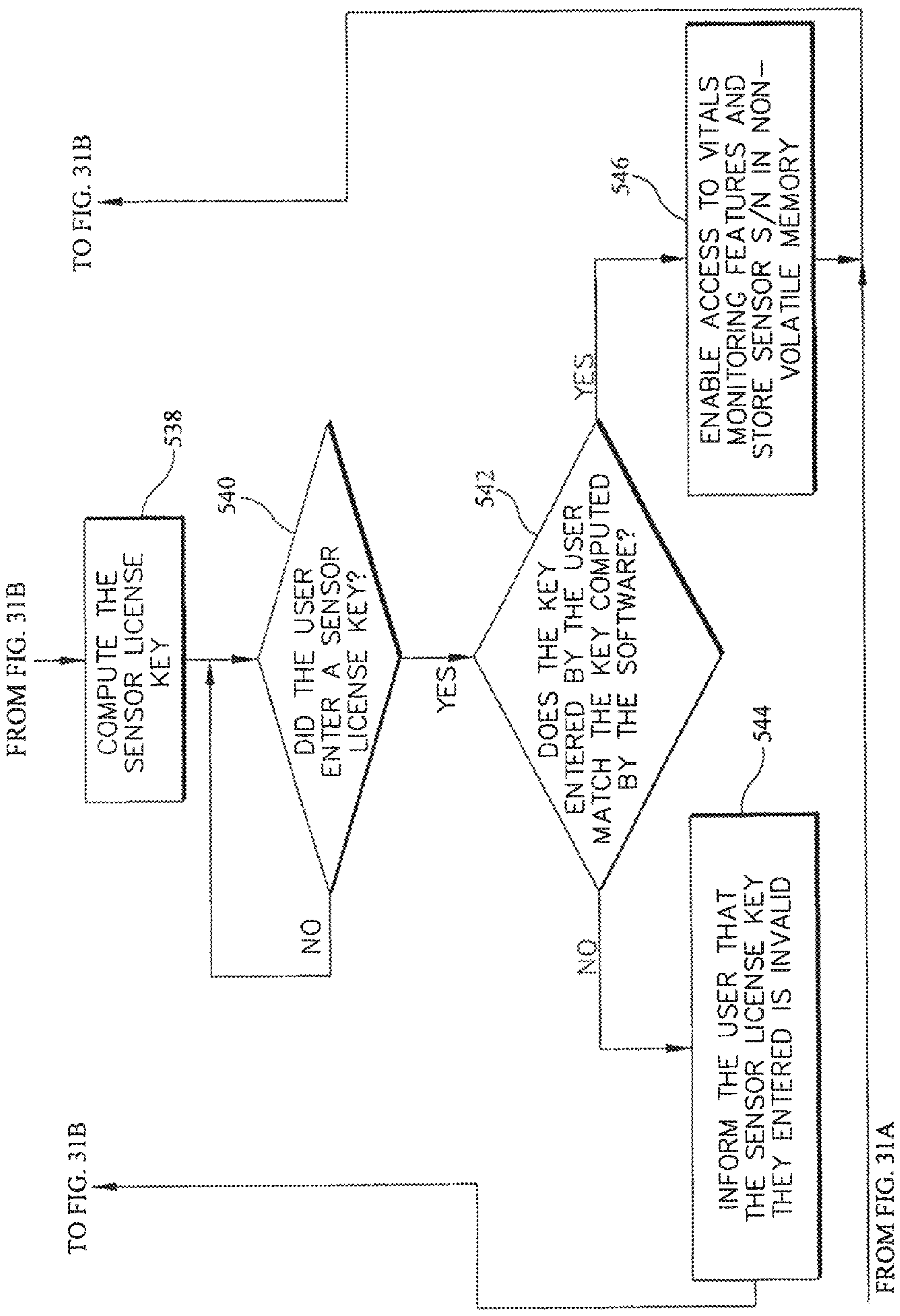

The hospital bed 10 is functional without the sensor 102 and the lack of the presence of a sensor 102 will result in the controller 165 operating the graphical user interface 66 without reference to the vital signs monitoring system 100. In other words, the button icon 212 will be omitted from the scrolling menu 210. If a sensor 102 is added to a hospital bed 10, a process 500 shown in FIGS. 31A-31C is executed by the controller 165 to confirm that the user has the right to use the sensor 102 and vital signs monitoring system 100. The process 500 begins at process step 502 when the bed powers up. Upon powering up, the controller 165 reads the license status of the vital signs monitoring system 100 from a non-volatile memory location at process step 504. At decision step 506, the controller 165 determines whether the bed is licensed for the operation of the vital signs monitoring system 100. If the bed 10 is properly licensed for the vital signs monitoring system 100, then the process 500 proceeds to step 526 on FIG. 31B as will be discussed in further detail below. If the bed 10 is not licensed for use of vital signs monitoring system 100, the controller 165 proceeds to process step 508 where the controller 165 reads the bed's serial number stored in a non-volatile memory location. Once the serial number is read, the controller 165 proceeds to process step 510 and computes the product license key for activation of the vital signs monitoring system 100. The license key at step 510 is calculated based, in part, on the bed serial number.

Figure 26:
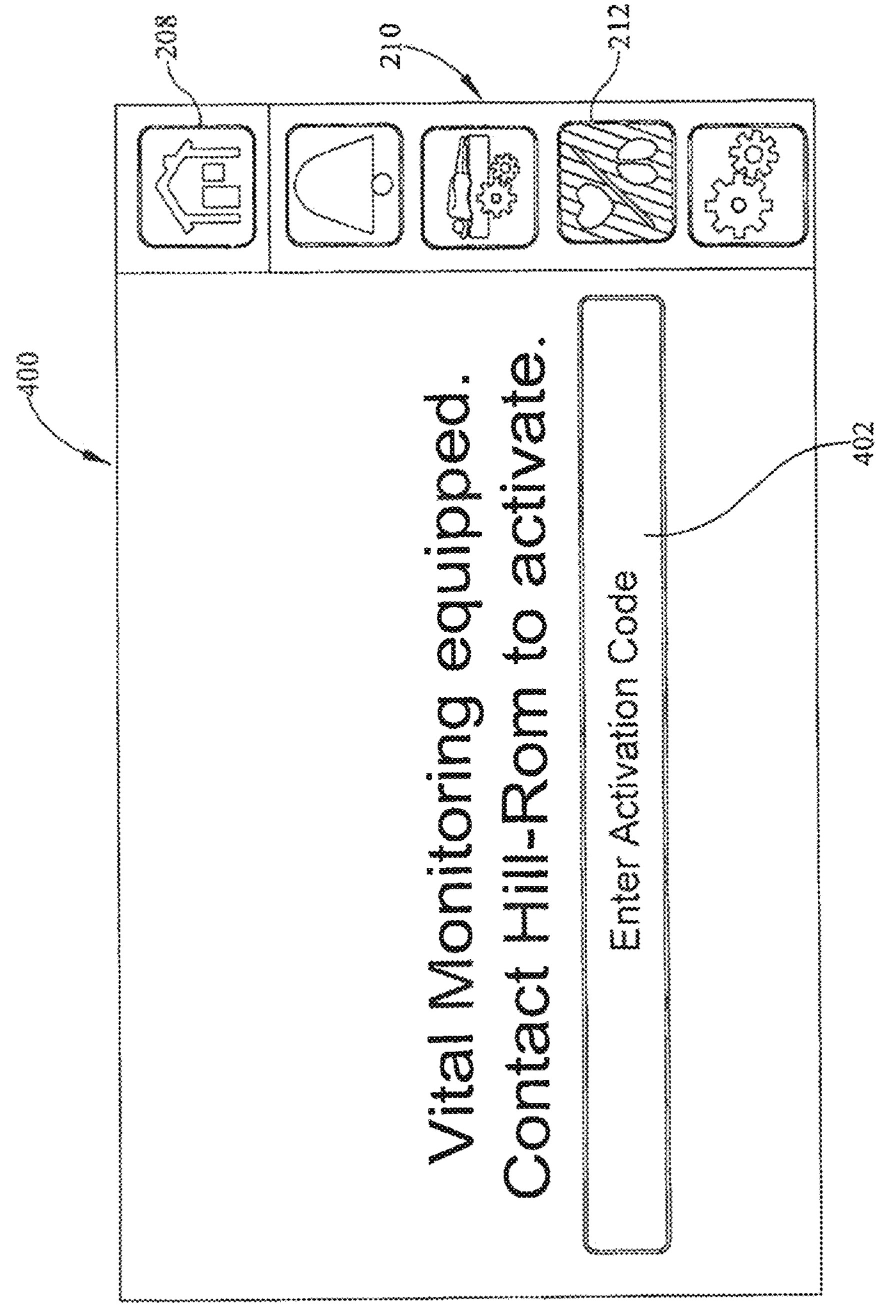
Figure 27:
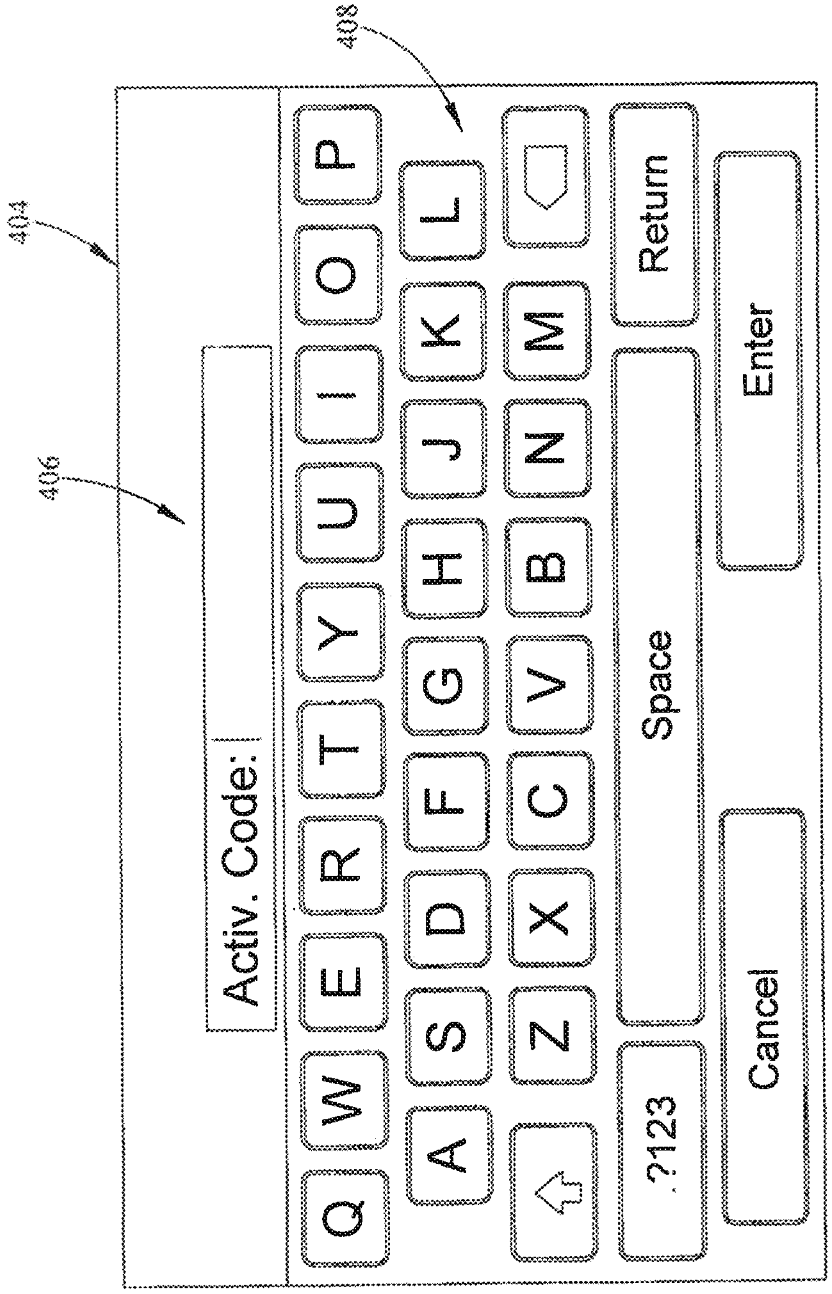
Figure 28:
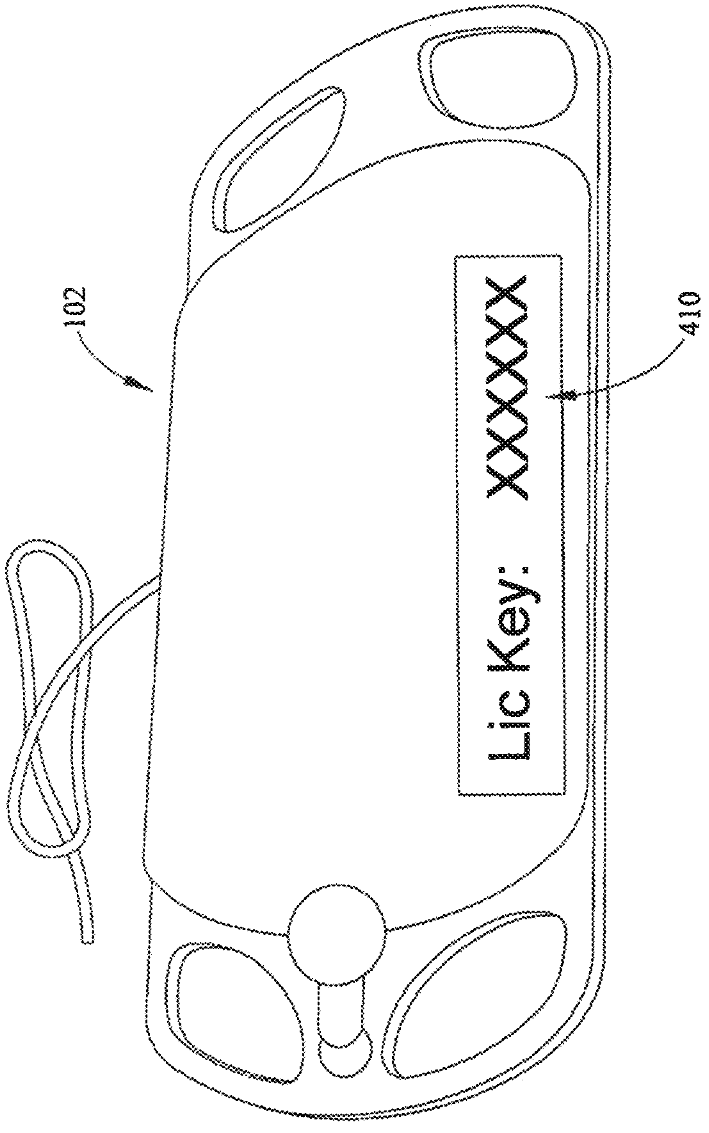
FIG. 28 is a perspective view of the back of the sensor of FIG. 2.
Figure 29:
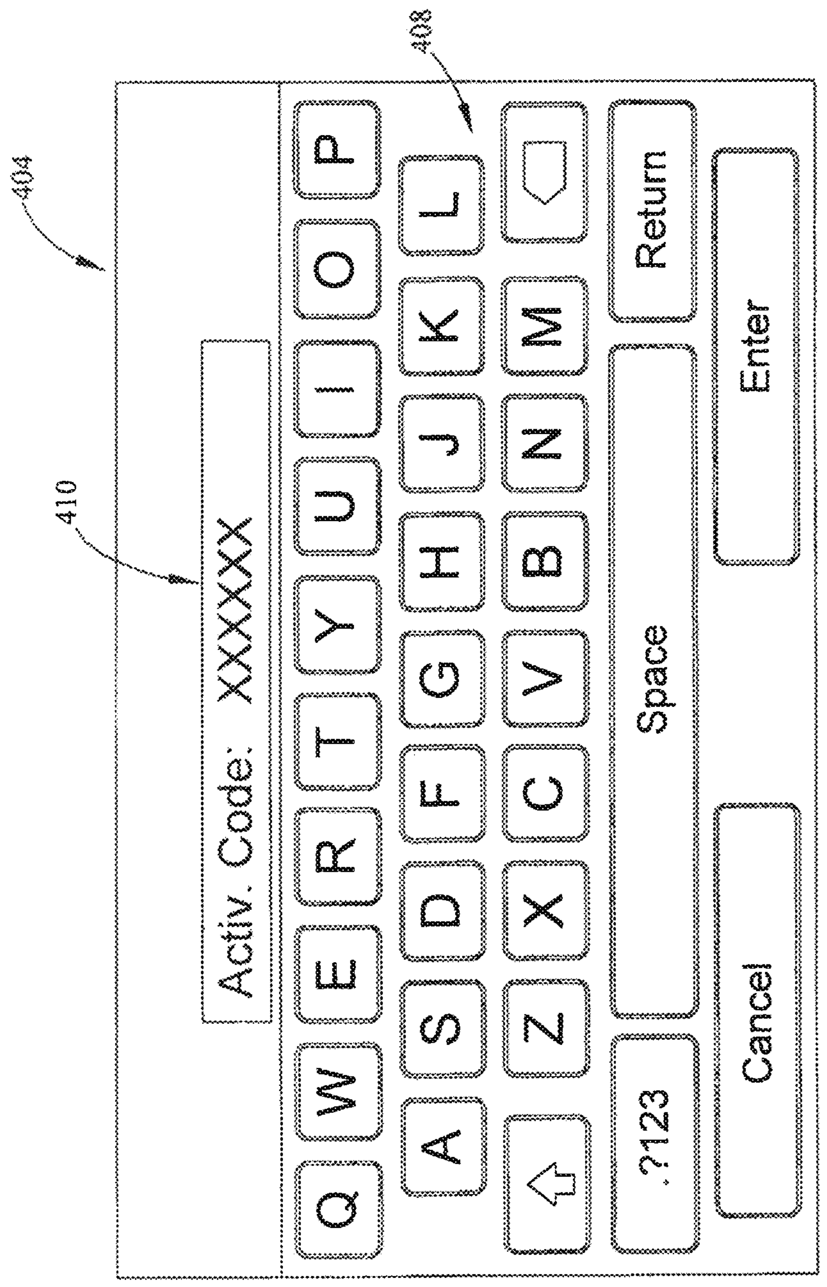
FIG. 29 is a diagrammatic representation of a screen displayed on a graphical user interface of a patient support apparatus, the screen useable by a user to enter a license key for the sensor of FIG. 2.

At decision step 512, the controller 165 monitors for the entry of a license key by a user. The user is prompted by a prompt screen 400 shown in FIG. 26. The user may proceed to enter an activation code by touching the "Enter Activation Code" icon button icon 402 which causes the display to proceed to screen 404 shown in FIG. 27. The user is presented with a QWERTY interface with an entry line 406. The user refers to the license key 410 on sensor 102, as shown in FIG. 28. Once the code is entered as shown in FIG. 29, the user activates the enter key on the QWERTY keyboard 408. If no key is entered, the screen 400 continues to be displayed and the controller 165 loops the decision step 512 until a license key/activation code 410 is entered.

Once the license key is entered, the process 500 proceeds to decision step 514 where the key entered is compared to the key computed at step 510. If the entered key does not match the key calculated at step 510, the controller proceeds to step 516, informs the user the key is invalid and continues to monitor for the entry of a new key at step 512.

If at decision step 514 the key entered matches the key calculated at step 510, the process 500 advances to step 518 and the sensor 102 is powered up. The process proceeds to step 520 and the sensor serial number is stored in non-volatile memory. The process 500 then proceeds to process step 522 and updates the graphical user interface 66 to display the capabilities of the vital signs monitoring system 100 and stores the positive license status in non-volatile memory. The process 500 then proceeds to step 524 shown in FIG. 31B where the controller 165 waits for thirty seconds. The controller 165 then proceeds with process 500 to the decision step 526 on FIG. 31B.

At decision step 526, the controller 165 confirms whether there is a sensor 102 active within the vital signs monitoring system 100. If there is no sensor 102 connected, the process 500 advances to step 528 and prompts the user that there is no sensor 102 connected. The controller 165 then waits for a period of thirty seconds as indicated by process step 530. The process 500 then returns to decision step 526 and the controller 165 evaluates again whether a sensor 102 is connected within the vital signs monitoring system 100. If a sensor 102 is determined to be connected at step 526, then the controller 165 proceeds to process step 532 and reads the serial number of the sensor 102 that is connected. The controller 165 then compares the serial number of the sensor 102 to the sensor serial number previously stored in non-volatile memory at decision step 534. If the detected serial number matches the stored serial number, then the controller 165 continues to operate the vital signs monitoring system 100 as indicated by process step 548.

If the detected serial number does not match the stored serial number, then the controller 165 disables the vital signs monitoring system 100 and prompts the user that the sensor 102 that is connected needs to be activated as indicated by process step 536 in FIG. 31B. The process 500 then proceeds to step 538 on FIG. 31C and computes a license key based, at least in part, on the serial number of the connected sensor 102. The process 500 proceeds to decision step 540 and looks for the user to enter a license key as discussed above. If a license key is entered, the process 500 proceeds to decision step 542 and the controller 165 determines whether the license key that has been entered matches the license key computed by the controller 165. If it does, the process 500 advances to process step 546 and enables the vital signs monitoring system 100.

If the entered license key does not match the computed license key at decision step 542, then the controller informs the user that the license key is invalid as indicated by process step 544. The process then proceeds to decision step 526 to loop through the process 500, looking for a different sensor 102 or for the user to enter the correct license key.

In the embodiment discussed above, an appropriate activation/license key may be based on either the bed serial number or the serial number of the particular sensor 102. It is contemplated that a user will pay a fee for the activation key for a particular sensor 102 or bed 10 with a sensor 102 combination. However, in some embodiments, the activation of the vital signs monitoring system 100 may be limited and licensed to a particular combination of bed 10 and sensor 102 such that users may not be permitted to move sensors 102 between beds 10, without prior authorization. In such a case, the activation/license key computed by the controller 165 may rely on both the serial number of the bed 10 and the serial number of the sensor 102 so that a user must enter a particular activation code that is good for only the combination of sensor 102 and bed 10. This is contemplated to prevent mis-use of the sensors 102 when they are beyond their useful life, or the use of unauthorized sensors 102 which may not be of sufficient quality. For example, the controller 165 may perform a standard, but confidential, algorithm on one or the other of the serial numbers of the bed 10 or sensor 102 to calculate a value of a license key. In other embodiments, the serial numbers of both the bed 10 and sensor 102 may be independent variables in a confidential equation that calculates a particular license key that is unique to the combination. In embodiments where multiple sensors 102 are present, the activation/licensing analysis may be completed for each of the multiple sensors 102.

Figure 32:
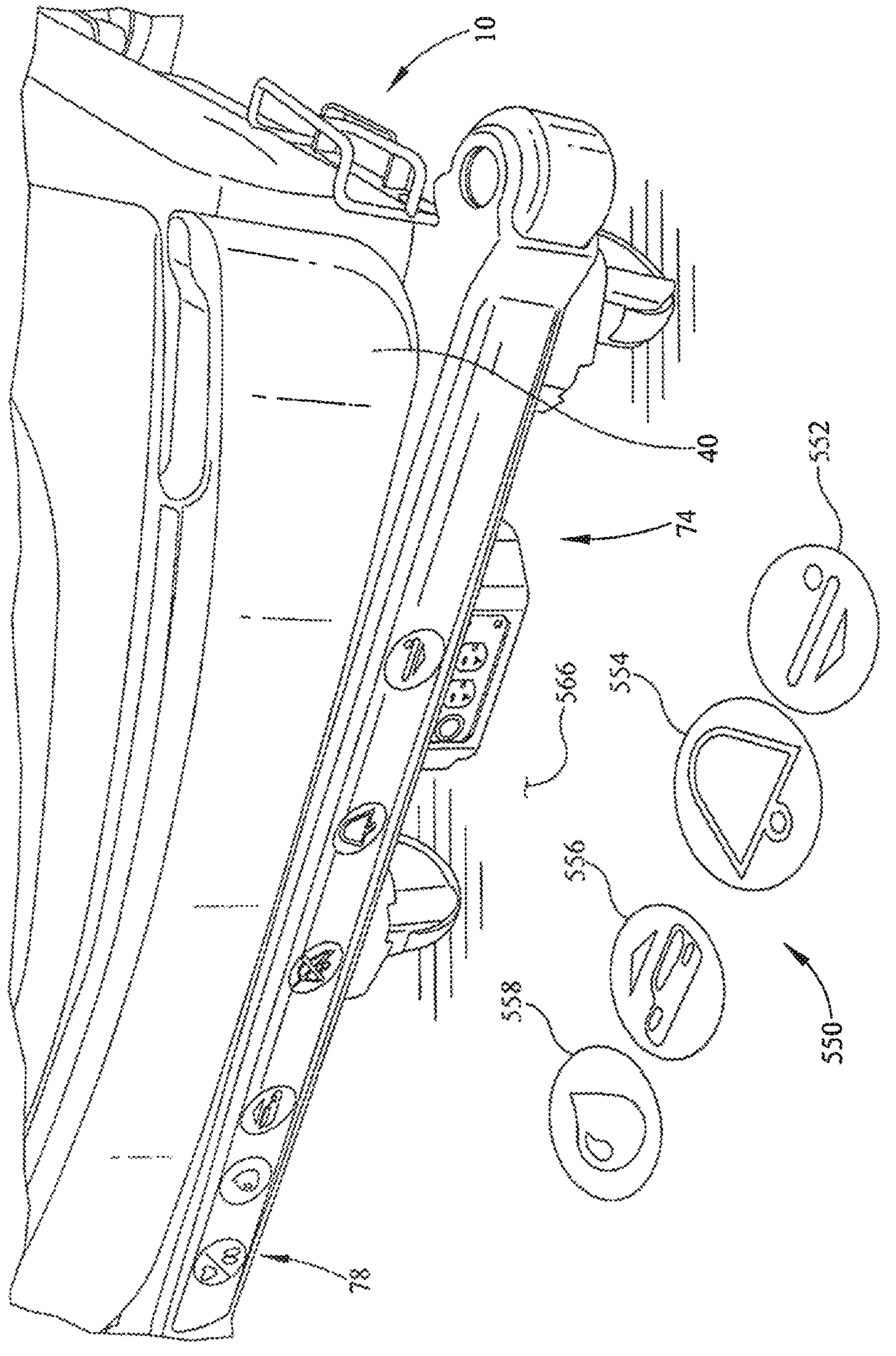
FIG. 32 is a perspective view of a portion of a patient support apparatus having a notification system that projects images on the floor surface spaced apart from the patient support apparatus.
Figure 33:
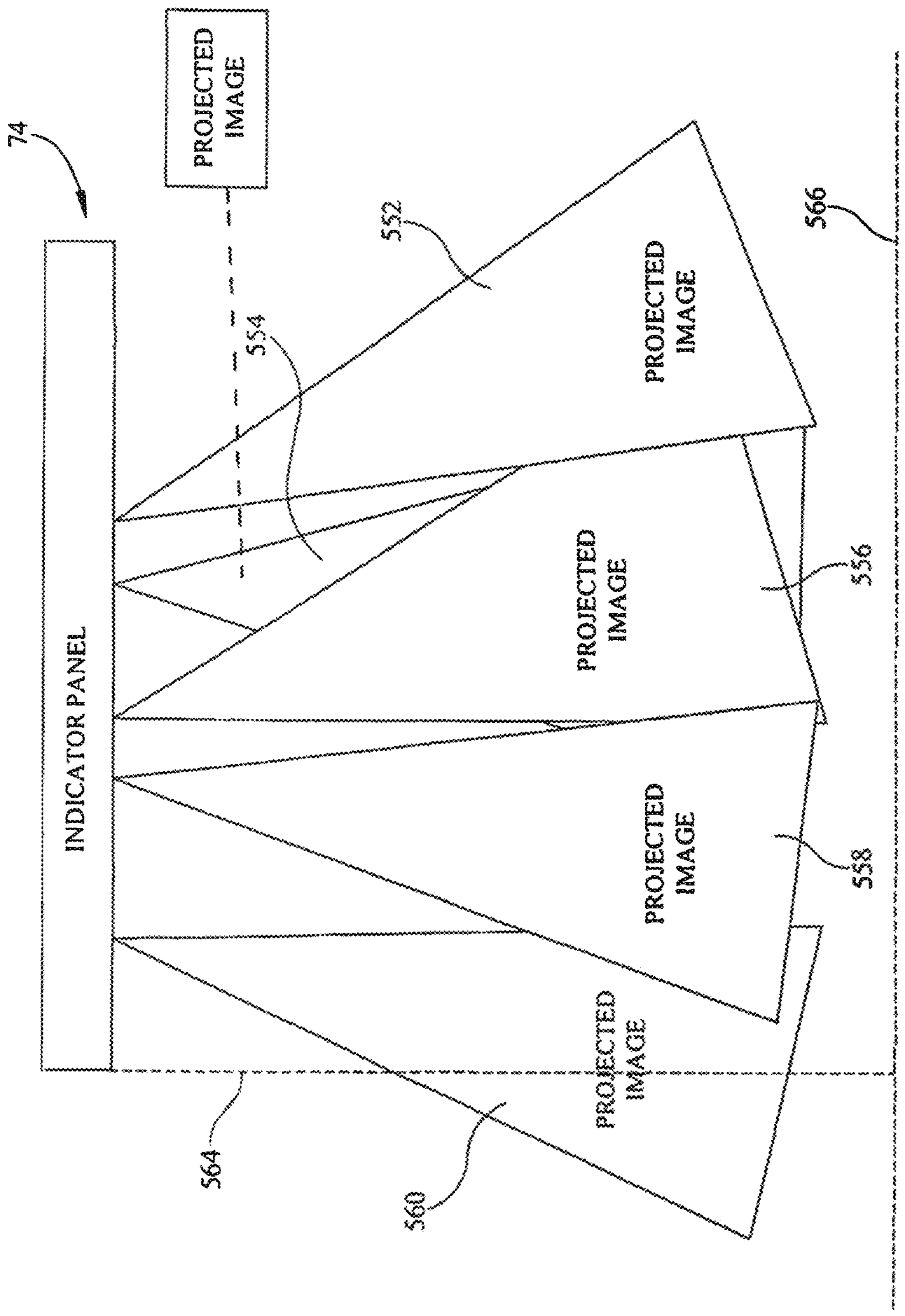
FIG. 33 is a diagrammatic representation of the scatter of images projected from the foot end of a patient support apparatus, the scatter resulting in variable projection angles in a first plane.
Figure 34:
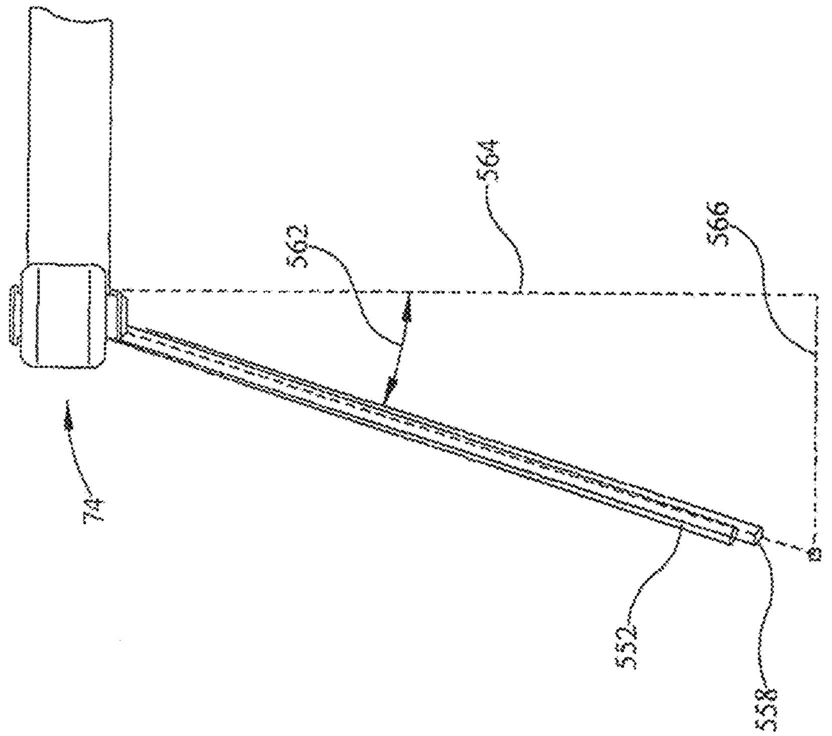
FIG. 34 is a diagrammatic representation of the scatter of images projected from the foot end of a patient support apparatus, the scatter resulting in variable projection angles in a second plane.
Figure 36:
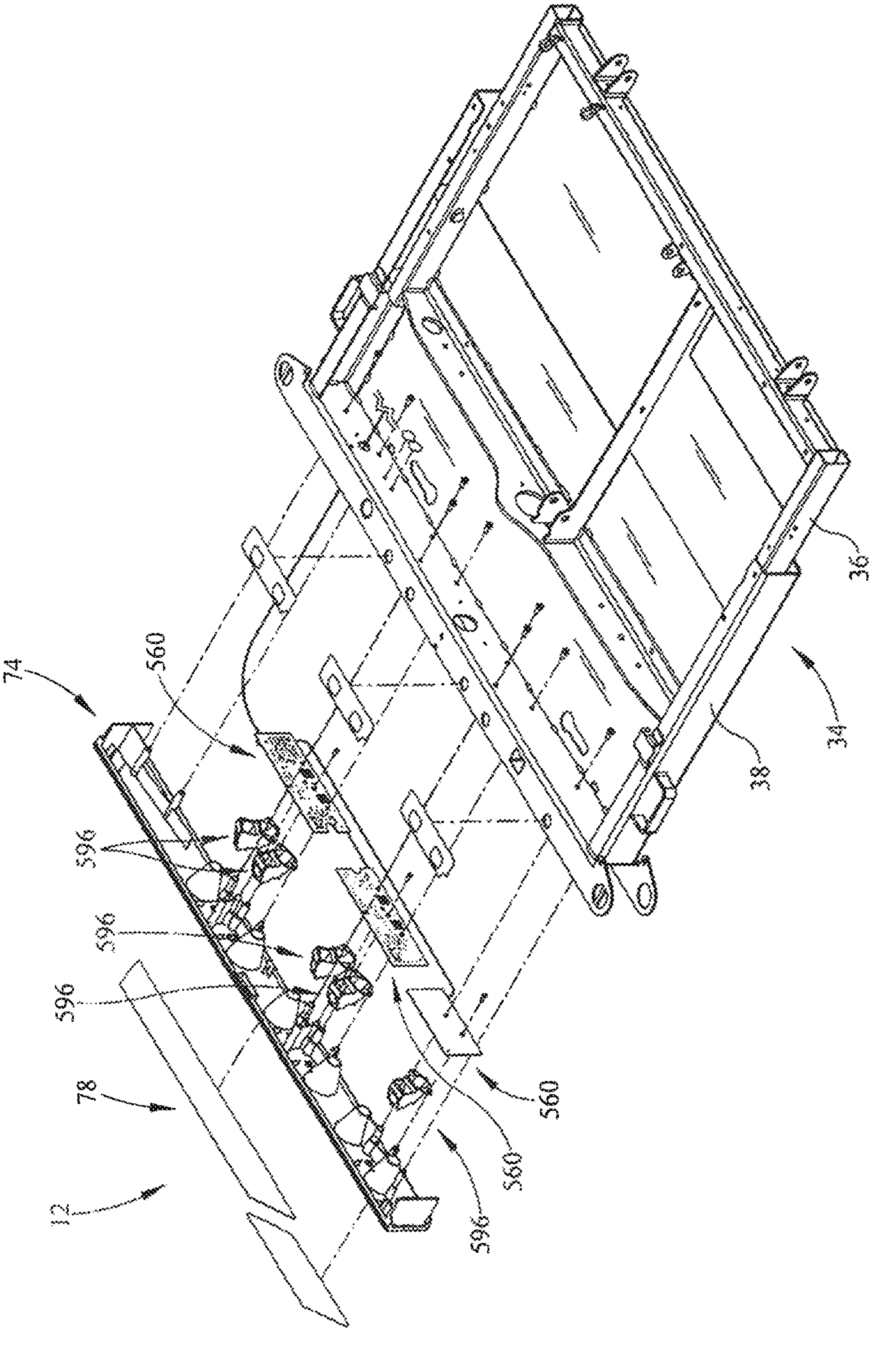
FIG. 36 is an exploded assembly view of the foot deck of a the patient support apparatus of FIG. 1 illustrating the arrangement of components of a portion of the notification system of the patient support apparatus.

In implementing the detection and notification system 160, a large amount of information is presented to the user/caregiver simultaneously, providing information at the graphical user interface 66, illuminated grips 76, indicator panel 74, and an image set 550 (seen in FIG. 32). While not illuminated in FIG. 31, the image set includes the image 82, along with images 552, 554, 556, and 558 that are each optionally illuminated onto the floor 566. Referring to FIG. 33, in the disclosed embodiment, the images 552, 554, 556, 558, and an alternate image 560, similar to image 82 but positioned in a different location than the embodiment of FIG. 1, are each projected from a respective illuminator 80. Referring to FIG. 36, each illuminator 80 includes a light source 568 and a projector 596. The diagrammatic views of FIGS. 33 and 34 illustrate how the images 552, 554, 556, 558, and 560 are projected at an acute angle 562 relative to vertical 564 in a first plane as shown in FIG. 34. In addition, the images 552, 554, 556, 558, and 560 are each projected at varied angles relative to vertical 564 in a second plane as shown in FIG. 33.

Figure 35:
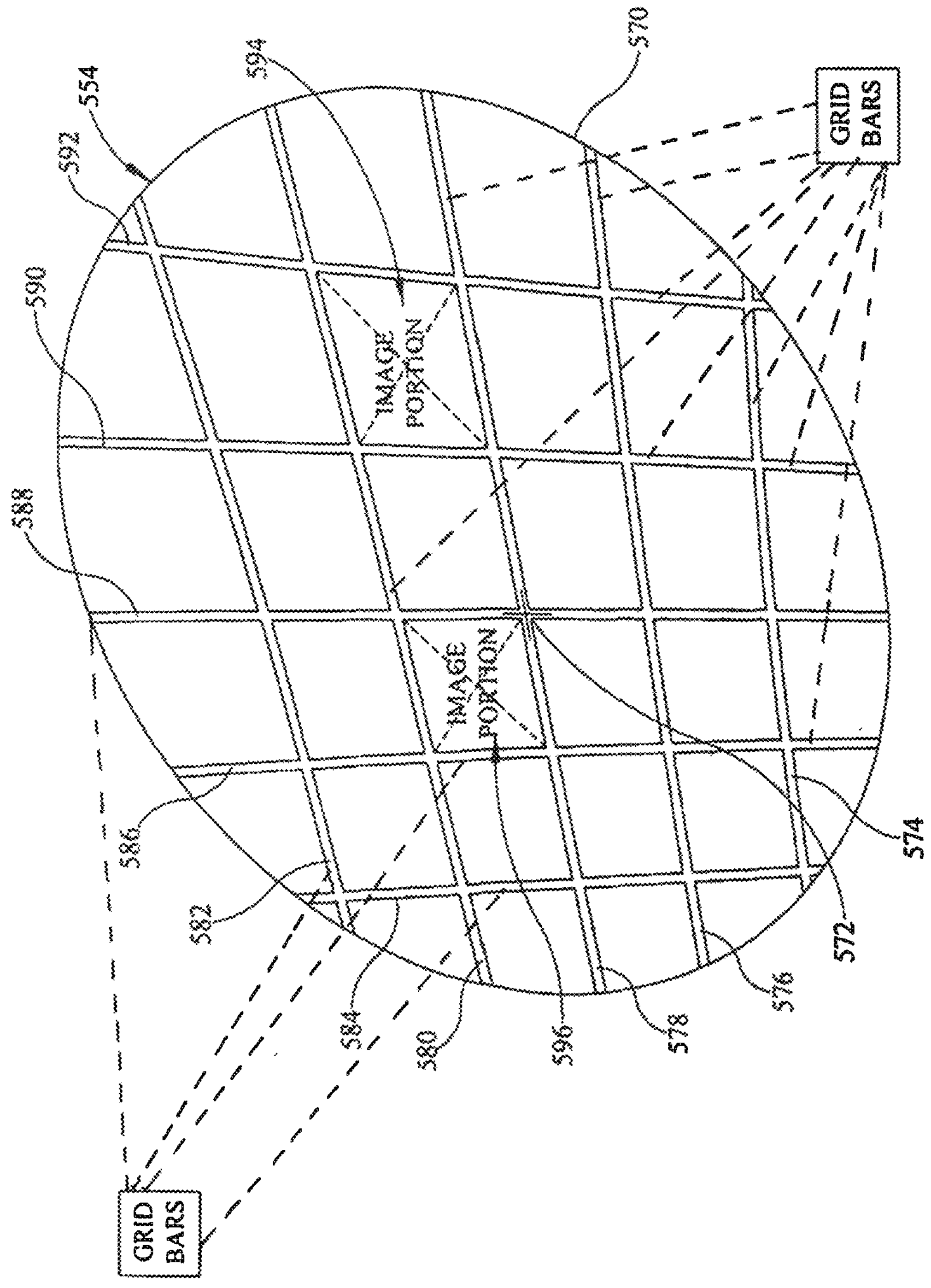
FIG. 35 is a diagrammatic representation of the distortion of an image when projected along a line of projection that is acute to the image plane, the image of FIG. 35 distorted in two directions.
Figure 37:
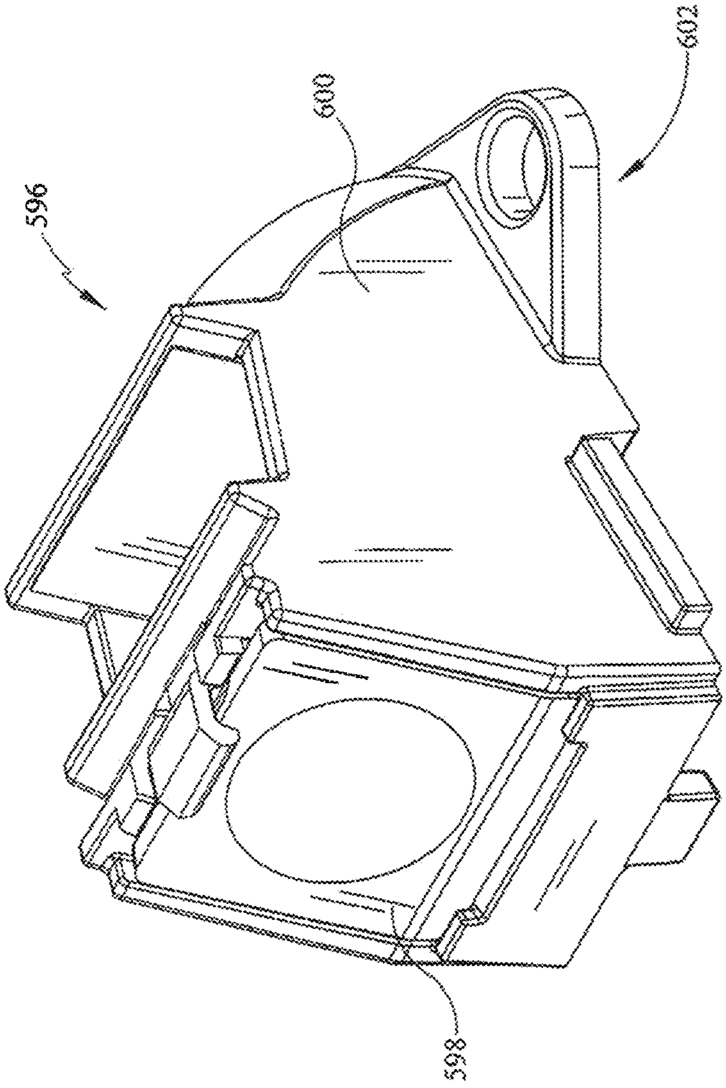
FIG. 37 is a perspective view of a projector assembly of the notification system.

The variation in the projection angles of the images 552, 554, 556, 558, and 560 would normally result in distortion of the resulting image 552, 554, 556, 558, and 560 on the floor 566 as illustrated in FIG. 35. The image shown in FIG. 35 is diagrammatic representation of the distortion experienced by the image 554 in one embodiment. The distorted image of FIG. 35 includes an origin 572 and a perimeter 570 that establishes the bound of the projected image 554 before a correction is applied, as will be discussed in further detail below. The diagram of FIG. 35 includes a number of grid bars 574, 576, 578, 580, and 582 that generally extend in a first direction. Another group of grid bars 584, 586, 588, 590, and 592 generally extend in a second direction. The projector 596 is shown in further detail in FIGS. 37 and 38 and includes an image lens 598 mounted to a body 600. The distorted version of image of FIG. 35 is the resulting projected image at the location of image 554 in FIG. 32, when the image lens 598 includes an overlay of orthogonal grid bars is projected onto the floor 566. In other words, at the lens 598, the grid bars 574, 576, 578, 580, and 582 are all substantially parallel and the grid bars 584, 586, 588, 590, and 592 are also substantially parallel and orthogonal to the grid bars 574, 576, 578, 580, and 582. The projected image, shown in FIG. 35, is distorted due the deviation of the projection angle from vertical. The region identified by reference numeral 596 has the same dimensions as the region 594 at the image lens 598, but is distorted at the image plane/floor 566.

Figure 38:
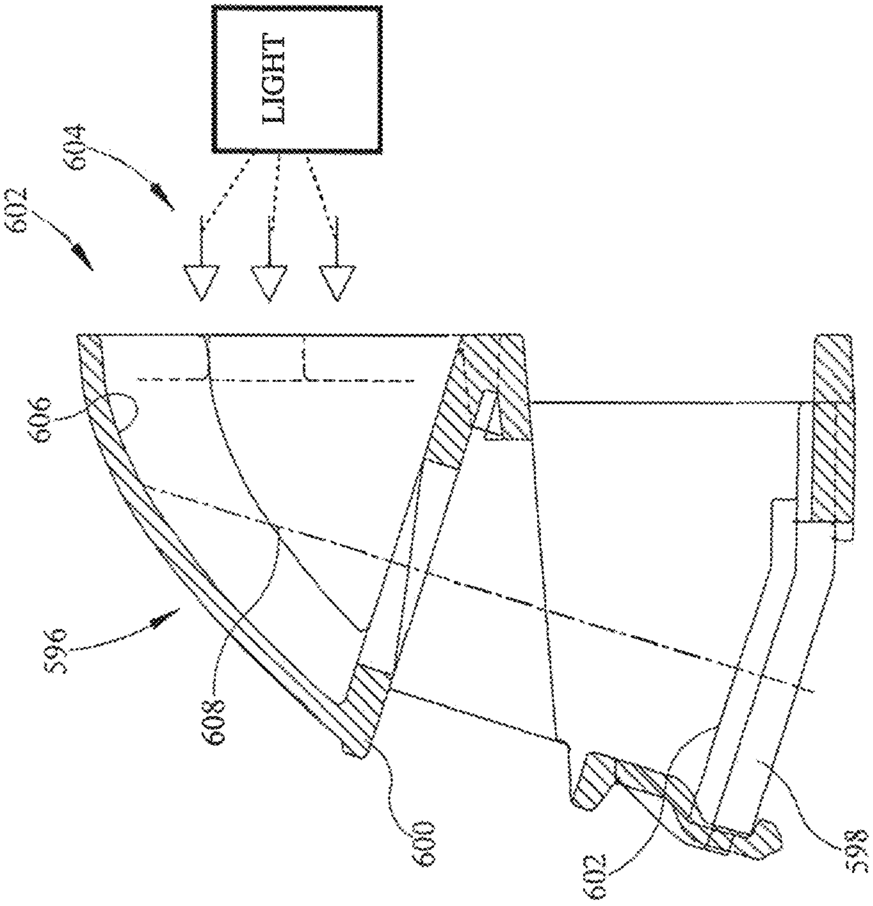
FIG. 38 is a cross-section al view of the projector assembly of FIG. 37.

Referring to FIG. 38, which is a cross-sectional view of the projector 596, it can be seen that light 604 enters an opening 602 in the projector body 600. The light 604 is collected at a parabolic reflection surface 606 that redirects the light along a direction 608 so that the light impinges upon the lens 598 perpendicular to a surface 610 of the lens 598. The use of the parabolic reflection surface 606 reduces light scatter that might tend to travel in a direction that is not perpendicular to the surface 610 and create ghosting of the projected image.

Figure 39:
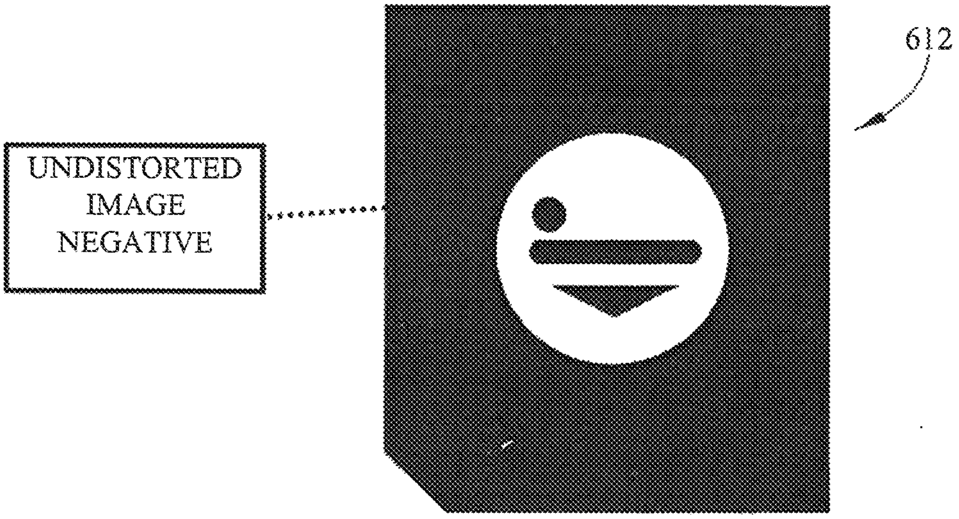
FIG. 39 is a diagrammatic illustration of an undistorted negative used in a lens of one of the projectors of the notification system.
Figure 40:
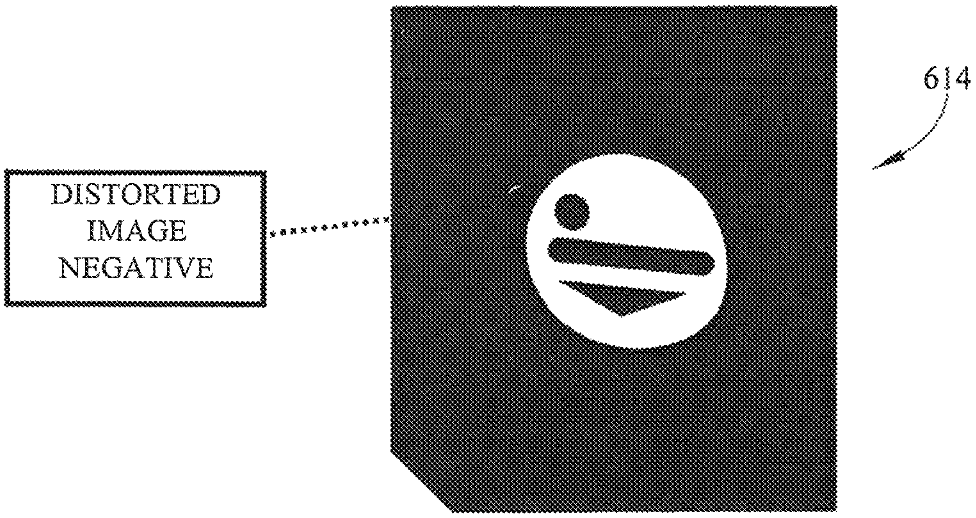
FIG. 40 is a diagrammatic illustration of an pre-distorted negative used in a lens of one of the projectors of the notification system, the pre-distortion being arranged to compensate for the projection angle of the particular projector such that the projected image is clear at the floor or another image plane.

To project a clear image at the image plane/floor 566, the image positioned on the lens 598 is pre-distorted to compensate for the compound projection angle relative to vertical 564 that results from the variation in the first plane in combination with the second plane. In other words, when the angle of projection is not orthogonal to the image plane/floor 566, the image positioned on the lens 598 is pre-distorted to compensate for the projection angle. As shown in FIG. 39, an undistorted pattern 612 is consistent with image 552. However, to achieve a clear image at the floor 566, a pattern 614, shown in FIG. 40, is actually used to compensate for the projection angle. In normal use, the bed 10 will be placed in the lowest position so that the standard height of portion 38 of foot deck 34 above the floor 566 is predetermined. The pre-distorted image of pattern 614 is optimized to provide a clear image 552 at the standard height. The pattern of pre-distortion for each image 552, 554, 556, 558, and 560 may be determined by measuring the variations exhibited by the grid bars 574, 576, 578, 580, and 582 and the grid bars 584, 586, 588, 590, and 592 and modifying the base pattern to provide a negative that is distorted proportionally to the variations found in the 574, 576, 578, 580, and 582 and the grid bars 584, 586, 588, 590, and 592 as suggested by the pattern 614. Because the projection angle of each image 552, 554, 556, 558, and 560 varies, the pre-distortion in each associated pattern must be adjusted for the specific image. Implementing such pre-distortion results in clear images as suggested in FIGS. 1 and 32.

Although certain illustrative embodiments have been described in detail above, variations and modifications exist within the scope and spirit of this disclosure as described and as defined in the following clauses and claims.

The following clauses provide illustrative examples of the various combinations of elements that might be achieved by implementing the aspects of the present disclosure. The combinations described in the clauses below are illustrative only, and not exhaustive.

Clause 1. A detection and notification system for a patient support apparatus comprising a sensor detecting a vital sign of a patient; a controller operable to receive a signal from the sensor indicative of the vital sign of the patient, the controller operable to compare the vital sign to pre-established limits to determine whether the vital sign is within an acceptable range; and a notification system operable to respond to commands from the controller to provide an indication as to whether the vital sign is within the acceptable range or that alarm condition exists, the indication discernible by a user spaced apart from the patient support apparatus that the detection notification system is associated.

Clause 2. The detection and notification system of clause 1, wherein the sensor simultaneously detects a first vital sign and a second vital sign.

Clause 3. The detection and notification system of clause 1, wherein the detection notification system includes a plurality of sensors simultaneously detecting a vital sign of the patient.

Clause 4. The detection and notification system of clause 3, wherein the plurality of sensors each detects both a first vital sign and a second vital sign.

Clause 5. The detection and notification system of clause 4, wherein the controller is operable to receive a signal from the patient support apparatus indicative of the position of a patient supported on the patient support apparatus, the controller operable to utilize the position of the patient to determine whether to disregard the vital sign information from one of the plurality of sensors.

Clause 6. The detection and notification system of clause 5, wherein the controller is operable to prompt a user to suspend the operation of the notification system based on the position of the patient.

Clause 7. The detection notification system of clause 1, wherein the controller is operable to receive a signal from the patient support apparatus indicative of the position of a patient supported on the patient support apparatus, and further operable to prompt the user to suspend operation of the notification system based on the position of the patient.

Clause 8. The detection and notification system of clause 7, wherein the controller is operable to receive signals indicative of the position of components of the patient support apparatus and to determine the acceptable range of the vital sign based, at least in part, on the position of at least one of the components of the patient support apparatus.

Clause 9. The detection and notification system of clause 8, wherein the controller is operable to communicate with an electronic medical record system to receive information from the electronic medical record system indicative of a medical history of a patient supported on the patient support apparatus and to determine the acceptable range of the vital sign based, at least in part, on the patient's medical history.

Clause 10. The detection and notification system of clause 9, wherein the controller is operable to utilize the medical history of the patient to perform an algorithm that analyzes the vital sign to determine that the patient is likely to experience an adverse event and to provide a notification discernible by a user that the likelihood of the adverse event has reached a threshold.

Clause 11. A patient support apparatus comprising at least one sensor, the at least one sensor operable to provide a signal indicative of a vital sign of a patient supported on the patient support apparatus, and a notification system coupled to the sensor, the notification system operable to process signals from the sensor which provide an indication of a vital sign to determine a vital sign, compare the vital sign to a predefined acceptable limit, and, if the vital sign deviates from the established acceptable limit, provide a visual indication of the deviation by illuminating a first iconic representation of vital signs in a first manner, if the status of the particular component does not deviate from the established acceptable operating condition for that component, illuminating the first iconic representation in a second manner.

Clause 12. The patient support apparatus of clause 11, wherein the notification system is operable to project the first iconic representation to a surface spaced apart from the patient support apparatus.

Clause 13. The patient support apparatus of clause 12, wherein the first iconic representation is simultaneously illuminated on a surface of the patient support apparatus and projected onto the surface spaced apart from the patient support apparatus.

Clause 14. The patient support apparatus of clause 13, wherein the first iconic representation is projected to the surface spaced apart from the patient support apparatus by a projector located on the patient support apparatus.

Clause 15. The patient support apparatus of clause 14, wherein illuminating the first iconic representation in a first manner comprises illuminating the first iconic representation in a first color and illuminating the first iconic representation in a second manner comprises illuminating the first iconic representation in a second color.

Clause 16. The patient support apparatus of clause 15, wherein providing the visual indication of the deviation includes simultaneously illuminating a first iconic representation of the component on a surface of the patient support apparatus in a first color and projecting the first iconic representation of the component on the surface spaced apart from the patient support apparatus in the first color.

Clause 17. The patient support apparatus of clause 16, wherein providing the visual indication of the lack of a deviation includes simultaneously illuminating a first iconic representation of the component on a surface of the patient support apparatus in a second color and projecting the first iconic representation of the component on the surface spaced apart from the patient support apparatus in the second color.

Clause 18. The patient support apparatus of clause 11, wherein providing the visual indication of the deviation includes simultaneously illuminating a first iconic representation of the component on a surface of the patient support apparatus in a first color and projecting the first iconic representation of the component on the surface spaced apart from the patient support apparatus in the first color.

Clause 19. The patient support apparatus of clause 18, wherein providing the visual indication of the lack of a deviation includes simultaneously illuminating a first iconic representation of the component on a surface of the patient support apparatus in a second color and projecting the first iconic representation of the component on the surface spaced apart from the patient support apparatus in the second color.

Clause 20. The patient support apparatus of clause 19, wherein the surface spaced apart from the patient support apparatus is the surface of a floor, the first iconic representation being projected to a position that is not directly below any portion of the patient support apparatus.

Clause 21. The patient support apparatus of clause 11, further comprising a frame, a barrier supported by the frame and movable vertically relative to the frame, a control system, and a user interface.

Clause 22. The patient support apparatus of clause 21, wherein a visual indication of the status of a patient position is provided at a foot end of the patient support apparatus.

Clause 23. The patient support apparatus of clause 21, wherein a visual indication of the status of the patient position is illuminated on a floor under the foot end of the patient support apparatus.

Clause 24. The patient support apparatus of clause 21, wherein a visual indication of the status of the patient position is provided by an illuminated grip on the barrier.

Clause 25. The patient support apparatus of clause 21, wherein a visual indication of the status of a condition of at least one feature of the patient support apparatus is provided at a foot end of the patient support apparatus.

Clause 26. The patient support apparatus of clause 21, wherein a visual indication of the status of a condition of at least one feature of the patient support apparatus is provided by illuminating an indication on the floor under the foot end of the patient support apparatus.

Clause 27. The patient support apparatus of clause 21, wherein the patient support apparatus includes structures which permit illumination of iconic representations on the floor beneath the patient support apparatus.

Clause 28. The patient support apparatus of clause 21, wherein the sensor is removably supported on the frame of the patient support apparatus.

Clause 29. The patient support apparatus of clause 28, wherein the frame is configured to support the sensor in multiple mounting locations.

Clause 30. The patient support apparatus of clause 29, wherein the patient support apparatus comprises multiple sensors, each sensor mounted at a different location on the frame.

Clause 31. The patient support apparatus of clause 30, wherein the control system is operable to detect a location of a patient and modify the operation of the notification system to disregard at least one of the sensors based on the patient location.

Clause 32. The patient support apparatus of clause 31, wherein the patient support apparatus includes two sensors mounted on a first frame member and one sensor mounted on a second frame member that is movable relative to the first frame member.

Clause 33. The patient support apparatus of clause 21, wherein the patient support apparatus further comprises a mattress supported on the frame and the sensor is located internally in the mattress.

Clause 34. The patient support apparatus of clause 11, wherein the patient support apparatus further comprises a frame and a mattress supported on the frame and the sensor is located internally in the mattress.

Clause 35. A patient support apparatus comprising a notification system operable of projecting indicia indicative of a condition associated with the patient support apparatus, the notification system including a light source and a projector assembly, the projector assembly operable to receive light from the light source and direct the light through a lens having a pre-distorted negative of the indicia such that when the light passes through the lens, an undistorted image is projected onto a surface spaced apart from the patient support apparatus.

Clause 36. The patient support apparatus of clause 35, wherein the projector assembly directs the light at a projection angle that is not orthogonal to the surface spaced apart from the patient support apparatus.

Clause 37. The patient support apparatus of clause 36, wherein the pre-distortion of the negative of the indicia is adjusted to correspond to the projection angle.

Clause 38. The patient support apparatus of clause 35, wherein the notification system includes a plurality of light sources and a plurality of projector assemblies, each projector assembly associated with a respective light source, each projector assembly operable to receive light from the respective light source and direct the light through a lens having a pre-distorted negative of the indicia such that when the light passes through the lens, an undistorted image is projected onto a surface spaced apart from the patient support apparatus, each projector assembly projecting a respective indicia, each indicia being indicative of a different condition.

Clause 39. The patient support apparatus of clause 38, wherein a first indicia is indicative of the condition of a patient vital sign and a second indicia is indicative of a status of a component of the patient support apparatus.

Clause 40. The patient support apparatus of clause 38, wherein each respective projection assembly projects at a projection angle that is not orthogonal to the surface spaced apart from the patient support apparatus, the pre-distortion of the negative associated we each respective projection assembly being adjusted to correspond to the projection angle of the particular projection assembly.

Clause 41. A patient support apparatus comprising, a controller, the controller coupled to memory which stores a serial number for the particular patient support apparatus, a replaceable component, the replaceable component including memory which stores a serial number for the replaceable component, and a user interface, wherein the controller is operable to execute a process which verify that the patient support apparatus is properly authorized to execute the functionality of the replaceable component by detecting the presence of the replaceable component, evaluating the serial number of one of the patient support apparatus and the replaceable component and provides an indication of the status of the authorization at the user interface.

Clause 42. The patient support apparatus of clause 41, wherein, if the controller determines that the functionality of the replaceable component is not properly authorized, the controller is operable to prompt a user to enter an authorization code before executing the functionality of the replaceable component at the user interface.

Clause 43. The patient support apparatus of clause 42, wherein the authorization code is based, at least in part, on the serial number of the replaceable component.

Clause 44. The patient support apparatus of clause 43, wherein the authorization code is based, at least in part, on the serial number of the patient support apparatus.

Clause 45. The patient support apparatus of clause 42, wherein the authorization code is based, at least in part, on the serial number of the patient support apparatus.

Clause 46. The patient support apparatus of clause 41, wherein the controller monitors for the presence of a replaceable component and regularly compares the serial number of the replaceable component with the serial number of the authorized replaceable component to determine if a different replaceable component has been substituted.

Clause 47. The patient support apparatus of clause 46, wherein, if the controller determines that a replaceable component has been substituted, the controller disables the functionality of the replaceable component and prompts the user to enter an authorization code for the substituted replaceable component at the user interface.

Clause 48. The patient support apparatus of clause 47, wherein the patient support apparatus comprises a detection and notification system for monitoring at least one vital sign of a patient supported on the patient support apparatus and the replaceable component is a vital sign sensor.

Clause 49. The patient support apparatus of clause 48, wherein the detection and notification system comprises multiple sensors, each sensor being monitored by the controller to determine that the patient support apparatus has been authorized for the particular sensor.

Clause 50. The patient support apparatus of clause 49, wherein the controller provides an indication of the status of the authorization at the user interface.

Clause 51. A patient support apparatus comprising a detection and notification system for detecting at least one vital sign of a patient supported on the patient support apparatus, the detection and notification system including a sensor detecting a vital sign of the patient, the sensor not in contact with the patient; a controller operable to receive a signal from the sensor indicative of the vital sign of the patient, the controller operable to compare the vital sign to pre-established limits to determine whether the vital sign is within an acceptable range; and a notification system operable to respond to commands from the controller to provide an indication as to whether the vital sign is within the acceptable range or that alarm condition exists, the indication discernible by a user spaced apart from the patient support apparatus.

Clause 52. The patient support apparatus of clause 51, wherein the sensor detects multiple vital signs.

Clause 53. The patient support apparatus of any of preceding clauses 51-52, wherein the sensor simultaneously detects multiple vital signs.

Clause 54. The patient support apparatus of any of preceding clauses 51-53, wherein the sensor comprises a plurality of sensors.

Clause 55. The patient support apparatus of any of preceding clauses 51-54, wherein the patient support apparatus is configured to permit a particular sensor to be positioned in any one of a number of positions on the patient support apparatus.

Clause 56. The patient support apparatus of any of preceding clauses 51-55, wherein the controller is operable to disregard the signal of a sensor.

Clause 57. The patient support apparatus of any of preceding clauses 51-56, wherein the controller is operable to disregard the signal of a sensor if a the controller determines that a patient is not properly positioned to be monitored by the sensor.

Clause 58. The patient support apparatus of any of preceding clauses 51-57, wherein the patient support apparatus includes a user interface in communication with the controller, the user interface operable to provide an indication of the status of at least one vital sign of the patient.

Clause 59. The patient support apparatus of any of preceding clauses 51-58, wherein the sensor simultaneously detects multiple vital signs and the patient support apparatus includes a user interface in communication with the controller, the user interface operable to provide an indication of the status of each detected vital sign of the patient.

Clause 60. The patient support apparatus of any of preceding clauses 51-59, wherein the controller is configured to allow a user to set alarm limits for a detected vital sign.

Clause 61. The patient support apparatus of any of preceding clauses 51-60, wherein the notification system operable to respond to commands from the controller to provide an indication as to whether a signal has been lost from a sensor.

Clause 62. The patient support apparatus of any of preceding clauses 51-61, wherein the controller is operable to monitor the signal from the sensor and determine if an adverse event is likely to occur based on the signal, independently of whether the signal exceeds a pre-set limit.

Clause 63. The patient support apparatus of any of preceding clauses 51-62, wherein the notification system is operable to provide an indication of the likelihood of the adverse event.

Clause 64. The patient support apparatus of any of preceding clauses 51-63, wherein the notification system is adjustable to provide local indications of a condition, remote indications of a condition, or both local and remote indications of a condition.

Clause 65. The patient support apparatus of any of preceding clauses 51-64, wherein the notification system is operable to prompt a user to either accept or rejection questionable data.

Clause 66. The patient support apparatus of any of preceding clauses 51-65, wherein the patient support apparatus includes a mattress and a sensor is positioned in the mattress.

Clause 67. The patient support apparatus of any of preceding clauses 51-66, wherein the controller determines whether a particular sensor has been authorized for use on the patient support apparatus.

Clause 68. The patient support apparatus of any of preceding clauses 51-67, wherein the controller prompts a user to enter an authorization code if a particular sensor has not previously been authorized for use on the patient support apparatus.

Clause 69. The patient support apparatus of any of preceding clauses 51-68, wherein the controller continuously monitors to confirm that a particular sensor has been authorized for use on the patient support apparatus and if a new sensor is substituted, controller prompts a user to enter an authorization code if a particular sensor has not previously been authorized for use on the patient support apparatus.

Clause 70. The patient support apparatus of any of preceding clauses 51-69, wherein an alert limit for a vital sign is determined automatically by the controller.

Clause 71. The patient support apparatus of any of preceding clauses 51-70, wherein the controller determines an alert limit for a vital sign based on patient medical history information from an electronic medical record system in communication with the controller.

Clause 72. The patient support apparatus of any of preceding clauses 51-71, wherein the controller determines an alert limit for a vital sign based on based on a bed condition.

Clause 73. The patient support apparatus of any of preceding clauses 51-72, wherein the patient support apparatus comprises a siderail with a grip and the notification system provides an indication as to whether the vital sign is within the acceptable range or that alarm condition exists at the grip by illuminating the grip in a color associated with a status of the vital sign.

Clause 74. The patient support apparatus of any of preceding clauses 51-73, wherein the patient support apparatus includes a touchscreen and the notification system provides an indication as to whether the vital sign is within the acceptable range or that alarm condition exists at a touchscreen.

Clause 75. The patient support apparatus of any of preceding clauses 51-74, wherein the patient support apparatus includes indicator panel and the notification system provides an indication as to whether the vital sign is within the acceptable range or that alarm condition exists at the indicator panel.

Clause 76. The patient support apparatus of any of preceding clauses 51-75, wherein the patient support apparatus includes a link to an external nurse call system and the notification system provides an indication as to whether the vital sign is within the acceptable range or that alarm condition exists through the link.

Clause 77. The patient support apparatus of any of preceding clauses 51-76, wherein the patient support apparatus includes a projection system for projecting indicia to a surface spaced apart from the patient support apparatus and the notification system provides an indication as to whether the vital sign is within the acceptable range or that alarm condition exists by projecting indicia associated with the status of the vital sign on the surface.

Clause 78. The patient support apparatus of any of preceding clauses 51-77, wherein the projection system includes a light source and a projector assembly, the projector assembly operable to receive light from the light source and direct the light through a lens having a pre-distorted negative of the indicia such that when the light passes through the lens, an undistorted image is projected onto a surface spaced apart from the patient support apparatus.

Clause 79. The patient support apparatus of clause 78, wherein the projector assembly directs the light at a projection angle that is not orthogonal to the surface spaced apart from the patient support apparatus.

Clause 80. The patient support apparatus of clause 79, wherein the pre-distortion of the negative of the indicia is adjusted to correspond to the projection angle.

Clause 81. The patient support apparatus of any of clauses 77-80, wherein the notification system includes a plurality of light sources and a plurality of projector assemblies, each projector assembly associated with a respective light source, each projector assembly operable to receive light from the respective light source and direct the light through a lens having a pre-distorted negative of the indicia such that when the light passes through the lens, an undistorted image is projected onto a surface spaced apart from the patient support apparatus, each projector assembly projecting a respective indicia, each indicia being indicative of a different condition.

Clause 82. The patient support apparatus of clause 81, wherein a first indicia is indicative of the condition of a patient vital sign and a second indicia is indicative of a status of a component of the patient support apparatus.

Clause 83. The patient support apparatus of any of clauses 81-82, wherein each respective projection assembly projects at a projection angle that is not orthogonal to the surface spaced apart from the patient support apparatus, the pre-distortion of the negative associated we each respective projection assembly being adjusted to correspond to the projection angle of the particular projection assembly.

The invention claimed is:

1. A patient support apparatus comprising:

a controller, the controller coupled to memory which stores a specific serial number for the patient support apparatus, a replaceable component, the replaceable component including memory which stores a specific serial number for the replaceable component, and a user interface, wherein the controller determines that a functionality of the replaceable component is not properly authorized for use with the patient support apparatus, wherein the controller calculates an authorization code based, at least in part, on at least one of the serial number of the patient support apparatus and the serial number of the replaceable component, and if the replaceable component is not properly authorized for use with the patient support apparatus, the controller is operable to prompt a user to enter an authorization code at the user interface before executing the functionality of the replaceable component, wherein the controller compares the entered authorization code to the calculated authorization code and, upon determining that the entered authorization code matches the calculated authorization code, enables the functionality of the replaceable component.

2. The patient support apparatus wherein the controller determines that the functionality of the replaceable component is properly authorized by comparing the serial number of the patient support apparatus and the serial number of the replaceable component and only enables operation of the replaceable component if an acceptable authorization code has been entered.

3. The patient support apparatus of claim 2, wherein the controller determines the entered authorization code based, at least in part, on the serial number of the replaceable component.

4. The patient support apparatus of claim 3, wherein the entered authorization code is based, at least in part, on the serial number of the patient support apparatus.

5. The patient support apparatus of claim 2, wherein the entered authorization code is based, at least in part, on the serial number of the patient support apparatus.

6. The patient support apparatus of claim 2, wherein the controller monitors for a presence of the replaceable component and regularly compares the serial number of the replaceable component with a serial number of an authorized replaceable component to determine if a different replaceable component has been substituted, and disables the functionality of the replaceable component if the different replaceable component has been connected to the controller.

7. The patient support apparatus of claim 6, wherein, if the controller determines that the different replaceable component has been substituted, the controller prompts the user to enter a substituted authorization code for the substituted different replaceable component at the user interface.

8. The patient support apparatus of claim 7, wherein the patient support apparatus comprises a detection system and a notification system for monitoring at least one vital sign of a patient supported on the patient support apparatus and the replaceable component is a vital sign sensor.

9. The patient support apparatus of claim 8, wherein the detection system and the notification system comprises multiple sensors, each sensor being monitored by the controller to determine that the patient support apparatus has been authorized for each sensor of the multiple sensors.

10. The patient support apparatus of claim 9, wherein the controller provides an indication of a status that the patient support apparatus has been authorized for said each sensor of the multiple sensors at the user interface.

11. The patient support apparatus of claim 1, wherein the controller monitors for a presence of the replaceable component and regularly compares the serial number of the replaceable component with a serial number of an authorized replaceable component to determine if a different replaceable component has been substituted and disables the functionality of the replaceable component if the different replaceable component has been connected to the controller.

12. The patient support apparatus of claim 11, wherein, if the controller determines that the different replaceable component has been substituted, the controller prompts the user to enter a substituted authorization code for the substituted different replaceable component at the user interface.

13. The patient support apparatus of claim 12, wherein the patient support apparatus comprises a detection system and a notification system for monitoring at least one vital sign of a patient supported on the patient support apparatus and the replaceable component is a vital sign sensor.

14. The patient support apparatus of claim 13, wherein the detection system and the notification system comprises multiple sensors, each sensor being monitored by the controller to determine that the patient support apparatus has been authorized for each sensor of the multiple sensors.

15. The patient support apparatus of claim 14, wherein the controller provides an indication of a status that the patient support apparatus has been authorized for said each sensor of the multiple sensors at the user interface.

16. The patient support apparatus of claim 13, wherein the notification system is operable to process signals from the vital sign sensor which provide an indication of a vital sign, compare the vital sign to a predefined acceptable limit, and, if the vital sign deviates from the predefined acceptable limit, provide a visual indication of the deviation of the vital sign by illuminating a first iconic representation of vital signs in a first manner, if the vital sign does not deviate from the predefined acceptable limit, illuminating the first iconic representation in a second manner.

17. The patient support apparatus of claim 16, wherein the notification system is operable to project the first iconic representation to a surface spaced apart from the patient support apparatus.

18. The patient support apparatus of claim 17, wherein the first iconic representation is simultaneously illuminated on a surface of the patient support apparatus and projected onto the surface spaced apart from the patient support apparatus.

19. The patient support apparatus of claim 18, wherein the first iconic representation is projected to the surface spaced apart from the patient support apparatus by a projector located on the patient support apparatus.

20. The patient support apparatus of claim 19, wherein illuminating the first iconic representation in the first manner comprises illuminating the first iconic representation in a first color and illuminating the first iconic representation in the second manner comprises illuminating the first iconic representation in a second color.

* * * * *